United States Patent
Miki et al.

(10) Patent No.: US 6,294,536 B1
(45) Date of Patent: Sep. 25, 2001

(54) TRIAZINE DERIVATIVES, THEIR PRODUCTION AND USE

(75) Inventors: Hideki Miki, Toyono-gun; Isao Aoki, Kawanishi; Toshikatsu Hayashi, Fukuchiyama, all of (JP)

(73) Assignee: Takeda Schering-Plough Animal Health K.K., Osaka (JP)

( * ) Notice: Subject to any disclaimer, the term of this patent is extended or adjusted under 35 U.S.C. 154(b) by 0 days.

(21) Appl. No.: 09/445,159

(22) PCT Filed: Aug. 27, 1998

(86) PCT No.: PCT/JP98/03796

§ 371 Date: Mar. 1, 2000

§ 102(e) Date: Mar. 1, 2000

(87) PCT Pub. No.: WO99/11634

PCT Pub. Date: Mar. 11, 1999

(30) Foreign Application Priority Data

Aug. 29, 1997 (JP) .................................................... 9-234819

(51) Int. Cl.⁷ .......................... A61K 31/53; A61P 33/02; C07D 253/06
(52) U.S. Cl. ............................................ 514/242; 544/182
(58) Field of Search .............................. 544/182; 514/242

(56) References Cited

U.S. PATENT DOCUMENTS

| | | | |
|---|---|---|---|
| 4,631,278 | 12/1986 | Boeckx et al. | 544/182 |
| 4,782,056 | 11/1988 | Rosner et al. | 544/182 |
| 5,114,938 | 5/1992 | Lindner et al. | 544/182 |
| 5,188,832 | 2/1993 | Mehlhorn et al. | 544/83 |
| 5,214,043 | 5/1993 | Lindner et al. | 544/182 |
| 5,256,631 | 10/1993 | Lindner et al. | 504/229 |

FOREIGN PATENT DOCUMENTS

| | | |
|---|---|---|
| 2532363 | 7/1975 | (DE) . |
| 0 232 932 A1 | 6/1987 | (EP) . |
| 0 648 760 A2 | 10/1994 | (EP) . |
| 0 737 672 A2 | 4/1996 | (EP) . |
| 0 831 088 A1 | 8/1997 | (EP) . |

OTHER PUBLICATIONS

Journal of Medicinal Chemistry, vol. 22, No. 12, p. 1483–1487, 1979.
Journal of Medicinal Chemistry, vol. 26, No. 1, p. 96–100, 1983.
Journal of Medicinal Chemistry, vol. 24, No. 11, p. 1337–1342, 1981.
Journal of Medicinal Chemistry, vol. 20, No. 4, p. 475.483, 1977.
Journal of Medicinal Chemistry, vol. 23, No. 10, p. 1083–1087, 1980.

*Primary Examiner*—John M. Ford
*Assistant Examiner*—Venkataraman Balasubramanian
(74) *Attorney, Agent, or Firm*—Merchant & Gould P.C.

(57) ABSTRACT

The present invention relates to compounds represented by the formula:

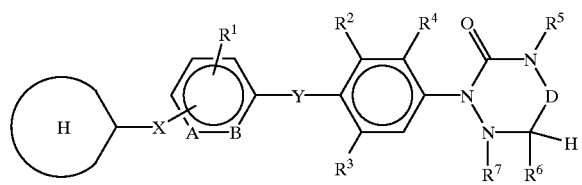

wherein ring H represents an optionally substituted aromatic heterocyclic group or an optionally substituted alicyclic hydrocarbon group; X and Y independently represent a single bond, —O—, a group of the formula: —S(O)$_m$— wherein m is 0, 1 or 2, a group of the formula: —NR$^8$— wherein R$^8$ represents a hydrogen atom, an alkyl group or an acyl group, —CO— or an optionally substituted methylene group; —A—B— represents —N=CH—, —CH=N—, —N=N— or —CH=CH—; R$^1$ represents a hydrogen atom, a halogen atom, an optionally substituted alkyl group which may be bonded through a hetero atom or an acyl group; R$^2$ and R$^3$ independently represent a hydrogen atom, a halogen atom or an optionally substituted alkyl group; R$^4$ represents a hydrogen atom or a halogen atom; R$^5$ represents a hydrogen atom, an optionally substituted alkyl group or an acyl group; R$^6$ and R$^7$ independently represent a hydrogen atom or R$^6$ and R$^7$ may form a chemical bond together with each other; and D represents —CH$_2$— or —CO—; or a salt thereof. These compounds and salts thereof are useful as anti-protozoal agents.

16 Claims, No Drawings

TRIAZINE DERIVATIVES, THEIR PRODUCTION AND USE

TECHNICAL FIELD

The present invention relates to a new triazine derivative, a method of its production, and use thereof. More specifically, the present invention relates to a new triazine derivative that is useful for the control of parasitic protozoa such as coccidia, or a salt thereof, a method of its production, and an anti-protozoal containing it.

BACKGROUND ART

Parasitic protozoa are widely parasitic to animals, such as mammals, fowls, fish, and insects. They mainly parasitize animal internal organs, or skin, eyes, etc., and significantly damage the host, resulting in vast economic loss in domestic animal and poultry and fish industries. Coccidiosis, a parasitic protozoal disease in poultry, is caused mainly by several parasitic protozoa of the genus Eimeria, such as *E. tenella, E. necatrix, E. acervulina, E. maxima, E. brunetti*, and *E. mivati*. For example, *E. tenella* parasitizes the walls of the chicken cecum and other intestines to fatally affect the host. Specifically, this infection is manifested as symptoms such as intestinal wall erosion, inflammation and bleeding due to a broad range of intestinal invasion, cecal blood retention, and associated appetite loss and poor growth. Internal parasitic protozoa are generally transmitted orally. In the case of coccidiosis, in particular, oocyst inactivation is impossible even by potent disinfestation with potassium bichromate solution. In addition, because of the generation cycle of as short as about 7 days, there is no effective countermeasure against its rapid infection and onset in large-scale animal breeding.

In the case of fish, protozoa that mainly parasitize external organs are of concern; their parasitization damages the fish skin and gills, and weakens their essential resistance to infectious diseases, which in turn can cause death. In large-scale fish culture, parasitic protozoa spread rapidly over the whole fish in culture, posing a significant problem of economic loss due to such damage.

The same applies to insects. In the case of honeybees, for example, protozoa, such as *Nosema apis*, have heavily damaged commercial beekeeping all over the world. This parasitic protozoon makes the host less resistant and more susceptible to other diseases, by destroying the host's internal organs.

Traditionally, a large number of chemicals against parasitic protozoa have been known, which, for the most part, are narrow in target and action spectrum, and some have been reported to be ineffective against protozoa that have acquired resistance. In addition, these chemicals are required to be administered at high doses because of their low activity, and are therefore unsatisfactory in terms of economic and environmental aspects. For these reasons, there is strong need for the development of a new chemical that can be widely used with excellent action in the control of parasites in vertebrates, such as mammals, fowls and fish, and insects.

As such drugs, 2-phenyl-6-azauracil derivatives were found to have anti-coccidium action [Journal of Medicinal Chemistry, Vol. 22, p. 1483 (1979)]; various 6-azauracil derivatives were synthesized and investigated but proved to be teratogenic and failed to come into practical application. Later, as nonteratogenic compounds, 2-phenyl-1,2,4-triazinedione compounds, such as a 2-(4-phenoxyphenyl)-1,2,4-triazine derivative [DE-A-2532363] and 2-[4-(1-cyano-1-phenylmethyl)phenyl]-1,2,4-triazine derivative [U.S. Pat. No. 4,631,278], have been developed, some of which have been used to control coccidia in some European countries, Australia, and others but have not been approved for use in Japan, the Unites States and other countries.

DISCLOSURE OF INVENTION

Against the above-described technical background, the present inventors made extensive investigations and found that a series of new triazine derivatives exhibit excellent action against parasitic protozoa. After further investigations, the inventors found that this series of derivatives are suited for the control of various parasitic protozoa encountered in animal breeding (vertebrates, such as mammals, fowls, and fish, and insects), that they are low in toxicity and retention tendency in animals, that they have very high biological effects on strains that are resistant to conventional drugs, and that are excellent in terms of safety. The inventors thus developed the present invention.

Namely, the present invention relates to:

[1] a compound represented by the formula:

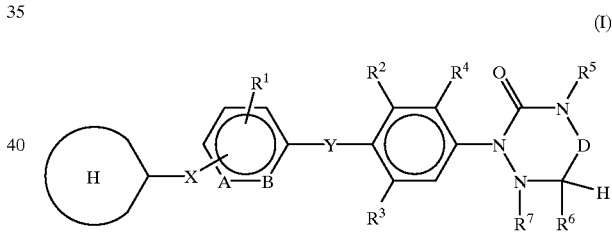

(I)

wherein ring H represents an optionally substituted aromatic heterocyclic group or an optionally substituted alicyclic hydrocarbon group; X and Y independently represent a single bond, —O—, a group of the formula: —S(O)$_m$— wherein m is 0, 1 or 2, a group of the formula: —NR$^8$— wherein R$^8$ represents a hydrogen atom, an alkyl group or an acyl group, —CO— or an optionally substituted methylene group; —A—B— represents —N=CH—, —CH=N—, —N=N— or —CH=CH—; R$^1$ represents a hydrogen atom, a halogen atom, an optionally substituted alkyl group which may be bonded through a hetero atom or an acyl group; R$^2$ and R$^3$ independently represent a hydrogen atom, a halogen atom or an optionally substituted alkyl group; R$^4$ represents a hydrogen atom or a halogen atom; R$^5$ represents a hydrogen atom, an optionally substituted alkyl group or an acyl group; R$^6$ and R$^7$ independently represent a hydrogen atom or R$^6$ and R$^7$ may form a chemical bond together with each other; and D represents —CH$_2$— or —CO— (hereinafter referred to briefly as the compound (I)), or a salt thereof, Specifically the present invention relates to:

[1] a compound represented by the formula:

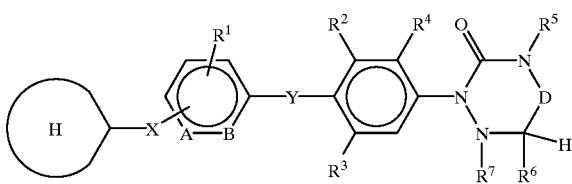

wherein ring H represents an optionally substituted aromatic heterocyclic group or an optionally substituted alicyclic hydrocarbon group; X and Y independently represent a single bond, —O—, a group of the formula: —S(O)$_m$— wherein m is 0, 1 or 2, a group of the formula: —NR$^8$— wherein R$^8$ represents a hydrogen atom, an alkyl group or an acyl group, —CO— or an optionally substituted methylene group; —A—B— represents —N=CH—, —CH=N—, —N=N— or —CH=CH—; R$^1$ represents a hydrogen atom, a halogen atom, an optionally substituted alkyl group which may be bonded through a hetero atom or an acyl group; R$^2$ and R$^3$ independently represent a hydrogen atom, a halogen atom or an optionally substituted alkyl group; R$^4$ represents a hydrogen atom or a halogen atom; R$^5$ represents a hydrogen atom, an optionally substituted alkyl group or an acyl group; R$^6$ and R$^7$ independently represent a hydrogen atom or R$^6$ and R$^7$ may form a chemical bond together with each other; and D represents —CH$_2$— or —CO—; or a salt thereof,

[2] the compound as described in [1] above or a salt thereof, wherein ring H is a 5- or 6-membered aromatic heterocyclic group, a condensed ring group of a 5- or 6-membered aromatic heterocyclic ring with a benzene ring or a 5- or 6-membered aromatic heterocyclic ring, a C$_{3-14}$ cycloalkyl group or a C$_{3-14}$ cycloalkenyl group, each of which may optionally be substituted with a substituent or substituents selected from the group consisting of (1) hydroxy, (2) amino, (3) cyano, (4) sulfamoyl, (5) sulfamoyloxy, (6) sulfo, (7) mercapto, (8) nitro, (9) oxo, (10) thioxo, (11) halogen, (12) a hydrocarbon group selected from the group consisting of (i) a C$_{1-6}$ alkyl group, (ii) a C$_{3-14}$ cycloalkyl group, (iii) a C$_{2-6}$ alkenyl group, (iv) a C$_{3-14}$ cycloalkenyl group, (v) a C$_{2-6}$ alkynyl group, (vi) a C$_{6-14}$ aryl group and (vii) a C$_{7-19}$ aralkyl group, wherein the hydrocarbon group may optionally be substituted with halogen or hydroxy, (13) a hydrocarbon-oxy group wherein the hydrocarbon group of the hydrocarbon-oxy group has the same meanings as the hydrocarbon group defined in (12) as mentioned above, (14) a hydrocarbon-thio group wherein the hydrocarbon group of the hydrocarbon-thio group has the same meanings as the hydrocarbon group defined in (12) as mentioned above, (15) benzoyl and (16) a 5- or 6-membered heterocyclic group,

[3] the compound as described in [1] above or a salt thereof, wherein R$^8$ is a hydrogen atom, a C$_{1-6}$ alkyl group or an C$_{1-20}$ acyl group,

[4] the compound as described in [1] above or a salt thereof, wherein the substituent of methylene is selected from the group consisting of (1) a C$_{1-6}$ alkyl group which may optionally be substituted with (i) hydroxy, (ii) a C$_{1-4}$ alkylthio group, (iii) halogen, (iv) a C$_{1-6}$ alkoxy group, (v) nitro, (vi) a C$_{1-6}$ alkoxy-

[II] a compound represented by the formula:

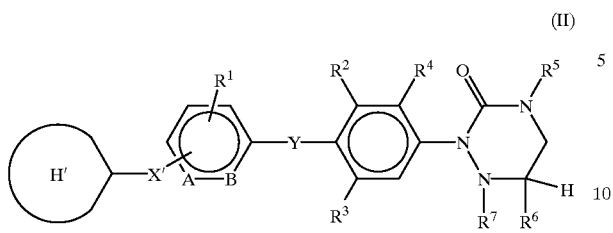

wherein ring H' is a phenyl group which may optionally be substituted with halogen and/or hydroxy; X' is a methylene group which may optionally be substituted with a substituent selected from the group consisting of a C$_{1-6}$ alkyl group and hydroxy; and the other symbols have the same meanings as defined in [I] above (hereinafter referred to briefly as the compound (II)), or a salt thereof,

[III] a compound represented by the formula:

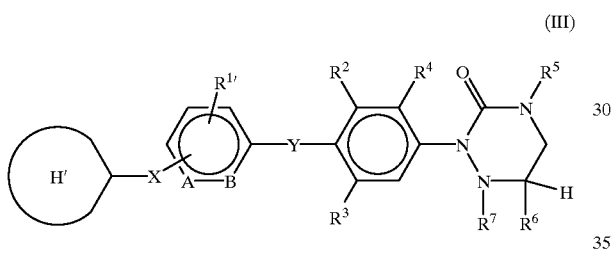

wherein ring H' has the same meaning as defined in [II] above, R$^{1'}$ is a C$_{1-6}$ alkyl group, and the other symbols have the same meanings as defined in [I] above (hereinafter referred to briefly as the compound (III)), or a salt thereof,

[IV] a compound represented by the formula:

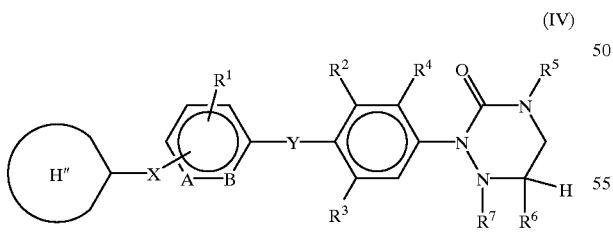

wherein ring H" is a phenyl group which is substituted with one to three substituents selected from the group consisting of a C$_{1-6}$ alkyl group and a C$_{1-6}$ alkylcarbonyl group, and the other symbols have the same meanings as defined in [I] above (hereinafter referred to briefly as the compound (IV)), or a salt thereof, their production and use.

carbonyl group, (vii) a mono- or di-$C_{1-6}$ alkylamino group, (viii) a $C_{1-6}$ alkoxyimino group or (ix) hydroxyimino, (2) halogen, (3) a $C_{1-6}$ alkoxy group, (4) a $C_{1-6}$ alkylidene group, (5) hydroxy, (6) cyano, (7) a carbamoyloxy group which may optionally be substituted with a $C_{1-6}$ alkyl group or a $C_{6-14}$ aryl group, (8) a $C_{1-20}$ acyloxy group, (9) a $C_{1-6}$ alkylsulfonyloxy group and (10) a $C_{6-14}$ arylsulfonyloxy group,

[5] the compound as described in [1] above or a salt thereof, wherein $R^1$ is (1) a hydrogen atom, (2) a halogen atom, (3) a $C_{1-6}$ alkyl group which may optionally be substituted with a substituent selected from the group consisting of (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group and (ix) hydroxyimino, and which may be bonded through a nitrogen atom, an oxygen atom or a sulfur atom or (4) a $C_{1-20}$ acyl group,

[6] the compound as described in [1] above or a salt thereof, wherein $R^2$ and $R^3$ independently represent (1) a hydrogen atom, (2) a halogen atom, or (3) a $C_{1-6}$ alkyl group which may optionally be substituted with a substituent selected from the group consisting of (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group and (ix) hydroxyimino,

[7] the compound as described in [1] above or a salt thereof, wherein $R^5$ is (1) a hydrogen atom, (2) a $C_{1-6}$ alkyl group which may optionally be substituted with a substituent selected from the group consisting of (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group and (ix) hydroxyimino or (3) a $C_{1-20}$ acyl group,

[8] the compound as described in [1] above or a salt thereof, wherein the ring H is a pyridyl group, an oxazolyl group, a thienyl group, a pyrrolyl group, an imidazolyl group, a pyrazolyl group, an indolyl group, an isoquinolyl group, a quinolyl group, a quinoxalinyl group or a $C_{3-14}$ cycloalkyl group, each of which may optionally be substituted with halogen, a $C_{1-6}$ alkylthio group, a $C_{1-6}$ alkyl group which may optionally be substituted with halogen, a benzoyl group, an α-hydroxybenzyl group, a pyrazolyl group, an imidazolyl group, or a triazolyl group; X is (1) —CO—, (2) a methylene group which may optionally be substituted with a substituent selected from the group consisting of (i) hydroxy, (ii) a $C_{1-6}$ alkyl group, (iii) a $C_{1-6}$ alkylidene group and (iv) a $C_{1-6}$ alkoxy group or (3) a single bond; Y is a methylene group or —S—; —A—B— is —CH=CH—; $R^1$ is a hydrogen atom; $R^2$ and $R^3$ are independently a halogen atom or a $C_{1-6}$ alkyl group; $R^4$ is a hydrogen atom; $R^5$ is a hydrogen atom, a $C_{1-6}$ alkyl group or a $C_{1-7}$ alkanoyl group; $R^6$ and $R^7$ form a chemical bond together with each other.

[9] the compound as described in [1] above, which is 2-{4-[4-(6-chloronicotinoyl)-benzyl]-3,5-dichlorophenyl}-4,5-dihydro-1,2,4-triazin-3(2H)-one or a salt thereof,

[10] the compound as described in [1] above, which is 2-{4-[4-((6-chloro-3-pyridyl)hydroxymethyl)benzyl]-3,5-dichlorophenyl}-4,5-dihydro-1,2,4-triazin-3(2H)-one or a salt thereof,

[11] the compound as described in [1] above, which is 2-{4-(4-(6-chloronicotinoyl)benzyl]-3,5-dichlorophenyl}-1,2,4-triazine-3,5(2H,4H)-dione or 2-{4-[4-((6-chloro-3-pyridyl)hydroxymethyl)benzyl]-3,5-dichlorophenyl}-1,2,4-triazine-3,5(2H,4H)-dione, or a salt thereof,

[12] a method for producing of the compound as described in [1] above or a salt thereof, which comprises subjecting a compound of the formula:

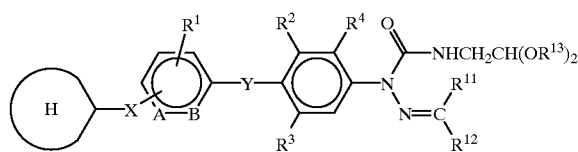

wherein $R^{11}$ is a hydrogen atom or an optionally substituted lower alkyl group; $R^{12}$ is an optionally substituted lower alkyl group or an optionally substituted aryl group; $R^{13}$ is a lower alkyl group; and the other symbols have the same meanings as defined in [1] above; or a salt thereof to a cyclization reaction to provide a compound of the formula:

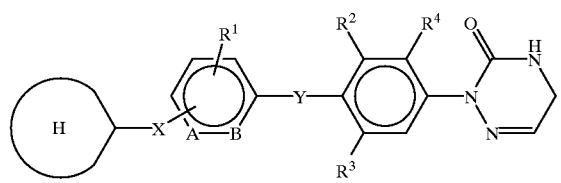

wherein each symbol has the same meaning as defined in [1] above, or a salt thereof, and if necessary, subjecting the resulting compound to an oxidation reaction, a reduction reaction or a substitution reaction,

[13] a compound represented by the formula:

(II)

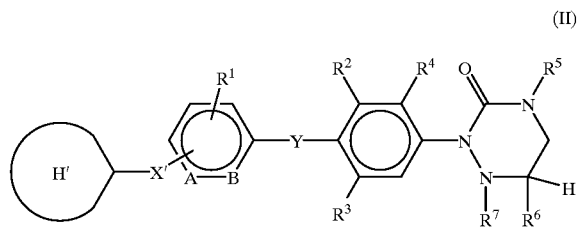

wherein ring H' is a phenyl group which may optionally be substituted with halogen and/or hydroxy; X' is a methylene group which may optionally be substituted with a substituent selected from the group consisting of a $C_{1-6}$ alkyl group and hydroxy; and the other symbols have the same meanings as defined in [1] above, or a salt thereof, namely a compound represented by the formula:

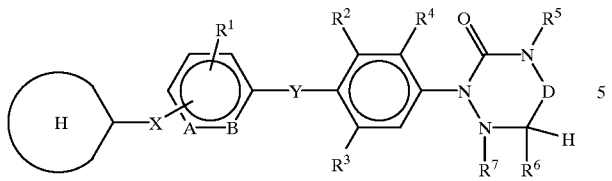

wherein ring H is a phenyl group which may optionally be substituted with halogen and/or hydroxy; X is a methylene group which may optionally be substituted with substituents selected from the group consisting of a $C_{1-6}$ alkyl group and hydroxy; D is —$CH_2$—; and the other symbols have the same meanings as defined in [1] above, or a salt thereof,

[14] a method for producing of the compound as described in [13] above or a salt thereof, which comprises subjecting a compound of the formula:

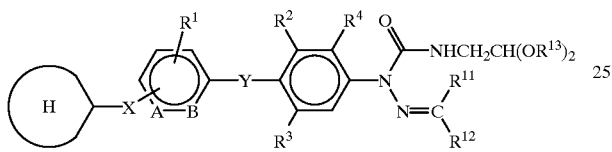

wherein $R^{11}$, $R^{12}$ and $R^{13}$ have the same meanings as defined in [12] above, and the other symbols have the same meanings as defined in [13] above; or a salt thereof to a cyclization reaction to provide a compound of the formula:

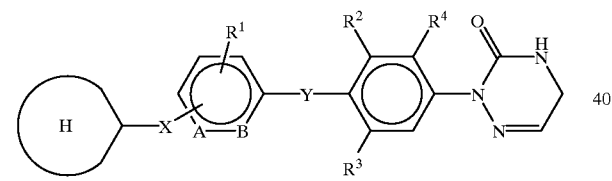

wherein each symbol has the same meaning as defined in [13] above, or a salt thereof, and if necessary, subjecting the resulting compound to a reduction reaction or a substitution reaction,

[15] a compound represented by the formula:

(III)

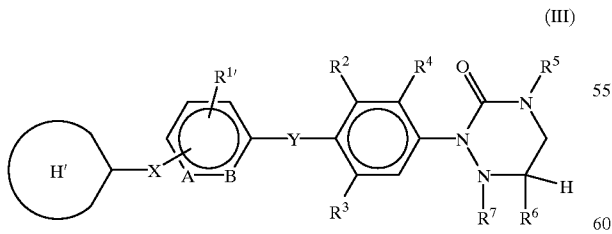

wherein ring H' has the same meaning as defined in [13] above, $R^{1'}$ is a $C_{1-6}$ alkyl group, and the other symbols have the same meanings as defined in [1] above, or a salt thereof, namely a compound represented by the formula:

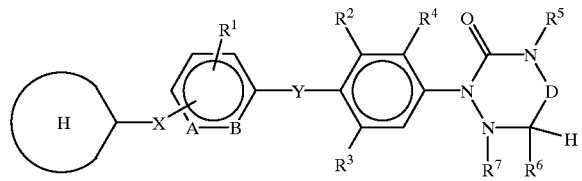

wherein ring H is a phenyl group which may optionally be substituted with halogen and/or hydroxy; $R^1$ is a $C_{1-6}$ alkyl group, D is —$CH_2$—, and the other symbols have the same meanings as defined in [1] above, or a salt thereof,

[16] a method for producing of the compound as described in [15] above or a salt thereof, which comprises subjecting a compound of the formula:

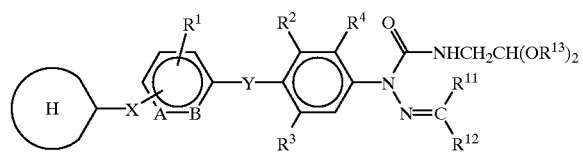

wherein $R^{11}$, $R^{12}$ and $R^{13}$ have the same meanings as defined in [12] above, and the other symbols have the same meanings as defined in [15] above, or a salt thereof to a cyclization reaction to provide a compound of the formula:

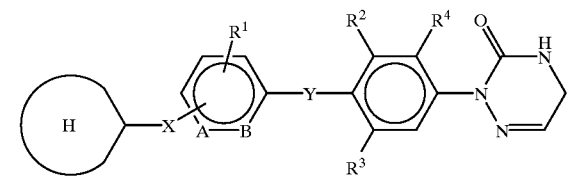

wherein each symbol has the same meaning as defined in [15] above, or a salt thereof, and if necessary, subjecting the resulting compound to a reduction reaction or a substitution reaction,

[17] a compound represented by the formula:

(IV)

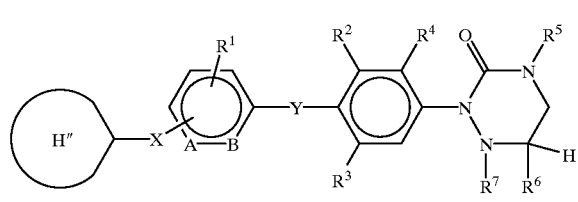

wherein ring H" is a phenyl group which is substituted with one to three substituents selected from the group consisting of a $C_{1-6}$ alkyl group and a $C_{1-6}$ alkyl-carbonyl group; and the other symbols have the same meanings as defined in [1] above, or a salt thereof, namely a compound represented by the formula:

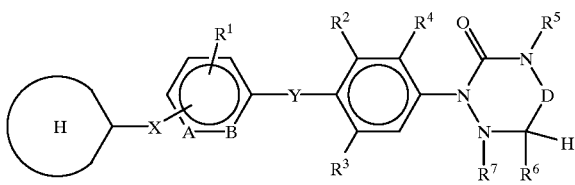

wherein ring H is a phenyl group which is substituted with one to three substituents selected from the group consisting of a $C_{1-6}$ alkyl group and a $C_{1-6}$ alkyl-carbonyl group, D is —$CH_2$—, and the other symbols have the same meanings as defined in [1] above, or a salt thereof,

[18] a method for producing of the compound as described in [17] above or a salt thereof, which comprises subjecting a compound of the formula:

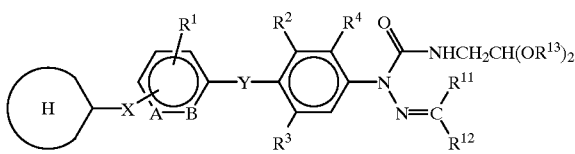

wherein $R^{11}$, $R^{12}$ and $R^{13}$ have the same meanings as defined in [12] above, and the other symbols have the same meanings as defined in [17] above, or a salt thereof to a cyclization reaction to provide a compound of the formula:

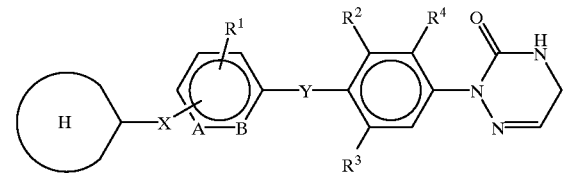

wherein each symbol has the same meaning as defined in [17] above, or a salt thereof, and if necessary, subjecting the resulting compound to a reduction reaction or a substitution reaction,

[19] a composition which comprises a compound as described in [1], [13], [15] or [17] above or a salt thereof and a physiologically acceptable carrier,

[20] use of the compound as described in [1], [13], [15] or [17] above or a salt thereof for the manufacture of an anti-protozoal composition, and

[21] a method for preventing or treating sporozoasis in a vertebrate or an insect which comprises administering an effective amount of the compound as described in [1] above or a salt thereof, to the vertebrate or insect.

BEST MODE FOR CARRYING OUT THE INVENTION

In the above formula, an aromatic heterocyclic group of the optionally substituted aromatic heterocyclic group represented by ring H includes a 5- or 6-membered aromatic heterocyclic group which contains 1 to 4 hetero atoms selected from nitrogen (which may be in the oxide form), oxygen, and sulfur (which may be in the mono- or dioxide form) or a condensed ring group of such a 5- or 6-membered aromatic heterocyclic ring with benzene ring or a 5- or 6-membered aromatic heterocyclic ring which may contain 1 to 4 hetero atoms selected from nitrogen (which may be in the oxide form), oxygen, and sulfur (which may be in the mono- or dioxide form).

Specifically, the 5- or 6-membered aromatic heterocyclic group or the condensed ring group includes pyrrolyl (e.g. 1-, 2- or 3-pyrrolyl), pyrazolyl (e.g. 1-, 3-, 4- or 5-pyrazolyl), imidazolyl (e.g. 1-, 2-, 4- or 5-imidazolyl), triazolyl (e.g. 1,2,3-triazol-1-, 4- or 5-yl, 1,2,4-triazol-1-, 3-, 4- or 5-yl), tetrazolyl (e.g. tetrazol-1-, 2- or 5-yl), furyl (e.g. 2- or 3-furyl), thienyl (e.g. 2- or 3-thienyl), thienyl in which the sulfur atom is oxidized (e.g. 2- or 3-thienyl-1,1-dioxide), oxazolyl (e.g. 2-, 4- or 5-oxazolyl), isoxazolyl (e.g. 3-, 4- or 5-isoxazolyl), oxadiazolyl (e.g. 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g. 2-, 4- or 5-thiazolyl), isothiazolyl (e.g. 3-, 4- or 5-isothiazolyl), thiadiazolyl (e.g. 1,2,3-thiadiazol-4- or 5-yl, 1,2,4-thiadiazol-3- or 5-yl, 1,2,5-thiadiazol-3-yl, 1,3,4-thiadiazol-2-yl), pyridyl (2-, 3- or 4-pyridyl), pyridyl in which the nitrogen atom is oxidized (e.g. 2-, 3- or 4-pyridyl-N-oxide), pyridazinyl (e.g. 3- or 4-pyridazinyl), pyridazinyl in which one or both of the nitrogen atoms are oxidized (e.g. 3-, 4-, 5- or 6-pyridazinyl-N-oxide), pyrimidinyl (e.g. 2-, 4- or 5-pyrimidinyl), pyrimidinyl in which one or both of the nitrogen atoms are oxidized (e.g. 2-, 4-, 5- or 6-pyrimidinyl-N-oxide), pyrazinyl, indolyl (e.g. 3H-indol-2-, 3-, 4-, 5-, 6- or 7-yl), quinolyl (e.g. 2-, 3-, 4-, 5-, 6-, 7- or 8-quinolyl), isoquinolyl (e.g. 1-, 3-, 4-, 5-, 6-, 7- or 8-isoquinolyl), pyrido[2,3-d] pyrimidinyl (e.g. pyrido[2,3-d]pyrimidin-2-yl), naphthyridinyl such as 1,5-, 1,6-, 1,7-, 1,8-, 2,6- or 2,7-naphthyridinyl (e.g. 1,5-naphthyridin-2- or 3-yl), quinoxalinyl (e.g. 2-, 5- or 6-quinoxalinyl), thieno[2,3-d]pyridyl (e.g. thieno[2,3-d] pyridin-3-yl), pyrazinoquinolyl (e.g. pyrazino[2,3-d] quinolin-2-yl), chromenyl (e.g. 2H-chromen-2- or 3-yl), imidazo[1,2-a]pyridyl, imidazo[2,1-b]thiazolyl, imidazo[1, 2-a]pyrimidinyl, imidazo[1,2-b]pyridazinyl, imidazo[1,2-a] imidazolyl, imidazo[2,1-b](1.3.4)thiadiazolyl, pyrazoro[1,5-a]pyrimidinyl, pyrazoro[5,1-b]thiazolyl or pyrazoro[1,5-a] pyridyl.

Among them, a pyridyl, oxazolyl, thienyl, pyrrolyl, imidazolyl, pyrazolyl, indolyl, isoquinolyl, quinolyl or quinoxalinyl group is preferable.

The alicyclic hydrocarbon group includes a $C_{3-14}$ cycloalkyl group (preferably $C_{3-7}$ cycloalkyl group) such as cyclopropyl, cyclobutyl, cyclopentyl, cyclohexyl, perhydronaphthyl, perhydroanthranyl or bicyclo[2,2,1] heptyl, or a $C_{3-14}$ cycloalkenyl group (preferably $C_{3-7}$ cycloalkenyl group) such as cyclopropenyl, cyclobuten-1- or 3-yl, cyclopenten-1-, 3- or 4-yl, cyclohexen-1- or 3-yl.

Among them, a $C_{3-7}$ cycloalkyl group such as cyclohexyl is preferable.

The above-mentioned aromatic heterocyclic group or alicyclic hydrocarbon group may optionally be substituted with one to four substituents selected from the group consisting of hydroxy, amino, cyano, sulfamoyl, sulfamoyloxy, sulfo, mercapto, nitro, oxo, thioxo, halogen, a hydrocarbon group which may optionally be substituted with one to five substituents selected from halogen and hydroxy, a hydrocarbon-oxy group, a hydrocarbon-thio group, a benzoyl group and a 5- or 6-membered heterocyclic group.

The halogen includes fluorine, chlorine, bromine or iodine.

The hydrocarbon group or the hydrocarbon group in the hydrocarbon-oxy group or the hydrocarbon-thio group includes a straight-chain, branched, or cyclic aliphatic hydrocarbon group which may contain a double bond or a triple bond, an aryl group and an aralkyl group. Specifically said hydrocarbon group includes an alkyl group, an alkenyl group, an alkynyl group, an aryl group, and an aralkyl group. Particularly preferred are $C_{1-19}$ hydrocarbon group.

The alkyl group mentioned above is preferably a straight-chain or branched alkyl group of 1 to 6 carbon atoms or cycloalkyl group of 3 to 14 carbon atoms, such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl, cyclohexyl, etc.

The alkenyl group mentioned above is preferably a straight-chain or branched alkenyl group of 2 to 6 carbon atoms or cycloalkenyl group of 3 to 14 carbon atoms including allyl, isopropenyl, isobutenyl, 2-pentenyl, 2-hexenyl, 2-cyclohexenyl, etc.

The alkynyl group mentioned above is preferably an alkynyl group of 2 to 6 carbon atoms, such as propargyl, 2-butynyl, 3-butynyl, 3-pentynyl, 3-hexynyl, etc.

The aryl group mentioned above is preferably an aryl group of 6 to 14 carbon atoms, such as phenyl, naphthyl, anthryl, etc.

The aralkyl group mentioned above is preferably an aralkyl group of 7 to 19 carbon atoms, including phenyl-$C_{1-4}$ alkyl such as benzyl, phenethyl, phenylpropyl; benzhydryl, and trityl.

The 5- or 6-membered heterocyclic group includes a 5- or 6-membered heterocyclic group which contains 1 to 4 hetero atoms selected from nitrogen, oxygen and sulfur such as pyrazolyl (e.g. 1-, 3-, 4- or 5-pyrazolyl), imidazolyl (e.g. 1-, 2-, 4- or 5-imidazolyl) or triazolyl (e.g. 1,2,3-triazol-1-, 4- or 5-yl, 1,2,4-triazol-1-, 3-, 4- or 5-yl).

The ring H is preferably a pyridyl group (e.g. 2-, 3- or 4-pyridyl), an oxazolyl group (e.g. 2-, 4- or 5-oxazolyl) or a cycloalkyl group such as $C_{1-4}$ cycloalkyl group, preferably $C_{3-7}$ cycloalkyl group (e.g. cyclopropyl, cyclobutyl, cyclopentyl, cyclohexyl, perhydronaphthyl, perhydroanthranyl, bicyclo[2,2,1]heptyl, etc.), wherein said group may optionally be substituted with one to three substituents selected from the group consisting of (1) halogen (e.g. fluorine, chlorine, bromine, iodine), (2) a $C_{1-6}$ alkyl group (e.g. methyl, ethyl, n-propyl, isopropyl, n-butyl, isobutyl, sec-butyl or tert-butyl; preferably $C_{1-3}$ alkyl group) which may optionally be substituted with one to five halogen atoms (e.g. fluorine, chlorine, bromine, iodine) and (3) a $C_{1-6}$ alkylthio group (e.g. methylthio, ethylthio, n-propylthio, isopropylthio, n-butylthio, isobutylthio, sec-butylthio or tert-butylthio; preferably $C_{1-3}$ alkylthio group).

Particularly, a pyridyl group (e.g. 2-, 3- or 4-pyridyl) which may optionally be substituted with one to three substituents selected from the group consisting of (1) halogen (e.g. fluorine, chlorine, bromine, iodine), (2) a $C_{1-3}$ alkyl group which may optionally be substituted with one to three halogen atoms such as methyl, trifluoromethyl, 2,2,2-trifluoroethyl and (3) $C_{1-3}$ alkylthio group (e.g. methylthio, ehtylthio, n-propylthio, isopropylthio) is preferable.

The alkyl group as mentioned for $R^8$ includes a straight-chain or branched alkyl group of 1 to 6 carbon atoms such as methyl, ethyl, n-propyl, isopropyl, n-butyl, isobutyl, sec-butyl, tert-butyl, n-pentyl, sec-pentyl, isopentyl, neopentyl, cyclopentyl, n-hexyl, isohexyl or cyclohexyl. Particularly, $C_{1-3}$ alkyl group such as methyl, ethyl, n-propyl or isopropyl is preferable.

The acyl group as mentioned for $R^8$ includes an acyl group of 1 to 20 carbon atoms, which is derived from any organic carboxylic acid. Specifically, mention can be made of an alkanoyl group, preferably a $C_{1-7}$ alkanoyl group (e.g. formyl, acetyl, propionyl, butyryl, isobutyryl, pentanoyl, hexanoyl, heptanoyl, etc.), an arylcarbonyl group, preferably a $C_{6-14}$ arylcarbonyl group (e.g. benzoyl, naphthalenecarbonyl, etc.), an alkoxycarbonyl group, preferably a $C_{1-6}$ alkoxy-carbonyl group (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.), an aryloxycarbonyl group, preferably a $C_{6-14}$ aryloxy-carbonyl group (e.g. phenoxycarbonyl etc.), an aralkylcarbonyl group, preferably a $C_{7-19}$ aralkyl-carbonyl group (e.g. phenyl-$C_{1-4}$ alkylcarbonyl such as benzylcarbonyl, phenethylcarbonyl, phenylpropylcarbonyl; benzhydrylcarbonyl; naphthyl-$C_{1-4}$ alkylcarbonyl such as naphthylethylcarbonyl, etc.), an aralkyloxycarbonyl group, preferably a $C_{7-19}$ aralkyloxycarbonyl (e.g. phenyl-$C_{1-4}$ alkoxycarbonyl such as benzyloxycarbonyl, etc.), a 5- or 6-membered heterocyclic-carbonyl group having 1 to 4 hetero atoms selected from nitrogen (which may be in the oxide form), oxygen, and sulfur (which may be in the mono- or dioxide form) or a condensed heterocycle-carbonyl in which such a 5- or 6-membered heterocyclic ring is condensed with benzene ring or a 5- or 6-membered heterocyclic ring which may contain 1 to 4 hetero atoms selected from nitrogen (which may be in the oxide form), oxygen, and sulfur (which may be in the mono- or dioxide form) (e.g. pyrrolylcarbonyl such as 2- or 3-pyrrolylcarbonyl; pyrazolylcarbonyl such as 3-, 4- or 5-pyrazolylcarbonyl; imidazolylcarbonyl such as 2-, 4- or 5-imidazolylcarbonyl; triazolylcarbonyl such as 1,2,3-triazol-4-ylcarbonyl, and 1,2,4-triazol-3-ylcarbonyl; tetrazolylcarbonyl such as 1H- or 2H-tetrazol-5-ylcarbonyl; furylcarbonyl such as 2- or 3-furylcarbonyl; thienylcarbonyl such as 2- or 3-thienylcarbonyl; oxazolylcarbonyl such as 2-, 4- or 5-oxazolylcarbonyl; isoxazolylcarbonyl such as 3-, 4- or 5-isoxazolylcarbonyl; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, and 1,3,4-oxadiazol-2-ylcarbonyl; thiazolylcarbonyl such as 2-, 4- or 5-thiazolylcarbonyl; isothiazolylcarbonyl such as 3-, 4- or 5-isothiazolylcarbonyl; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, and 1,3,4-thiadiazol-2-ylcarbonyl; pyrrolidinylcarbonyl such as 2- or 3-pyrrolidinylcarbonyl; pyridylcarbonyl such as 2-, 3- or 4-pyridylcarbonyl; pyridylcarbonyl in which the nitrogen atom is oxidized such as 2-, 3- or 4-pyridyl-N-oxidocarbonyl; pyridazinylcarbonyl such as 3- or 4-pyridazinylcarbonyl; pyridazinylcarbonyl in which one or both of nitrogen atoms are oxdiazed such as 3-, 4-, 5- or 6-pyridazinyl-N-oxidocarbonyl; pyrimidinylcarbonyl such as 2-, 4- or 5-pyrimidinylcarbonyl; pyrimidinylcarbonyl in which one or both of the nitrogen atoms are oxidized such as 2-, 4-, 5- or 6-pyrimidinyl-N-oxidocarbonyl; pyrazinylcarbonyl; piperidinylcarbonyl such as 2-, 3- or 4-piperidinylcarbonyl; piperazinylcarbonyl; indolylcarbonyl such as 3H-indol-2- or 3-ylcarbonyl; pyranylcarbonyl such as 2-, 3- or 4-pyranylcarbonyl; thiopyranylcarbonyl such as 2-, 3- or 4-thiopyranylcarbonyl; quinolylcarbonyl such as 3-, 4-, 5-, 6-, 7- or 8-quinolylcarbonyl; isoquinolylcarbonyl; pyrido[2,3-d]pyrimidinylcarbonyl such as pyrido[2,3-d]pyrimidin-2-ylcarbonyl; naphthyridinylcarbonyl such as 1,5-, 1,6-, 1,7-, 1,8-, 2,6- or 2,7-naphthyridinylcarbonyl (e.g. 1,5-naphthyridin-2- or 3-ylcarbonyl); thieno[2,3-d]pyridylcarbonyl such as thieno[2,3-d]pyridin-3-ylcarbonyl); pyrazinoquinolylcarbonyl such as pyrazino[2,3-b]quinolin- 2-ylcarbonyl; chromenylcarbonyl such as 2H-chromen-2- or 3-ylcarbonyl, etc.), and a 5- or 6-membered heterocycle-acetyl group, such as 5- or 6-membered heterocycle-acetyl which contains 1 to 4 hetero atoms selected from nitrogen (which may be in the oxide form), oxygen, and sulfur (which may be in the mono- or dioxide form) such as 2-pyrrolylacetyl, 3-imidazolylacetyl, 5-isoxazolylacetyl, etc.

The substituent for the optionally substituted methylene group as mentioned for X and Y includes (1) an alkyl group such as $C_{1-6}$ alkyl group (e.g. methyl, ethyl, n-propyl, isopropyl; preferably $C_{1-3}$ alkyl group), which may optionally be substituted with one to three substituents selected from the group consisting of hydroxy, an alkylthio group (e.g. $C_{1-4}$ alkylthio group such as methylthio, ethylthio, n-propylthio or isopropylthio), halogen (e.g. fluorine, chlorine, bromine, iodine), an alkoxy group (e.g. $C_{1-6}$ alkoxy group such as methoxy, ethoxy, n-propoxy, tert-butoxy or n-hexyloxy), nitro, an alkoxycarbonyl group (e.g. $C_{1-6}$ alkoxy-carbonyl group such as methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl), an alkylamino group (e.g. mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino or di-(n-butyl)amino), an alkoxyimino group (e.g. $C_{1-6}$ alkoxy-imino group such as methoxyimino, ethoxyimino, n-propoxyimino, tert-butoxyimino or n-hexyloxy-imino) and hydroxyimino, (2) halogen (e.g. fluorine, chlorine, bromine, iodine), (3) an alkoxy group (e.g. $C_{1-6}$ alkoxy group such as methoxy, ethoxy, propoxy or isopropoxy; preferably $C_{1-3}$ alkoxy group), (4) an alkylidene group (e.g. $C_{1-6}$ alkylidene group such as methylene ($CH_2=$), ethylidene, propylidene or isopropylidene; preferably $C_{1-3}$ alkylidene group), (5) hydroxy, (6) cyano, (7) a carbamoyloxy group which may optionally be substituted with one or two substituents selected from the group consisting of a $C_{1-6}$ alkyl group (e.g. methyl, ethyl, n-propyl, isopropyl) and a $C_{6-14}$ aryl group (e.g. phenyl, naphthyl), (8) a $C_{1-20}$ acyloxy group, (9) a $C_{1-6}$ alkylsulfonyloxy group or (10) a $C_{6-14}$ arylsulfonyloxy group.

The $C_{1-20}$ acyloxy group as mentioned above includes an alkanoyloxy group, preferably alkanoyloxy group of 1 to 7 carbon atoms (e.g. formyloxy, acetyloxy, propionyloxy, butyryloxy, isobutyryloxy, pentanoyloxy, hexanoyloxy or heptanoyloxy), an arylcarbonyloxy group, preferably arylcarbonyloxy group of 6 to 14 carbon atoms (e.g. benzoyloxy or naphthalenecarbonyloxy), an alkoxycarbonyloxy group, preferably alkoxy-carbonyloxy group of 1 to 6 carbon atoms (e.g. methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy or tertbutoxycarbonyloxy), an aryloxy-carbonyloxy group, preferably aryloxy-carbonyloxy group of 6 to 14 carbon atoms (e.g. phenoxycarbonyloxy), an aralkylcarbonyloxy group, preferably aralkyl-carbonyloxy group of 7 to 19 carbon atoms (e.g. phenyl-$C_{1-4}$ alkylcarbonyloxy such as benzylcarbonyloxy, phenethylcarbonyloxy, phenylpropylcarbonyloxy; benzhydrylcarbonyloxy; naphthyl-$C_{1-4}$ alkylcarbonyloxy such as naphthylethylcarbonyloxy) or an aralkyloxycarbonyloxy group, preferably aralkyloxy-carbonyloxy group of 7 to 19 carbon atoms (e.g. phenyl-$C_{1-4}$ alkyloxycarbonyloxy such as benzyloxycarbonyloxy).

The $C_{1-6}$ alkylsulfonyloxy group as mentioned above includes methylsulfonyloxy, ethylsulfonyloxy or isopropylsulfonyloxy.

The $C_{6-14}$ arylsulfonyloxy group as mentioned above includes phenylsulfonyloxy or naphthylsulfonyloxy.

The number of the substituents on the methylene group is 1 or 2.

X is preferably (1) —CO—, (2) a methylene group which may optionally be substituted with one or two substituents selected from the group consisting of hydroxy, a $C_{1-6}$ alkyl group (e.g. methyl, ethyl), a $C_{1-6}$ alkylidene group (e.g. methylene, ethylidene) and a $C_{1-6}$ alkoxy group (e.g., methoxy, ethoxy, propoxy), or (3) a single bond.

Y is preferably a methylene group, a methylene group which is substituted with cyano, or a group of —S(O)$_m$— wherein m is 0, 1 or 2. Particularly, a methylene group or —S— is preferable.

As a group of —A—B—, —CH=CH— is especially preferable.

The halogen as mentioned for $R^1$ includes fluorine, chlorine, bromine or iodine.

The alkyl group in the optionally substituted alkyl group which may be bonded through a hetero atom as mentioned for $R^1$ includes the same ones exemplified for alkyl group as mentioned for $R^8$. The hetero atom includes a nitrogen atom, an oxygen atom or a sulfur atom. Such an alkyl group which may be bonded through a hetero atom includes a $C_{1-6}$ alkoxy group (preferably, $C_{1-3}$ alkoxy group) such as methoxy, ethoxy, propoxy or isopropoxy; a $C_{1-6}$ alkylthio group (preferably, $C_{1-3}$ alkylthio group) such as methylthio, ethylthio, propylthio or isopropylthio; or a mono- or di-($C_{1-6}$ alkyl)amino group (preferably, mono- or di-($C_{1-3}$ alkyl) amino group) such as methylamino, ethylamino, propylamino, dimethylamino or diethylamino.

The substituents for the alkyl group which may be bonded through a hetero atom as mentioned above include hydroxy, an alkylthio group (e.g. $C_{1-4}$ alkylthio group such as methylthio, ethylthio, n-propylthio or isopropylthio), halogen (e.g. fluorine, chlorine, bromine, iodine), an alkoxy group (e.g. $C_{1-6}$ alkoxy group such as methoxy, ethoxy, n-propoxy, tert-butoxy or n-hexyloxy), nitro, an alkoxycarbonyl group (e.g. $C_{1-6}$ alkoxy-carbonyl group such as methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl), an alkylamino group (e.g. mono- or di-$C_{1-6}$ alkylamino group such as methylamino, ethylamino, n-propylamino, n-butylamino, tert-butylamino, n-pentylamino, n-hexylamino, dimethylamino, diethylamino, methylethylamino, di-(n-propyl)amino or di-(n-butyl)amino), an alkoxyimino group (e.g. $C_{1-6}$ alkoxyimino group such as methoxyimino, ethoxyimino, n-propoxyimino, tert-butoxyimino or n-hexyloxyimino) and hydroxyimino. The number of the substituents is 1 to 3.

The acyl group as mentioned for $R^1$ includes the same ones as exemplified for the acyl group as mentioned for $R^8$.

Among them, $R^1$ is preferably a hydrogen atom or a $C_{1-6}$ alkyl group (e.g. methyl, ethyl, n-propyl, isopropyl, n-butyl, isobutyl, sec-butyl, tert-butyl, n-pentyl, sec-pentyl, isopentyl, neopentyl, n-hexyl or isohexyl; especially preferred is a $C_{1-3}$ alkyl group). Particularly, a hydrogen atom is preferable.

The halogen as mentioned for $R^2$ or $R^3$ includes fluorine, chlorine, bromine or iodine.

The optionally substituted alkyl group as mentioned for $R^2$ or $R^3$ includes an alkyl group (e.g. $C_{1-6}$ alkyl group such as methyl, ethyl, n-propyl or isopropyl; preferably $C_{1-3}$ alkyl group) which may optionally be substituted with one to three substituents selected from the group consisting of hydroxy, an alkylthio group (e.g. $C_{1-4}$ alkylthio group such as methylthio, ethylthio, n-propylthio or isopropylthio), halogen (e.g. fluorine, chlorine, bromine, iodine), an alkoxy group (e.g. $C_{1-6}$ alkoxy group such as methoxy, ethoxy, n-propoxy, tert-butoxy or n-hexyloxy), nitro, an alkoxycarbonyl group (e.g. $C_{1-6}$ alkoxy-carbonyl group such as methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl), an alkylamino group (e.g. mono- or di-$C_{1-6}$ alkylamino group such as methylamino, ethylamino, n-propylamino, n-butylamino, tertbutylamino, n-pentylamino, n-hexylamino, dimethylamino, diethylamino, methylethylamino, di-(n-propyl)amino or di-(n-butyl)amino), an alkoxyimino group (e.g. $C_{1-6}$ alkoxyimino group such as methoxyimino, ethoxyimino, n-propoxyimino, tert-butoxyimino or n-hexyloxyimino) and hydroxyimino.

$R^2$ is preferably halogen or a $C_{1-6}$ alkyl group. Particularly, halogen is preferable.

$R^3$ is preferably halogen.

The halogen as mentioned for $R^4$ includes fluorine, chlorine, bromine or iodine.

$R^4$ is preferably a hydrogen atom.

The optionally substituted alkyl group as mentioned for $R^5$ includes the same ones exemplified for the optionally substituted alkyl group as mentioned for $R^2$ or $R^3$.

The acyl group as mentioned for $R^5$ includes the same ones exemplified for the acyl group as mentioned for $R^8$.

$R^5$ is preferably a hydrogen atom, a $C_{1-6}$ alkyl group (e.g. methyl, ethyl, n-propyl, isopropyl, n-butyl, isobutyl, sec-butyl, tert-butyl, n-pentyl, sec-pentyl, isopentyl, neopentyl, n-hexyl or isohexyl; particularly preferred is a $C_{1-3}$ alkyl group) or a $C_{1-7}$ alkanoyl group (e.g. formyl, acetyl, propionyl, butyryl, isobutyryl, pentanoyl, hexanoyl or heptanoyl). Particularly preferred is a hydrogen atom.

$R^6$ and $R^7$ preferably form a chemical bond together with each other. Namely, as a group of the formula:

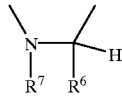

, a group of the formula:

is preferable.

D is preferably —$CH_2$—.

In the formula mentioned above, a ring H' represents a phenyl group which may optionally be substituted with halogen atom(s) and/or hydroxy.

The halogen includes fluorine, chlorine, bromine or iodine. The number of the substituent on the phenyl group is one to three.

X' represents a methylene group which may optionally be substituted with one or two substituents selected from the group consisting of a $C_{1-6}$ alkyl group and hydroxy. The $C_{1-6}$ alkyl group includes methyl, ethyl, n-propyl or isopropyl. Among them, a $C_{1-3}$ alkyl group, especially methyl is preferable.

In the formula mentioned above, the $C_{1-6}$ alkyl group as mentioned for $R^{1'}$ includes the same ones exemplified for the alkyl group which is mentioned as the substituent on the methylene group as above-mentioned for X'.

In the formula mentioned above, the ring H" represents a phenyl group which is substituted with substituents selected from a $C_{1-6}$ alkyl group and a $C_{1-6}$ alkyl-carbonyl group. The $C_{1-6}$ alkyl group includes the same ones exemplified for the alkyl group which is mentioned as the substituent on the methylene group as above-mentioned for X'. The $C_{1-6}$ alkyl-carbonyl group includes acetyl, propionyl, butyryl or isobutyryl. The number of the $C_{1-6}$ alkyl group or $C_{1-6}$ alkyl-carbonyl group as the substituents is 1 to 3.

Of the compounds (I) to (VI) of the present invention, compound (I) is preferred.

Salts of the compounds (I) to (VI) include physiologically acceptable salts, e.g., alkali metal salts such as sodium salts and potassium salts; alkaline earth metal salts such as calcium salts; inorganic acid salts such as phosphates and nitrates; and acetates, oxalates, and succinates.

The compounds (I) to (IV) can be produced according to the following process.

Reaction a)

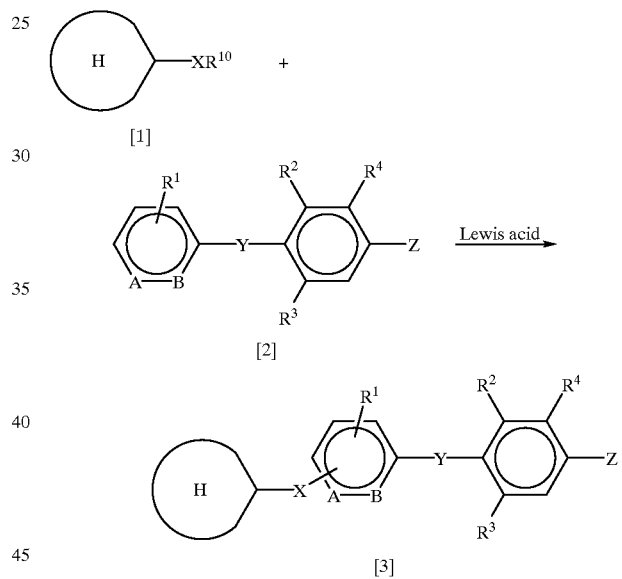

wherein $R^{10}$ represents hydroxy or halogen; Z represents nitro or amino which may has a protective group; and the other symbols have the same meaning as defined above.

Reaction a) is a reaction wherein nitrobenzene or aniline derivative [2] is subjected to an acylating reaction with, for example, acylating agent [1], to yield reaction intermediate [3].

Useful amino group-protecting group include (1) formyl, (2) $C_{1-6}$ alkylcarbonyl groups, e.g., acetyl, ethylcarbonyl, propylcarbonyl, and butylcarbonyl, which may be substituted by 1 to 3 substituents, such as halogen atoms, e.g., fluorine, chlorine, and bromine, (3) $C_{6-10}$ arylcarbonyl groups, e.g., phenylcarbonyl, which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups, (4) $C_{1-6}$alkyloxycarbonyl groups, e.g., methoxycarbonyl and ethoxycarbonyl, which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups, (5) $C_{6-10}$ aryloxycarbonyl groups, e.g., phenyloxycarbonyl, which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups, (6) $C_{7-19}$ aralkyl-carbonyl groups, e.g., phenyl-$C_{1-3}$ alkylcarbonyls such as benzylcarbonyl and phenylethylcarbonyl, benzhydrylcarbonyl, and tritylcarbonyl, which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups, (7) trityl groups which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups, and (8) phthaloyl groups which may have 1 to 3 substituents selected from halogen atoms, e.g., fluorine, chlorine, and bromine, $C_{1-6}$ alkyl-carbonyls, e.g., methylcarbonyl, ethylcarbonyl, propylcarbonyl, and butylcarbonyl, and nitro groups; any group can be used, as long as it can be converted to an amino group under chemical or physiological conditions (e.g., by enzymatic degradation or via metabolic pathway in vivo).

Such acylating agents include, for example, benzoyl chloride and nicotinoyl chloride.

This reaction is normally carried out in the presence or absence of an inert solvent, and may be carried out in the presence of a Lewis acid. The reaction temperature is normally about $-10°$ C. to $100°$ C., preferably $40°$ C. to $80°$ C. For this reaction, almost all inert organic solvents can be used, including solvents in common use for organic synthetic reactions, e.g., aliphatic or aromatic hydrocarbons (e.g., ligroin, benzine, nitrobenzene), halogenated hydrocarbons (e.g., methylene chloride, ethylene chloride, chloroform, carbon tetrachloride, dichloroethane), and carbon disulfide.

Useful Lewis acids include, for example, $AlCl_3$, $AlBr_3$, $FeCl_3$, tetrachlorobis(tetrahydrofuran)hafnium and $BF_3.OEt_2$.

Reaction b)

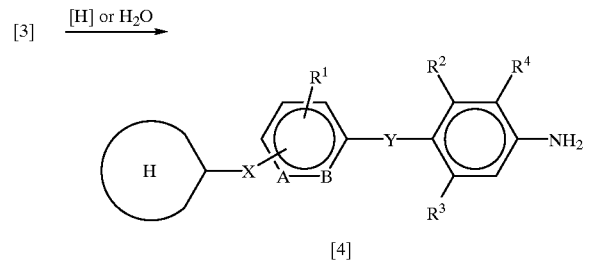

[4]

wherein the respective symbols have the same meanings as defined above.

Intermediate [3] can be derivatized to intermediate [4] by a reducing or hydrolyzing reaction.

When compound [3] has a nitro group for Z, it can be derivatized to a constant amount of compound [4] by an ordinary reducing reaction, e.g., catalytic reduction or Béchamp reduction [Shin Jikken Kagaku Koza, Vol. 15(II), Maruzen (1977)].

When Z is an amino group protected by a protecting group as described above, compound [4] can be derivatized to compound [4] at high recovery rates by, for example, an ordinary hydrolytic reaction using an acid or base [Shin Jikken Kagaku Koza, Vol. 14(V), Maruzen (1987)].

Reaction c)

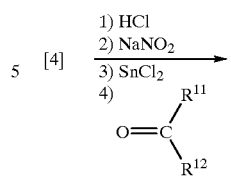

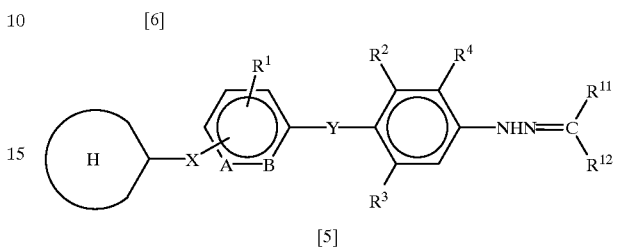

wherein $R^{11}$ represents a hydrogen atom or an optionally substituted lower alkyl group; $R^{12}$ represents an optionally substituted lower alkyl group or an optionally substituted $C_{6-14}$ aryl group such as a phenyl group; and the other symbols have the same meaning as defined above.

The lower alkyl group of the optionally substituted lower alkyl group for $R^{11}$ includes $C_{1-4}$ alkyl groups such as methyl, ethyl, n-propyl, isopropyl, n-butyl, isobutyl, sec-butyl, and tert-butyl.

Substituents for said lower alkyl group include $C_{1-4}$ alkylthio groups (e.g., methylthio, ethylthio), halogens (e.g., fluorine, chlorine, bromine, iodine), $C_{1-6}$ alkoxy groups (e.g., methoxy, ethoxy, propoxy), nitro, $C_{1-6}$ alkoxycarbonyl groups (e.g., methoxycarbonyl, ethoxycarbonyl, propoxycarbonyl), mono- or di-$C_{1-6}$ alkylamino groups (e.g., methylamino, ethylamino, dimethylamino), $C_{1-6}$ alkoxyimino groups (e.g., methoxyimino), and hydroxyimino group. The number of such substituents is preferably 1 to 3.

Substituents for said aryl group include (1) $C_{1-6}$ alkyl groups (e.g., methyl, ethyl), (2) $C_{2-6}$ alkenyl groups (e.g., allyl, isopropenyl, isobutenyl), (3) $C_{2-6}$ alkynyl groups (e.g., propargyl, 2-butynyl, 3-butynyl), (4) $C_{1-6}$ alkoxy groups (e.g., methoxy, ethoxy), (5) acyl groups such as $C_{1-7}$ alkanoyl groups (e.g., formyl, acetyl, propionyl), $C_{6-14}$ arylcarbonyl groups (e.g., benzoyl), $C_{1-6}$ alkoxy-carbonyl groups (e.g., methoxycarbonyl), $C_{6-14}$ aryloxy-carbonyl groups (e.g., phenoxycarbonyl), $C_{7-19}$ aralkyl-carbonyl groups (e.g., phenyl-$C_{1-2}$ alkyl-carbonyl groups such as benzylcarbonyl), and $C_{7-19}$ aralkyloxycarbonyl groups (e.g., benzyloxycarbonyl), (6) nitro, (7) amino, (8) hydroxy, (9) cyano, (10) sulfamoyl, (11) mercapto, (12) halogens, and (13) $C_{1-4}$ alkylthio groups (e.g., methylthio, ethylthio). The number of such substituents is preferably 1 to 3.

The reaction process for the production of hydrazone derivative [5] from compound [4] is normally carried out in an acidic aqueous or nonaqueous solution of acetic acid etc. under ordinary diazotizing reaction conditions. Specifically, the reaction temperature is normally $-5°$ C. to $30°$ C., preferably $5°$ C. to $15°$ C. Reaction time is normally about 20 minutes to 5 hours, preferably 30 minutes to 2 hours.

The amount of concentrated hydrochloric acid used relative to aniline derivative [4] is normally 2.0 to 50.0 moles, preferably 3.0 to 20.0 moles. The amount of sodium nitrite used is normally 1.0 to 3.0 moles, preferably 1.0 to 1.3 moles. The amount of $SnCl_2$ used is normally 2.0 to 5.0 moles, preferably 2.0 to 3.0 moles.

The amount of carbonyl derivative [6] relative to the aniline derivative is normally 1.0 to 2.0 moles, preferably 1.0 to 1.2 moles.

With respect to reaction c), it is also possible to derivatize compound [4] to compound [5] by reaction with carbonyl derivative [6] after being converted to a hydrazine derivative by an ordinary reaction and isolated as a free compound or a hydrochloride thereof (intermediate [7]).

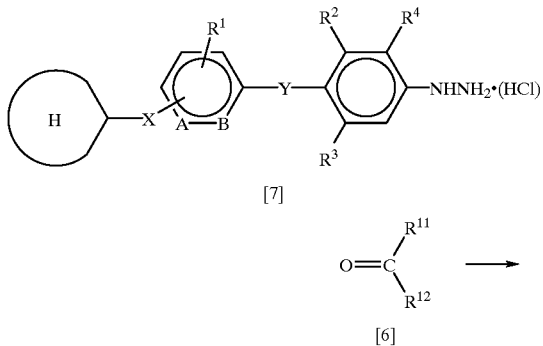

wherein the respective symbols have the same meanings as defined above.
Reaction d)

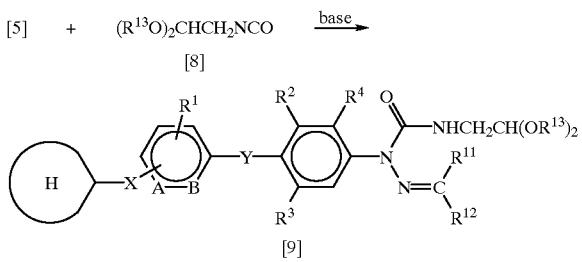

wherein $R^{13}$ represents a lower alkyl group, and the other symbols have the same meanings as defined above.

The lower alkyl group for $R^{13}$ is exemplified by $C_{1-3}$ alkyl groups such as methyl, ethyl, propyl, and isopropyl.

The reaction for the production of semicarbazone derivative [9], an intermediate, by reacting hydrazone derivative [5] as produced by the above-described reaction with 2,2-dialkoxyethyl isocyanate [8], is normally carried out in the presence or absence of an inert solvent, and may be carried out in the presence of a base. It depends on the kind of solvent used for the reaction, but the reaction temperature is normally about –20° C. to 110° C., preferably about 0° C. to 50° C. Also it depends on the kind of solvent used for the reaction, but the reaction time is normally about 10 minutes to 5 hours, preferably 30 minutes to 2 hours.

For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, diisopropyl ether, dibutyl ether, glycol dimethyl ether, diglycol dimethyl ether, tetrahydrofuran, dioxane), ketones (e.g., acetone, methyl ethyl ketone, methyl isopropyl ketone), esters (e.g., ethyl acetate ester), nitriles (e.g., acetonitrile, propionitrile), amides (e.g., dimethylformamide, dimethylacetamide, triamide hexamethylphosphate), dimethyl sulfoxide, and pyridine.

The amount of 2,2-dialkoxyethyl isocyanate [8] used relative to hydrazone derivative [5] is normally 1.0 to 3.5 moles, preferably 1.0 to 1.5 moles.

The bases used to facilitate the reaction include, for example, inorganic bases such as sodium carbonate, potassium carbonate, calcium carbonate, sodium hydroxide, and potassium hydroxide; and organic bases such as triethylamine, pyridine, dimethylaniline, picoline, 1,5-diazabicyclo[4,3,0]non-5-ene, 1,4-diazabicyclo[2,2,2]octane, and 1,8-diazabicyclo[5,4,0]undec-7-ene (DBU). The amount of base used relative to starting material [5] is normally 0.001 to 30.0%, preferably 0.01 to 5.0%.

Reaction e)

Semicarbazone derivative [9] as synthesized by the above-described reaction is converted to 2-substituted-1,2,4-triazin-3-one derivative [10] by a cyclizing reaction process.

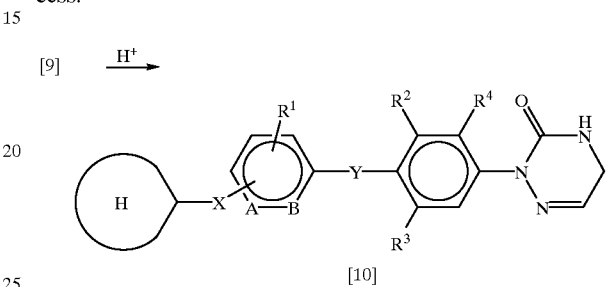

wherein the respective symbols have the same meanings as defined above.

This reaction is normally carried out in an inert solvent or in the absence thereof, and nay be carried out in the presence of an acid. It depends on the kind of solvent used for the reaction, but the reaction temperature is normally about –20° C. to 150° C., preferably about 0° C. to 50° C. Also it depends on the kind of solvent used for the reaction, but the reaction time is normally about 10 minutes to 5 hours, preferably 30 minutes to 2 hours.

For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, diisopropyl ether, dibutyl ether, glycol dimethyl ether, diglycol dimethyl ether, tetrahydrofuran, dioxane), ketones (e.g., acetone, methyl ethyl ketone, methyl isopropyl ketone, methyl isobutyl ketone), esters (e.g., ethyl acetate ester), nitrites (e.g., acetonitrile, propionitrile), amides (e.g., dimethylformamide, dimethylacetamide, triamide hexamethylphosphate), alcohols (e.g., methyl alcohol, ethyl alcohol, propyl alcohol, isopropyl alcohol), pyridine, and dimethyl sulfoxide.

Acids used to facilitate this reaction include, for example, trichloroacetic acid, trifluoroacetic acid, p-toluenesulfonic acid, trifluoroborane etherate, methanesulfonic acid, sulfuric acid, hydrochloric acid, phosphoric acid, and polyphosphoric acid.

The desired 1,2,4-triazin-3-one derivative [10] can also be obtained at high recovery rates by subjecting the reaction mixture obtained in the above-described reaction d) directly to a cyclizing reaction, without isolating semicarbazone derivative [9] from the reaction mixture. Such a series of processes (one-pot reaction) is preferably used in industrial production of desired compound [10] and derivatives therefrom (e.g., compounds [11], [12], [13], [14], [15] described below).

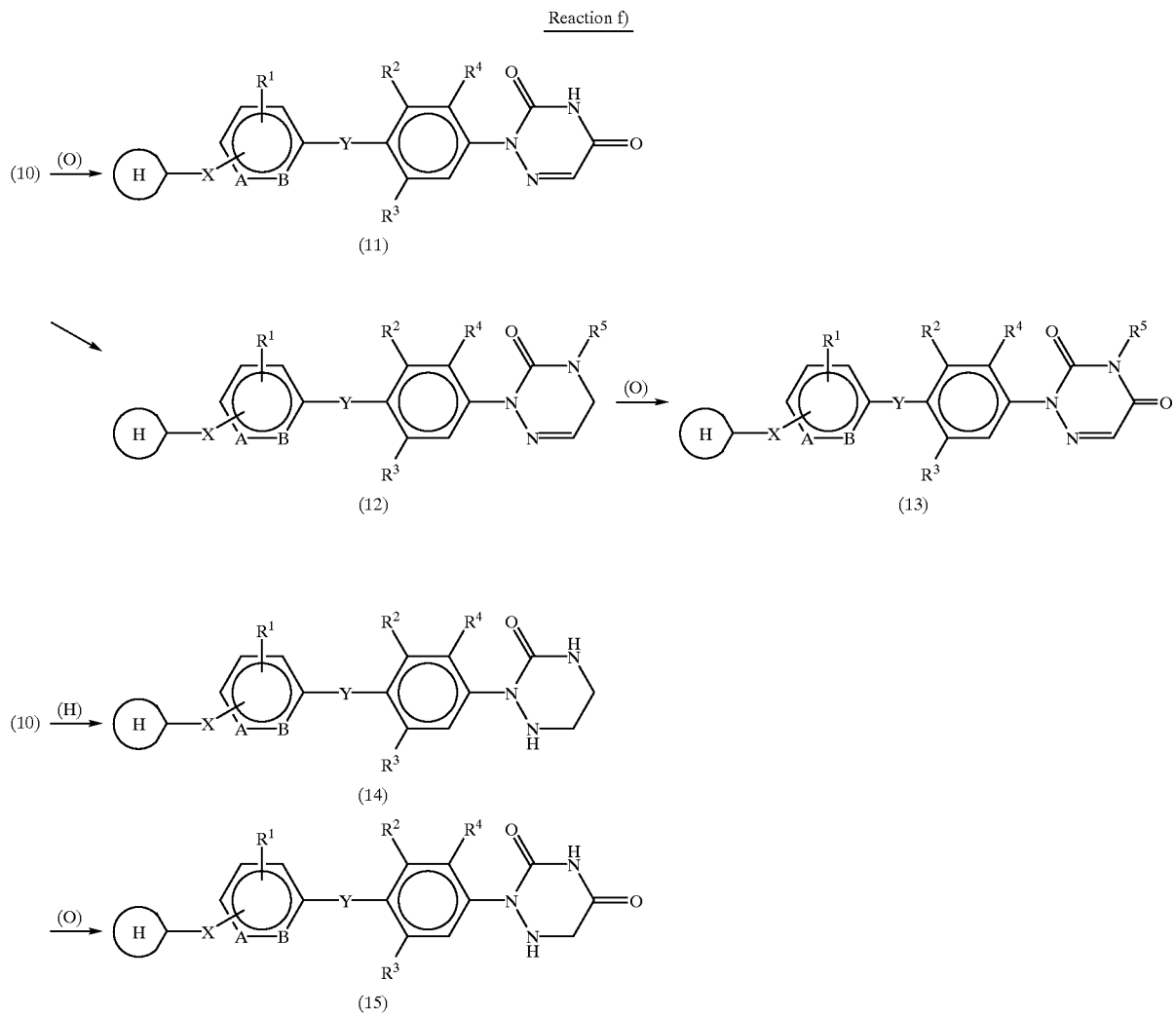

Reaction f)

wherein the respective symbols have the same meanings as defined above.

Compound [10] as obtained by this production method is subjected to an oxidation reaction by a conventional method to yield compound [11].

This oxidation reaction is normally carried out in the presence or absence of an inert solvent, and the reaction temperature being normally about −20° C. to about 110° C., preferably about 0° C. to 50° C.

For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, diisopropyl ether, dibutyl ether, glycol dimethyl ether, diglycol dimethyl ether, tetrahydrofuran, dioxane), ketones (e.g., acetone, methyl ethyl ketone, methyl isopropyl ketone, methyl isobutyl ketone), esters (e.g., ethyl acetate ester), nitriles (e.g., acetonitrile, propionitrile), amides (e.g., dimethylformamide, dimethylacetamide, triamide hexamethylphosphate), dimethyl sulfoxide, and pyridine.

Said oxidation reaction is carried out using an appropriate oxidant. Such oxidants include permanganates, chromic acid, chromium trioxide, pyridinium chlorochromate, mercury (II) acetate, oxygen, ozone, hydrogen peroxide, organic peracids (e.g., perbenzoic acid, metachloroperbenzoic acid, monoperoxyphthalic acid, performic acid, peracetic acid, trifluoroperacetic acid). The amount of oxidant used is normally 1.0 to 5.0 moles, preferably 1.0 to 3.5 moles, relative to starting compound [10].

Furthermore, compound [12] can be produced by subjecting compound [10] to an alkylating or acylating reaction.

Specifically, it is possible to achieve alkyl substitution by reacting compound [10] with an alkyl halide in the presence of a sodium halide, sodium methoxide, sodium ethoxide, or the like, and to achieve acyl substitution by reacting compound [10] with an acyl halide or an acid anhydride.

Compound [13] can be obtained by subjecting compound [12] thus obtained to the above-described oxidation reaction.

Compound [10] can further derivatized to compound [14] by a commonly known reduction reaction, which may be further subjected to the above-described oxidation reaction to yield compound [15].

If desired, compound [10] can be derivatized to various physiologically acceptable salts, e.g., alkali metal salts such as sodium salts and potassium salts, alkaline earth metal salts such as calcium salts, inorganic acid salts such as phosphates and nitrates, and organic acid salts such as acetates, oxalates, and succinate, by conventional methods.

Reaction g)

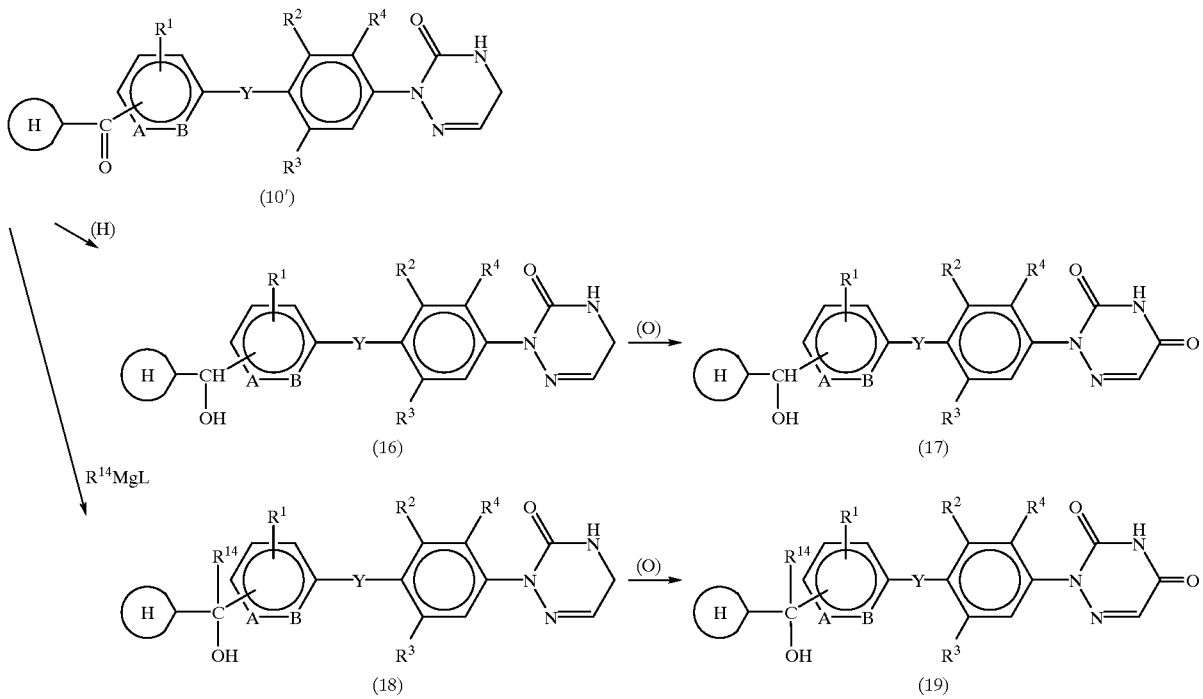

wherein $R^{14}$ represents an alkyl group [e.g., $C_{1-6}$ alkyl groups (preferably $C_{1-3}$ alkyl groups) such as methyl, ethyl, n-propyl, and isopropyl] which may optionally be substituted by 1 to 3 substituents selected from alkylthio groups (e.g., $C_{1-4}$ alkylthios such as methylthio, ethylthio, n-propylthio, isopropylthio), alkoxy groups (e.g., $C_{1-6}$ alkoxys such as methoxy, ethoxy, n-propoxy, tert-butoxy, and n-hexyloxy), nitro, alkylamino groups (e.g., di-$C_{1-6}$ alkylaminos such as dimethylamino, diethylamino, methylethylamino, di-n-propylamino, and di-n-butylamino) and alkoxyimino groups (e.g., $C_{1-6}$ alkoxyiminos such as methoxyimino, ethoxyimino, n-propoxyimino, tert-butoxyimino, and n-hexyloxy-imino); L represents a halogen atom (e.g., fluorine, chlorine, bromide, iodine); the other symbols have the same meanings as defined above.

Following reaction processes a) through e) above, a triazine derivative having —CO— for X (compound [10']), for example, is obtained.

Triazine derivative [10'] can be derivatized to compound [16], which has a methylene group substituted by hydroxy, for X, by a commonly known reduction reaction, which may be further subjected to the above-described oxidation reaction to yield compound [17].

Also, by subjecting triazine derivative [10'] above to an ordinary process of the Grignard reaction to yield compound [18], which may be further subjected to the above-described oxidation reaction to yield compound [19].

By reacting compound [16] or compound [18] with an alkylating agent (e.g., methyl halides, ethyl halides, isopropyl halides), for example, a triazine derivative having an alkoxy group added to the methylene group for X can be obtained.

By reacting compound [16] or compound [18] with an acylating agent (e.g., acetyl chloride, acetic anhydride, benzoyl chloride), for example, a triazine derivative having an acyloxy group added to the methylene group for X can be obtained.

By reacting compound [16] or compound [18] with a carbamoylating agent (e.g., isocyanate derivatives such as methyl isocyanate, ethyl isocyanate, and phenyl isocyanate, or carbamoyl chlorides such as N,N-dimethylcarbamoyl chloride and phenylcarbamoyl chloride), for example, a triazine derivative that has a carbamoyloxy group which may be substituted by 1 or 2 $C_{1-6}$ alkyl groups (e.g., methyl, ethyl, n-propyl, isopropyl) or $C_{6-14}$ aryl groups (e.g., phenyl groups, naphthyl groups), and that is added to the methylene group for X, can be obtained.

By reacting compound [16] or compound [18] with a sulfonylating agent (e.g., methanesulfonyl chloride, phenylsulfonyl chloride), for example, a triazine derivative having a $C_{1-6}$ alkylsulfonyloxy group or a $C_{6-14}$ arylsulfonyloxy group added to the methylene group for X can be obtained.

The above-described reaction of compound [16] or compound [18] with an alkylating agent, acylating agent, carbamoylating agent or sulfonylating agent is normally carried out in an inert solvent or in the absence thereof, and may be carried out in the presence of a base. It depends on the kind of solvent used for the reaction, but the reaction temperature is normally about −20° C. to 80° C., preferably about 0° C. to 50° C. Also it depends on the kind of solvent used for the reaction, but the reaction time is normally about 10 minutes to 5 hours, preferably 30 minutes to 2 hours.

For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, diisopropyl ether, dibutyl ether, glycol dimethyl ether, diglycol dimethyl ether, tetrahydrofuran, dioxane), ketones (e.g., acetone, methyl ethyl ketone, methyl isopropyl ketone, methyl isobutyl ketone), esters (e.g., ethyl acetate ester), nitrites (e.g., acetonitrile, propionitrile), amides (e.g., dimethylformamide, dimethylacetamide, triamide hexamethylphosphate), dimethyl sulfoxide, and pyridine.

The amount of alkylating agent, acylating agent, carbamoylating agent or sulfonylating agent used is normally 1.0 to 3.5 moles, preferably 1.0 to 1.5 mole.

Bases used to facilitate the reaction include, for example, inorganic bases such as sodium carbonate, potassium carbonate, calcium carbonate, sodium hydroxide, and potassium hydroxide; and organic bases such as triethylamine, pyridine, dimethylaniline, picoline, 1,5-diazabicyclo[4,3,0]non-5-ene, 1,4-diazabicyclo[2,2,2]octane, and 1,8-diazabicyclo[5,4,0]undec-7-ene (DBU). The amount of base used relative to starting compound [16] or [18] is normally 1.0 to 3.0 moles, preferably 1.0 to 2.0 moles.

By reacting compound [16] or compound [18] with a halogenating agent, for example, a triazine derivative having a halogen added to the methylene group for X can be obtained.

This reaction is normally carried out in the presence or absence of an inert solvent, and may be carried out in the presence of an acid. It depends on the kind of solvent used for the reaction, but the reaction temperature is normally about −20° C. to 80° C., preferably about 0° C. to 40° C. Also it depends on the kind of solvent used for the reaction, but the reaction time is normally about 10 minutes to 5 hours, preferably 30 minutes to 2 hours.

For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, diisopropyl ether, dibutyl ether, glycol dimethyl ether, diglycol dimethyl ether, tetrahydrofuran, dioxane), nitrites (e.g., acetonitrile, propionitrile), amides (e.g., dimethylformamide, dimethylacetamide, triamide hexamethylphosphate), and dimethyl sulfoxide. Halogenating agents useful for this reaction include, for example, hydrogen halides such as hydrogen chloride and hydrogen bromide, thionyl chloride, thionyl bromide, N-chlorosuccinimide, N-bromosuccinimide, and diethylaminosulfate trifluoride. The amount of halogenating agent used is normally 1.0 to 3.5 moles, preferably 1.0 to 1.5 mole, relative to compound [16] or compound [18].

Also, a reaction promoter such as triphenylphosphine may be used to facilitate the reaction.

A triazine derivative having an alkylidene group added to the methylene group for X can be obtained by subjecting compound [18] to a dehydrating reaction in the presence or absence of, for example, boron trifluoride dimethyl ether complex.

Reaction h)

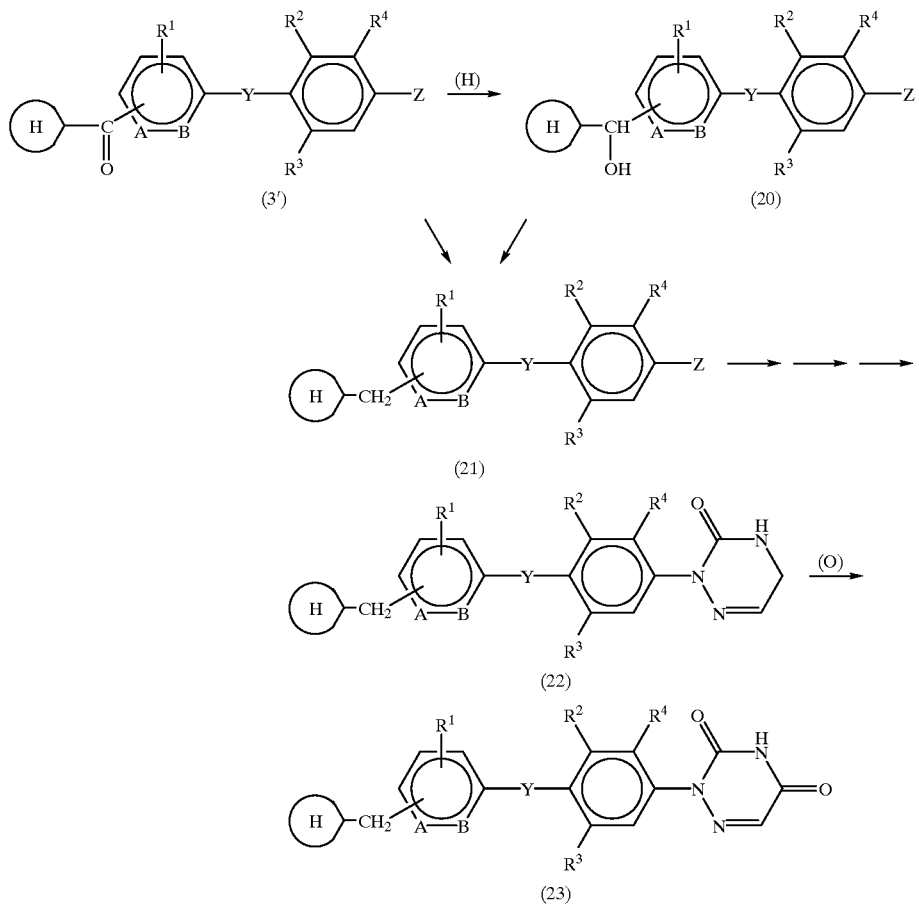

wherein the respective symbols have the same meanings as defined above.

Compound [3'], which has —CO— for X, can be derivatized to intermediate [20] or [21] by a commonly known method of reduction. Compound [21] can be derivatized to compound [22] by the same procedures as reaction processes b) through e) above, which may be further subjected to the above-described oxidation reaction to yield compound [23] (Shin Jikken Kagaku Koza, Vol. 15(II), Maruzen (1977)].

Reaction i)

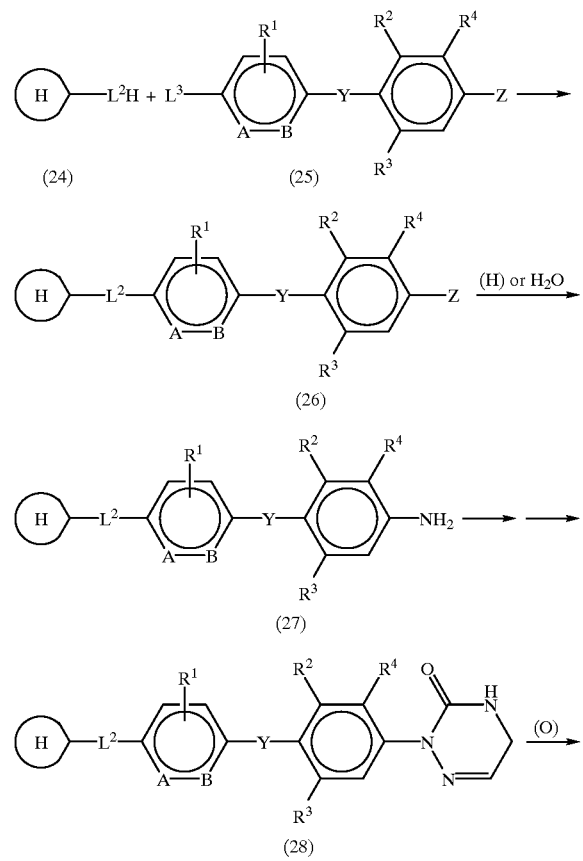

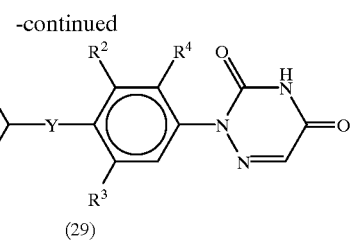

wherein $L^2$ represents —O—, a group of the formula —S(O)$_m$— wherein m represents 0, 1 or 2) or a group of the formula —NR$^8$ wherein R$^8$ has the same meaning as defined above); $L^3$ represents a halogen atom or a group of —OSO$_2$R$^{16}$ wherein R$^{16}$ represents an alkyl group or phenyl group which may optionally be substituted; the other symbols have the same meanings as defined above.

The halogen atom for $L^3$ is exemplified by fluorine, chlorine, bromine, and iodine.

The alkyl group for R$^{16}$, which may be substituted, includes the same alkyl groups as those mentioned to exemplify the optionally substituted alkyl group for R$^2$ or R$^3$ above.

In the above-described reaction processes, intermediate [26] can be produced using as a reaction promoter a base such as sodium methoxide, sodium ethoxide, NaOH, KOH, NaHCO$_3$, triethylamine, pyridine, or 1,8-diazabicyclo[5,4,0]undec-7-ene (DBU).

Reaction temperature is normally about −10° C. to 100° C., preferably about 20° C. to 60° C. For this reaction, almost all inert organic solvents can be used, including solvents in common use for organic synthetic reactions, e.g., aliphatic or aromatic hydrocarbons (e.g., benzene, ligroin, benzine, toluene, xylene), halogenated hydrocarbons (e.g., methylene chloride, ethylene chloride, chloroform, carbon tetrachloride, dichloroethane, chlorobenzene, o-dichlorobenzene), ethers (e.g., diethyl ether, glycol dimethyl ether, diglycol dimethyl ether, tetrahydrofuran, dioxane), ketones (e.g., acetone, methyl ethyl ketone, methyl isopropyl ketone, methyl isobutyl ketone), esters (e.g., ethyl acetate), nitriles (e.g., acetonitrile, propionitrile), amides (e.g., dimethylformamide, dimethylacetamide, triamide hexamethylphosphate), N-methylpyrrolidone, dimethyl sulfoxide, and tetramethylenesulfone.

Intermediate [26] can be derivatized to compound [28] or [29] via intermediate [27] by the same production processes as reactions b) through f) above.

The compound of the present invention can also be produced by the method described below.

Reaction j)

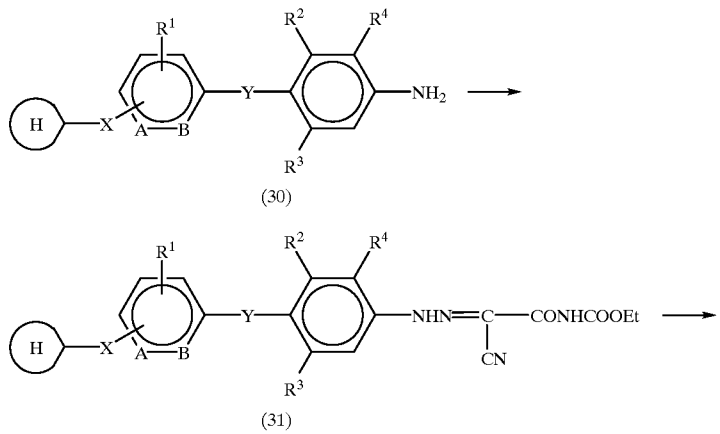

-continued

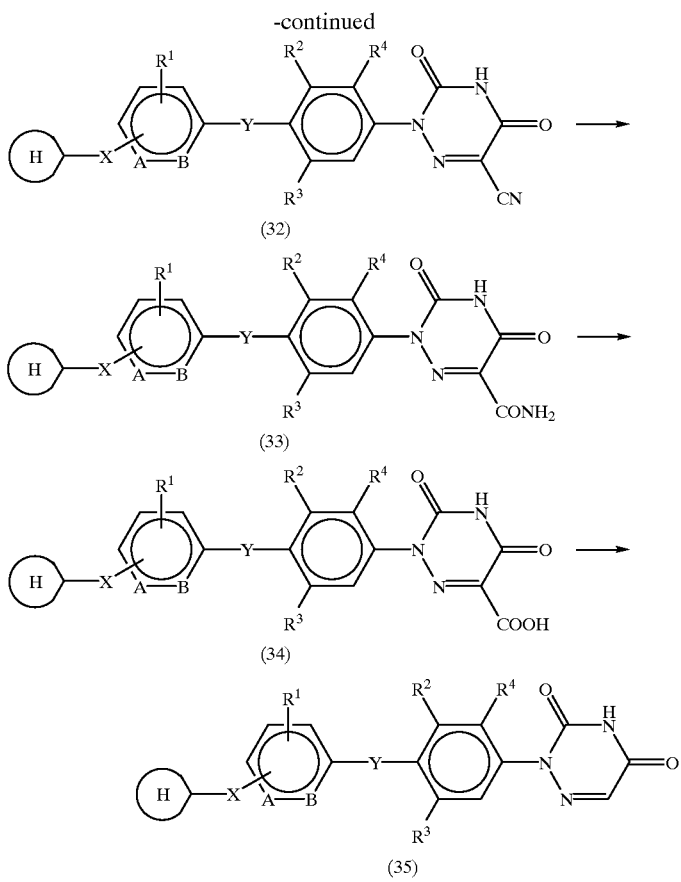

wherein the respective symbols have the same meanings as defined above.

This reaction is intended for the production of the desired product in accordance with the method described in the Journal of Medicinal Chemistry, Vol. 22, p. 1483 (1979).

Specifically, for example, compound [30] can be reacted with ethylcyanomethylenecarbonyl carbamate in an acetic acid-water system by a commonly known diazotizing reaction to yield compound [31]. Compound [31] may be subjected to a cyclization reaction under heating at 180° C. to 200° C. to yield compound [32], which may be subjected to a commonly known hydrolyzing reaction and then to a decarboxylating reaction at high temperature to yield desired compound [35].

The compounds (I) to (IV) or salts thereof of the invention are effective in the control of harmful parasitic protozoa in the breeding of animals including vertebrate animals such as mammals, fowls and fish, and insects, showing anti-protozoal activity against any and all stages of growth of such protozoa. Moreover, compounds (I) to (IV) and salts thereof of the present invention have sufficiently useful anti-protozoal activity against protozoa including susceptible strains or including strains resistant to the conventional chemicals. As a result, the compounds (I) to (IV) contribute to increased productivity in animal production (e.g. the productivity of meat, milk, fur, skin, eggs, honey, etc. as well as the bleedability of animals). Moreover, a more economical breeding of animals can be insured through use of the compounds (I) to (IV) of the present invention.

A broad spectrum of protozoa can be controlled with the compound of the invention. Among such protozoa may be mentioned those of the phylum Apicomplexa, for example protozoa of the family Eimeriidae such as protozoa of the genus Eimeria, specifically *E. acervulina, E. adenoides, E. alabahmensis, E. arloingi, E. auburnensis, E. bovis, E. brunetti, E. canis, E. contorta, E. ellipsoidales, E. falciformis, E. gallopavonis, E. hagani, E. intestinalis, E. magna, E. maxima, E. meleagridis, E. meleagrimitis, E. mitis, E. mivati, E. necatrix, E. ninakohlyakimovae, E. ovis, E. parva, E. pavonis, E. perforans, E. piriformis, E. praecox, E. stiedai, E. suis, E. tenella, E. truncata,* and *E. zuernii*; protozoa of the genus Isospora, e.g. *I. belli, I. canis, I. felis, I. rivolta,* and *I. suis*; Cryptosporidium, *Toxoplasma gondii*, protozoa of the family sarcocystidae such as *Sarcocystis bovicanis, S. bovihominis, S. ovicanis, S. ovifelis,* and *S. suihominis*; protozoa of the genus Leucocytozoon such as *L. simondi* and *L. caulleryi*, protozoa of the family Plasmodiidae such as *Plasmodium berghei, P. falciparum, P. malariae,* and *P. ovale*; protozoa of the subclass Piroplasmea; protozoa of the genus Babesia such as *B. argentina, B. bovis,* and *B. canis*; protozoa of the genus Theileria such as *T. parva*; Adeleina, *Hepatozoon canis*, etc.; protozoa of the subphylum Myxospora and of the subphylum Microspora; and protozoa of the genus Glugea and of the genus Nosema.

The compounds (I) to (IV) or salts thereof, can be used for both prophylactic and therapeutic purposes in various protozoal infections in vertebrate animals such as mammals (e.g. cattle, horse, hog, sheep, goat, camel, buffalo, donkey, rabbit, deer, reindeer, mink, chinchilla, raccoon, mouse, rat, guinea pig, golden hamster, dog, cat, human, etc.), fowls (e.g. chicken, quail, goose, turkey, duck, mallard, pigeon, etc.), and fresh water and seawater fishes (e.g. carp, eel, trout, sweet fish, catfish, salmon, sea bream, yellowtail, tiger puffer, tongue sole, flatfish, etc.) or insects (e.g. bee)

The compounds (I) to (IV) or salts thereof, can be safely administered, either as it is or in various dosage forms, whether orally or otherwise. Such dosage forms can be prepared by the per se known procedures (e.g. JP-A 1047/1993, JP-A 117250/1993, JP-A 240003/1990, JP-A 61972/1987).

For administration into the digestive canal of the host, the composition can be administered orally in such dosage forms as bulk powders, powders (inclusive of soluble powders), tablets, capsules, paste, liquid, granules, crumbles, pellets, etc., either as such or in admixture with feed or drinking water. For administration to the skin, the composition can be applied by dipping, spraying, washing, dripping, or coating. For non-oral administration, the composition can be used in the form of an injection (e.g. intramuscular, subcutaneous, intravenous, or intraperitoneal injection). The dosage form thus includes various liquids such as injectable solutions, oral liquids, liquids for application to the skin or into body cavities, drips, gels, emulsions and suspensions for oral administration, parenteral administration, or application to the skin, semisolids, ointments, powders, granules, pellets, tablets, capsules, aerosols or inhalants, and shaped articles containing the compound (I) to (IV) or a salt thereof.

Injectable solutions can be prepared by dissolving the compound (I) to (IV) or a salt thereof in a suitable vehicle, adding various optional additives such as a solubilizer, an isotonizing agent, e.g. an acid, a base or a buffer, an antioxidant, and an antiseptic, sterilizing the mixture and packing it into vials. The vehicle that can be used includes a variety of physiologically acceptable solvents, e.g. water, alcohols such as ethanol, butanol, benzyl alcohol, etc., glycerol, hydrocarbons, propylene glycol, polyethylene glycol, N-methylpyrrolidone, and mixtures of such solvents. To prepare an injection, the compound of the present invention may be dissolved in a physiologically acceptable vegetable or synthetic oil for injection.

The solubilizer may be any substance that promotes dissolution or prevents precipitation of the compound (I) to (IV) or a salt thereof in the solvent. Thus, for example, polyvinylpyrrolidone, polyethoxylated castor oil, polyoxyethylene sorbitan ester, etc. can be mentioned.

The antiseptic that can be used includes but is not limited to benzyl alcohol, trichlorobutanol, p-hydroxybenzoic esters, and n-butanol.

The oral liquid is provided either as a liquid which is administered as it is or in the form of a concentrate which is diluted to the dose concentration in the field and administered orally. Such an oral liquid can be manufactured by the established procedure.

The solution for application to the skin is administered to the skin by dripping, spreading, embrocating, washing, spraying, dipping, bathing, or cleansing. Such solutions can also be manufactured by the established procedures. It is advantageous to add thickeners in the course of preparation. The thickeners include but is not limited to such inorganic substances as bentonite, silica gel, aluminum monostearate, etc. and such organic substances as CMC sodium, other cellulose derivatives, polyvinyl alcohol and its copolymers, acrylates, and methacrylates.

Gels are applied to or coated on the skin or applied into body cavities. Gels can be manufactured by adding a sufficient amount of a thickener to a prepared solution to provide for an appropriate ointment-like consistency in the per se conventional manner. As the thickener, a variety of substances such as those mentioned above can be selectively employed.

The drip is topically applied to the skin by dripping or washing so that the active ingredient may penetrate the skin for a systemic effect or simply act on the skin surface.

The drip can be manufactured by dissolving, suspending, or emulsifying the compound (I) to (IV) or a salt thereof in a suitable vehicle or vehicle mixture for transdermal delivery. The drip may be supplemented with various additives such as a coloring agent, an absorption promoter, an antioxidant, a light screen, and a thickener.

The vehicle that can be used includes water, alkanols, glycols, polyethylene glycol, polypropylene glycol, glycerol, aromatic alcohols such as benzyl alcohol, phenethyl alcohol, phenoxyethanol, etc., esters such as ethyl acetate, butyl acetate, benzyl benzoate, etc., ethers such as alkylene glycol alkyl ether, dipropylene glycol monomethyl ether, diethylene glycol monobutyl ether, etc., ketones such as acetone, methyl ethyl ketone, etc., aromatic and/or aliphatic hydrocarbons, vegetable and synthetic oils, N,N-dimethylformamide (DMF), N,N-dimethylacetamide, N-methylpyrrolidone, and 2-dimethyl-4-oxomethylene-1,3-dioxolane, among others.

The coloring agent may be any pigment or dye that can be dissolved or suspended and administered safely to animals.

The absorption promoter that can be used includes dimethyl sulfoxide (DMSO), extender oils, isopropyl myristate, dipropylene glycol pelargonate, silicone oil, fatty acid esters, triglycerides, and aliphatic alcohols.

The antioxidant includes sulfites, metabisulfites such as potassium metabisulfite, ascorbic acid, butylhydroxytoluene, butylhydroxyanisole, and tocopherol.

The light screen may for example be a benzophenone derivative.

The thickener includes cellulose derivatives, starch derivatives, polyacrylates, alginates, and gelatin.

The emulsion may be whichever of the oil-in-water type or the water-in-oil type, and can be prepared by dissolving the compound (I) to (IV) or a salt thereof either in a hydrophobic solvent or in a hydrophilic solvent and homogenizing the solution in the presence of an emulsifier and other additives such as a coloring agent, an absorption promoter, antiseptic, an antioxidant, a light screen; and a thickener.

The hydrophilic solvent includes a variety of substances including paraffin oils, silicone oils, vegetable oils such as sesame oil, almond oil, castor oil, etc., synthetic triglycerides such as capryl/capric diglyceride, fatty acids of vegetable origin and their triglycerides, non-natural saturated or unsaturated fatty acids and the corresponding mono- and diglycerides, fatty acid esters such as ethyl stearate, n-butyryl adipate, hexyl laurate, dipropylene glycol pelargonate, etc., branched-chain fatty acid esters of $C_{16-17}$ saturated aliphatic alcohols, such as isopropyl myristate, isopropyl palmitate, etc., capryl/capric esters of $C_{12-18}$ saturated aliphatic alcohols, isopropyl stearate, oleyl oleate, decyl oleate, ethyl oleate, ethyl lactate, wax-like fatty acid esters such as dibutyl phthalate, diisopropyl adipate, etc., aliphatic alcohol esters of adipic acid, e.g. isotridecyl alcohol ester, 2-octyldodecanol ester, cetyl stearyl alcohol ester and oleyl alcohol ester, and fatty acids such as oleic acid.

The hydrophilic solvent includes water, alcohols such as propylene glycol, glycerol, sorbitol, etc., and mixtures of such solvents.

The emulsifier includes nonionic surfactants such as polyethoxylated castor oil, polyoxyethylene sorbitan monooleate, sorbitan monostearate, glycerol monostearate, polyoxyethylene stearate, and alkylphenol polyglycol ethers; amphoteric surfactants such as disodium N-lauryl- β-iminodipropionate, lecithin, etc., anionic surfactants such as sodium lauryl sulfate, aliphatic alcohol ether sulfates, mono- or dialkylpolyglycol ethers, orthophosphoric ester monoethanolamine salts, etc., and cationic surfactants such as cetyltrimethylammonium chloride, and so on.

For the purpose of stabilizing an emulsion, there may be added a thickener such as carboxymethylcellulose (CMC), methylcellulose (MC), other cellulose derivatives, starch derivatives, polyacrylates, alginic acid esters, gelatin, gum arabic, polyvinylpyrrolidone, polyvinyl alcohol, methyl vinyl ether-maleic anhydride copolymer, polyethylene glycol, waxes, silica gel, etc. in a suitable proportion.

When the antiprotozoal composition of the present invention is to be provided in the form of a suspension, such a suspension can be prepared by suspending the compound (I) to (IV) or a salt thereof uniformly in a medium together with various auxiliary agents such as a wetting agent, a coloring agent, an absorption promoter, an antiseptic, an antioxidant, a light screen, etc.

As the wetting agent (dispersant), the surfactants mentioned above can be selectively added in a suitable proportion. The semisolid dosage form for oral administration or application to the skin can be prepared by admixing the compound (I) to (IV) or a salt thereof with a suitable excipient, optionally together with other additives, and molding the resulting mixture.

The excipient may be any physiologically acceptable inert material, thus including various inorganic excipients such as sodium chloride, e.g. calcium carbonate and other carbonates, hydrogencarbonates, aluminum oxide, silic acid, silica gel, phosphates, etc. and organic excipients such as saccharides, cellulose, and feedstuffs such as powdered milk, cracked or crushed cereals, starches, and others.

The above-mentioned antiseptic, antioxidant, and coloring agent may also be added in suitable amounts. In addition, a lubricant such as magnesium stearate, stearic acid, talc, bentonite, etc., a disintegrator such as starch and crosslinked polyvinylpyrrolidone, and a binder such as starch, gelatin, polyvinylpyrrolidone, crystalline cellulose, etc. can also be added.

The antiprotozoal composition of the present present invention may contain more than one species of compound (I) to (IV) or a salt thereof of the present invention, and barring the risk of interactions, may further contain, or may be used in combination with, other substances assisting in the promotion of animal health or sharing the prophylactic or therapeutic function with the compound of the present invention.

The antiprotozoal composition of the present invention is formulated or prepared so as to contain the compound (I) to (IV) or its salt in a concentration ranging from about 0.01 ppm to about 1%, preferably about 0.1 ppm to 0.1%. In the case of a dosage form for use after dilution in the field, its concentration is about 0.01 to 90% or preferably about 0.1 to 30%.

Generally, the antiprotozoal composition of the present invention can be administered to an animal within the dose range of about 0.01 to about 50 mg/day, preferably about 0.1 to 5 mg/day, as the compound (I) to (IV) or a salt thereof, per kilogram body weight of the recipient animal. For example, the compound (I) to (IV) or a salt thereof can be incorporated in the animal diet at a level ranging from about 0.01 to about 100 ppm, preferably about 0.1 to 50 ppm. The medicated diet thus obtained can be used for both therapeutic and prophylactic purposes. Such a medicated diet can be generally provided by preparing a concentrate or premix containing generally about 0.5 to 30 weight %, preferably about 1 to 20 weight % of the compound (I) to (IV) or a salt thereof together with the routine excipient for animal use and mixing it into the regular feedstuff. The excipient that can be used includes corn flour supplemented with a small proportion of edible oil, e.g. corn oil or soybean oil, for prevention of dust formation, corn, soybean meal, and mineral salts. The premix is evenly incorporated in the ration and fed to the animal.

For the treatment and prevention of sporozoasis in domestic fowls, particularly chicken, quail, duck, mallard, goose, and turkey, generally about 0.01 to 100 ppm or preferably about 0.1 to 50 ppm of the compound (I) to (IV) or its salt is mixed into a suitable edible material such as a nutrient formula feed. Administration can also be made via drinking water.

For use in the treatment of animals, typically in the therapy of sporozoasis or toxoplasmosis in a mammal, about 0.5 to 100 mg/kg b. wt. of the compound (I) to (IV) or a salt thereof is administered daily. The above dosage is not critical, however, and can be increased or decreased according to animal species and body weight, dosing method, individual response to treatment, formulation, dosing schedule, and other factors. For massive administration, the compound of the present invention can be conveniently administered in a few divided doses.

For application to fish, the composition is generally administered orally, for example via feed or by way of a "drug bath". The drug-bath method comprises transferring fish from a culture pond to a drug-containing bath and keeping them in the bath for a while (several minutes to a few hours). However, the whole habitat for fish (e.g. a pool, aquarium, tank, or pond) may be treated either on a temporary basis or permanently. In such applications, the compound (I) to (IV) or a salt thereof can be used in a dosage form suitable for each treatment method. The concentration of the active ingredient in the composition is about 1 ppm to 10 weight %.

For use in a drug bath or in the omnibus treatment of the habitat (pool treatment), the antiprotozoal compound of the present invention is preferably provided in the form of a solution in a mixture of one or more polar solvents which can be diluted or dispersed with water. Such a solution is prepared by dissolving or suspending the compound (I) to (IV) or a salt thereof in a water-soluble vehicle such as a polar solvent. The pH of the aqueous solution after addition of the compound (I) to (IV) or a salt thereof is preferably pH 7–10, particularly about 8–10.

Since administration of the compound of the present invention results in successful control of protozoa and reduction in the incidence of associated diseases and death and consequent improvement in retarded growth and general condition, the composition can be used with advantage for preventing decrease of rearing production, e.g. the production of meat, milk, fur, eggs, honey, etc. Moreover, with the composition of the present invention, ornamental or pet animals, too, can be reared in good health.

INDUSTRIAL APPLICATION

The triazine derivative or a salt thereof of the present invention has high antiprotozoal activity with a high toxicological threshold insuring safety.

EXAMPLES

The following reference examples, examples, test example and formulation example are intended to illustrate the present invention in further detail and should by no means be interpreted as limiting its scope.

Reference Example 1
Production of 2-chloro-5-[4-(2,6-dichloro-4-nitrobenzyl)benzoyl]pyridine 75.6 g (0.567 mol) of aluminum chloride and 300 ml of EDC (1,2-dichloroethane) were mixed and cooled to 8 to 10° C. To this mixture, 50 g (0.227 mol) of 6-nicotinoyl chloride and 100 ml of EDC were added drop by drop over a 20-minute period, while the temperature was kept at 8 to 10° C. After stirring at constant temperature for 30 minutes., 53.4 g (0.227 mol) of 4-benzyl-3,5-dichloronitrobenzene and 100 ml of EDC were added drop by drop over a 30-minute period, while the temperature was kept below 10° C. After stirring at room temperature for 1 hour, the mixture was heated to 70° C. and stirred for 3 hours. The reaction mixture was poured over ice water and extracted with chloroform. The water layer was neutralized with a 20% aqueous solution of NaOH; chloroform was added, followed by stirring, after which the mixture was filtered through Hyflow, and the filtrate was separated into different layers. After being combined and dried with $Na_2SO_4$, the organic layers were concentrated and purified by silica gel column chromatography (chloroform:ethanol=20:1) to give 40.8 g of a light brown crystal (yield 42.6%).

$^1$H-NMR ($CDCl_3$); 4.51 (s,2H), 7.32 (d,2H), 7.47 (d,1H), 7.73 (d,2H), 8.07 (dd,1H), 8.25 (s,2H), 8.74 (d,1H)

Reference Example 2
Production of 5-[4-(2,6-dichloro-4-nitrobenzyl)benzoyl]-2-methylthiopyridine 3.08 g of 4-benzyl-3,5-dichloronitrobenzene and 2.46 g of 6-methylthionicotinoyl chloride were treated in the same manner as in Reference Example 1 to give 5.15 g of the title compound as a brown oil.

$^1$H-NMR ($CDCl_3$); 2.61 (s,3H), 4.49 (s,2H), 7.22–7.32 (m,3H), 7.71 (d,2H), 7.92 (dd,1H), 8.24 (s,2H), 8.77 (d,1H)

Reference Example 3
Production of 4-[4-(4-chlorobenzoyl-3-methylbenzyl)]-3,5-dichloronitrobenzene 10.0 g of 3,5-dichloro-4-(3-methylbenzoyl)nitrobenzene and 8.9 g of 4-chlorobenzoyl chloride were treated in the same manner as in Reference Example 1 to give 10.2 g of the title compound as a light red oil.

$^1$H-NMR ($CDCl_3$); 2.30 (s,3H), 4.43 (s,2H), 7.05 (d,1H), 7.11 (s,1H), 7.22 (d,1H), 7.40 (d,2H), 7.71 (d,2H), 8.24 (s,2H)

Reference Example 4
Production of 2-chloro-5-[4-(2-chloro-6-methyl-4-nitrobenzyl)benzoyl]pyridine 8.2 g (0.06 mol) of 97% $AlCl_3$ was suspended in 50 ml of EDC; 4.2 g (0.024 mol) of 6-chloronicotinoyl chloride was added at room temperature (heat generated to about 30° C.). After stirring at constant temperature for 15 minutes (yellow crystal precipitated), 5.2 g (0.05 mol) of 4-benzyl-3-chloro-5-methylnitrobenzene was added. After overnight stirring at room temperature, the mixture was stirred under boiling refluxing for 2 hours, after which 50 ml of ice water was added, followed by stirring for 15 minutes and liquid layer separation. After water washing, the organic layer was dried with $MgSO_4$ and concentrated. The residue was purified by silica gel column chromatography (developing solvent=ethyl acetate:n-hexane=1:3) to yield the title compound (3.0 g).

Yield: 37.4%

Melting point: 140–141° C. (light yellow crystals)

$^1$H-NMR ($CDCl_3$); 2.41 (s,3H), 4.38 (s,2H), 7.46 (q,4H), 7.47 (d,1H), 8.02 (d,1H), 8.05 (dd,1H), 8.20 (d,1H), 8.74 (d,1H)

Reference Example 5
Production of 2-chloro-5-[4-(2-bromo-6-chloro-4-nitrobenzyl)benzoyl]pyridine The title compound was produced as a light yellow crystals at a yield of 32.2%, in the same manner as in Reference Example 4.

Melting point: 126° C.

$^1$H-NMR ($CDCl_3$); 4.55 (s,2H), 7.47 (d,1H), 7.51 (q,4H), 8.07 (dd,1H), 8.29 (d,1H), 8.43 (d,1H), 8.75 (d,1H)

Reference Example 6
Production of 3,5-dichloro-4-[4-(4-methylbenzoyl)benzyl]nitrobenzene The title compound was produced as a red-brown oil at a yield of 43.8%, in the same manner as in Reference Example 4.

$^1$H-NMR ($CDCl_3$); 2.43 (s,3H), 4.48 (s,2H), 7.26–7.73 (m,8H), 8.25 (s,2H)

Reference Example 7
Production of 5-[4-(4-amino-2,6-dichlorobenzyl)benzoyl]-2-chloropyridine 40 g (0.0948 mol) of 2-chloro-5-[4-(2,6-dichloro-4-nitrobenzyl)benzoyl]pyridine was mixed with 400 ml of ethyl acetate; 107 g (0.474 mol) of $SnCl_2.2H_2O$ was added, followed by stirring at 55 to 60° C. for 2 hours. After the reaction mixture was transferred to a beaker and neutralized with concentrated aqueous ammonia, the byproduct (resinous substance) precipitated was separated from the ethyl acetate layer by decantation. Similarly, after the resinous substance was washed with ethyl acetate, the washing was separated into different layers by decantation; the resulting ethyl acetate layer was combined with the previous ethyl acetate layer, washed with water, and dried with $Na_2SO_4$, after which the dry product was concentrated to dryness to give 27.2 g (yield 73.2%) of a whitish brown crystal.

$^1$H-NMR ($CDCl_3$); 3.80 (br-s,2H), 4.28 (s,2H), 6.68 (s,2H), 7.31 (d,2H), 7.45 (d,1H), 7.70 (d,2H), 8.06 (dd,1H), 8.75 (d,1H)

Reference Example 8
Production of 5-[4-(4-amino-2,6-dichlorobenzyl)benzoyl]-2-methylthiopyridine The title compound was produced as a pale yellow powder at a yield of 57.3%, in the same manner as in Reference Example 7.

$^1$H-NMR ($CDCl_3$); 2.61 (s,3H), 3.71 (br-s,2H), 4.27 (s,2H), 6.67 (s,2H), 7.20–7.33 (m,3H), 7.69 (d,2H), 7.91 (dd,1H), 8.79 (d,1H)

Reference Example 9
Production of 4-[4-(4-chlorobenzoyl)-3-methylbenzyl]-3,5-dichloroaniline In a 500 ml eggplant-shaped flask, 10.0 g of 4-[4-(chlorobenzoyl-3-methylbenzyl)-3,5-dichloronitrobenzene was dissolved in 200 ml of ethyl acetate; 16.0 g of $SnCl_2.2H_2O$ was added with stirring using a magnetic stirrer, followed by heating and refluxing for 2 hours. After completion of the reaction was confirmed by TLC (thin-layer chromatography), the reaction mixture was poured over 500 ml of ice water; 300 ml of $NH_4OH$ was added, followed by thorough stirring and separation of the ethyl acetate layer. The remaining portion was further extracted by 2 additions of 300 ml of ethyl acetate; the organic layers were combined washed with saturated saline, dried with $MgSO_4$, and concentrated. Since TLC (hexane:ethyl acetate=4:1) demonstrated the presence of only a very small amount of impurity substances, the concentrate was used for the next reaction without purification. Yield 9.3 g, light red crystal (crystallized when kept standing at 25 to 26° C., but melting point was undeterminable).

$^1$H-NMR (CDCl$_3$); 2.00 (br-s,2H), 2.23 (s,3H), 4.21 (s,2H), 6.67 (s,2H), 7.01 (d,1H), 7.10 (s,1H), 7.19 (d,1H), 7.40 (d,2H), 7.72 (d,2H)

Reference Example 10

Production of 5-[4-(4-amino-2-chloro-6-methylbenzyl) benzoyl]-2-chloropyridine 3.0 g (7.5 mmol) of 2-chloro-5-[4-(2-chloro-6-methyl-4-nitrobenzyl)benzoyl]pyridine was dissolved in 50 ml of ethyl acetate; 8.5 g (37.5 mmol) of SnCl$_2$.2H$_2$O was added at room temperature. After stirring at 50 to 60° C. for 1 hour, 5 ml of water and about 8.5 ml of 25% aqueous ammonia were added (tin hydroxide adhered to flask base). The organic layer was separated from the water layer and residue by decantation; the water layer and residue were further extracted with 2 additions of 25 ml of ethyl acetate. The organic layers (ethyl acetate layers) were combined, dried with MgSO$_4$, and concentrated. A small amount of diethyl ether was added to the residue; the crystal precipitated was collected by filtration to give 9.6 g. Yield: 82.9%

Melting point: 140–141° C. (pale yellow crystals)

$^1$H-NMR (CDCl$_3$); 2.15 (s,3H), 3.69 (s,2H), 4.16 (s,2H), 6.46 (d,1H), 6.65 (d,1H), 7.45 (q,1H), 7.46 (q,4H), 8.06 (dd,1H), 8.75 (d,1H)

Reference Example 11

Production of 5-[4-(4-amino-2-bromo-6-methylbenzyl) benzoyl]-2-chloropyridine

The title compound was produced as a colorless prismatic crystal at a yield of 95%, in a similar manner as in Reference Example 10.

Melting point: 147–148° C.

$^1$H-NMR (CDCl$_3$); 3.82 (s,2H), 4.32 (s,2H), 6.72 (d,1H), 6.87 (d,1H), 7.45 (d,1H), 7.51 (q,4H), 8.06 (dd,1H), 8.76 (d,1H)

Reference Example 12

Production of 3,5-dichloro-4-[4-(4-methylbenzoyl)benzyl] aniline

The title compound was produced as a brown oil at a yield of 97.5%, in a similar manner as in Reference Example 10.

$^1$H-NMR (CDCl$_3$); 2.43 (s,3H), 3.76 (br-s,2H), 4.27 (s,2H), 6.68 (s,2H), 7.25–7.71 (m,8H)

Reference Example 13

Production of 1-benzylidene-2-{4-[4-(6-chloronicotinoyl) benzyl]-3,5-dichlorophenyl}hydrazine 3.4 g (8.68 mmol) of crude 5-[4-(4-amino-2,6-dichlorobenzyl)benzoyl]-2-chloropyridine was dissolved in 25 ml of acetic acid; 3.5 ml of 35% hydrochloric acid was added. While the brown liquid was ice cooled below 10° C., a solution of 0.68 g (9.71 mmol) of 98.5% NaNO$_2$ in 1 ml of water was added drop by drop over a 25-minute period. After stirring for 40 minutes, 0.92 g (8.67 mmol) of benzaldehyde was added, after which a solution of 5.4 g (23.93 mmol) of SnCl$_2$.2H$_2$O in 6 ml of 35% hydrochloric acid was added drop by drop over a 30-minute period. After stirring for 30 minutes, 50 ml of water was added; this mixture was added to 150 ml of ethyl acetate and stirred, followed by liquid layer separation. The organic layer was separated, washed with water (3 times), and with aqueous sodium bicarbonate (1 time), then dehydrated and concentrated. The yellow caramel obtained was stirred in ethyl acetate/hexane to give 2.49 g of a yellow crystals having a melting point of 182 to 184° C. (yield: 57.9%).

$^1$H-NMR (CDCl$_3$); 4.33 (s,2H), 7.13 (s,2H), 7.25–7.75 (m,12H), 8.05 (dd,1H), 8.75 (d,1H)

Reference Example 14

Production of 1-benzylidene-2-{3,5-dichloro-4-[4-(6-methylthionicotinoyl)benzyl]}phenylhydrazine The title compound was produced as a yellow crystal at a yield of 60.8%, in a similar manner as in Reference Example 13.

Melting point: 184–186° C.

$^1$H-NMR (CDCl$_3$); 2.61 (s,3H), 4.32 (s,2H), 7.12 (s,2H), 7.21–7.74 (m,12H), 7.92 (dd,1H), 8.79 (d,1H)

Reference Example 15

Production of 1-benzylidene-2-{4-[4-(4-chlorobenzoyl)-3-methylbenzyl]-3,5-dichlorophenyl}hydrazine The title compound was produced as a yellow crystal at a yield of 78%, in a similar manner as in Reference Example 13.

Melting point: 166–167° C.

$^1$H-NMR (CDCl$_3$); 2.30 (s,3H), 4.25 (s,2H), 7.05 (d,1H), 7.10 (s,2H), 7.12 (s,1H), 7.20 (d,1H), 7.28–7.43 (m,5H), 7.61–7.68 (m,4H), 7.72 (d,2H)

Reference Example 16

Production of 1-benzylidene-2-{4-[4-(6-chloronicotinoyl) benzyl]-3-chloro-5-methylphenyl}hydrazine 2.2 g (6 mmol) of 5-[4-(4-amino-2-chloro-6-methylbenzyl)benzoyl]-2-chloropyridine was dissolved in 30 ml of acetic acid; 1.5 ml (18 mmol) of concentrated hydrochloric acid was added at room temperature. After stirring the reaction mixture at room temperature for 15 minutes, 490 mg (7 mmol) of 98.5% NaNO$_2$ in 1 ml of water was dropwised to the resulting slurry, at 5 to 10° C. over 5 minutes period. After stirring at 5 to 10° C. for 30 minutes, 630 mg (6 mmol) of benzaldehyde was added, after which a solution of 4.0 g (18 mmol) of SnCl$_2$.2H$_2$O in 5 ml of concentrated hydrochloric acid was added drop by drop at 5 to 10° C. over a 5-minute period. After stirring at constant temperature for 30 minutes and at room temperature for 1 hour, 50 ml of ethyl acetate and 30 ml of water were added. After liquid layer separation, the water layer was further extracted with 2 additions of 30 ml of ethyl acetate. The organic layers were combined, washed with water, then with aqueous sodium bicarbonate, and dried with MgSO$_4$, and concentrated. To the residue, 5 ml of diethyl ether was added; the crystal precipitated was collected by filtration. Yield 2.1 g, recovery rate 73.8%, melting point 180 to 181° C. (yellow needle)

$^1$H-NMR (CDCl$_3$); 2.23 (s,3H), 4.22 (s,2H), 6.85 (d,1H), 7.14 (d,1H), 7.24–7.71(m,12H), 8.06 (dd,1H), 8.76 (d,1H)

Reference Example 17

Production of 1-benzylidene-2-{4-[4-(6-chloronicotinoyl) benzyl]-3-bromo-5-chlorophenyl}hydrazine The title compound was produced as a light yellow needle crystals at a yield of 81.6%, in a similar manner as in Reference Example 16.

Melting point: 207–208° C.

$^1$H-NMR (CDCl$_3$); 4.37 (s,2H), 7.12 (d,1H), 7.30–7.72 (m,13H), 8.06 (dd,1H), 8.76 (d,1H)

Reference Example 18

Production of 1-benzylidene-2-{3,5-dichloro-4-[4-methylbenzoyl)benzyl]phenyl}hydrazine The title compound was produced as a light brown crystals at a yield of 89.6%, in a similar manner as in Reference Example 16.

¹H-NMR (CDCl₃); 2.42 (s,3H), 4.32 (s,2H), 7.12 (s,2H), 7.25–7.74 (m,15H)

Reference Example 19
Production of 1-benzylidene-2-{4-[4-(6-chloronicotinoyl)benzyl]-3,5-dichlorophenyl}-4-(2,2-dimethoxyethyl)semicarbazide 35.2 g (0.0711 mol) of 2-benzylidene-1-{4-[4-(6-chloronicotinoyl)benzyl]-3,5-dichlorophenyl}hydrazine was dissolved in 360 ml of acetonitrile; 14.04 g (0.1067 mol) of 2,2-dimethoxyethyl isocyanate and 540 mg of 1,8-diazabicyclo[5,4,0]-7-undecene (DBU) were added. After stirring at room temperature for 1 hour, the reaction mixture was poured over ice water and extracted with ethyl acetate. The extract was dried with Na₂SO₄, concentrated to dryness, and purified by silica gel column chromatography (once with chloroform:ethanol=20:1, once with hexane:ethyl acetate=1:1) to give 32.5 g (yield: 73.0%) of a colorless syrup.

¹H-NMR (CDCl₃); 3.48 (s,6H), 3.53 (m,2H), 4.47 (s,2H), 4.52 (t,1H), 6.9 (t,1H), 7.26–7.59 (m,11H), 7.74 (d,2H), 8.08 (dd,1H), 8.78 (d,1H)

Reference Example 20
Production of 1-benzylidene-2-{4-[4-(4-chlorobenzoyl)-3-methylbenzyl]-3,5-dichlorophenyl}-4-(2,2-dimethoxyethyl)semicarbazide The title compound was prepared as a colorless crystals at a yield of 95%, in a similar manner as in Reference Example 19.

Melting point: 67–69° C.
¹H-NMR (CDCl₃); 2.29 (s,3H), 3.48 (s,6H), 3.55 (t,2H), 4.40 (s,2H), 4.53 (t,1H), 6.94–7.62(m,11H), 7.30 (s,2H), 7.42 (d,2H), 7.74 (d,2H)

Reference Example 21
Production of 1-benzylidene-2-{4-[4-(6-chloronicotinoyl)benzyl]-3-chloro-5-methylphenyl}-4-(2,2-dimethoxyethyl)semicarbazide The title compound was prepared as a pale yellow powder at a yield of 86.5%, in a similar manner as in Reference Example 19.

¹H-NMR (CDCl₃); 2.32 (s,3H), 3.48 (s,6H), 3.55 (t,2H), 4.35 (s,2H), 4.53 (t,1H), 6.95 (t,1H), 7.03 (d,1H), 7.23–7.58 (m,10H), 7.73 (d,2H), 8.07 (dd,1H), 8.78 (d,1H)

Reference Example 22
Production of 1-benzylidene-2-{4-[4-(6-chloronicotinoyl)benzyl]-3-bromo-5-chlorophenyl}-4-(2,2-dimethoxyethyl)semicarbazide The title compound was produced as a pale yellow powder at a recovery rate of 95.9%, in the same manner as in Reference Example 19.

¹H-NMR (CDCl₃); 3.48 (s,6H), 3.54 (t,2H), 4.52 (s,2H), 4.53 (t,1H), 6.94 (t,1H), 7.28–7.58 (m,l1H), 7.74 (d,2H), 8.08 (dd,1H), 8.79 (d,1H)

Reference Example 24
Production of 3,5-dichloro-4-(3-methylbenzyl)nitrobenzene

To a 1 liter four-mouthed flask equipped with a three-one motor, thermometer, condenser, and dripping funnel, a solution of methyl 3-methylphenylacetate and 4-bromo-3,5-dichloronitrobenzene in 500 ml of DMSO was added; while the solution was stirred at room temperature, NaOH pellets in a molar amount double the amount of the solution were added. Subsequently, 30 ml of concentrated hydrochloric acid was added; the reaction temperature was gradually increased to 75 to 80° C., at which temperature the reaction was carried out for 1 hour.

After completion of the reaction was confirmed by TLC (hexane:ethanol=9:1), the reaction temperature was increased to 140 to 145° C., at which temperature the reaction was carried out for 6 hours. After completion of the reaction, the reaction product was poured over 2 l of ice water; the water layer was removed; the resulting precipitate was extracted with 500 ml of toluene, dried with MgSO₄, and concentrated, to yield 87.0 g (89.6%) of the title compound as a dark red oil, which was then used as is for the next reaction.

¹H-NMR (CDCl₃); 2.28 (s,3H), 4.34 (s,2H), 6.90–7.25 (m,4H), 8.18(s,2H)

Reference Example 25
Production of 3,5-dichloro-4-phenylthionitrobenzene 25 g (0.227 mol) of thiophenol and 67.6 g (0.25 mol) of 4-bromo-3,5-dichloronitrobenzene were mixed with 680 ml of DMSO; 18.0 g (0.27 mol) of KOH was added at room temperature. After stirring at 55 to 60° C. for 3 hours, the reaction mixture was poured over ice water and extracted with toluene. The extract was dried with Na₂SO₄; a small amount of silica gel was added, followed by stirring and filtration. The filtrate was concentrated to dryness and purified by silica gel column chromatography (hexane:AcOEt=5:1) to yield 57.0 g (83.6%) of the title compound as a whitish yellow crystal.

¹H-NMR(CDCl₃); 7.19–7.29 (m,5H), 8.26 (s,2H)

Reference Example 26
Production of 2-chloro-5-(4-(2,6-dichloro-4-nitrophenylthio)benzoyl)pyridine 13 g (0.1 mmol) of aluminum chloride was dissolved in 100 ml of nitrobenzene. To this solution being cooled to 8 to 10° C., 5.9 g (33.3 mmol) of 6-chloronicotinoyl chloride dissolved in 30 ml of nitrobenzene was added drop by drop, followed by stirring at constant temperature for 30 minutes. To this solution, 10 g (33.3 mmol) of 3,5-dichloro-4-phenylthionitrobenzene dissolved in 30 ml of nitrobenzene was added drop by drop at constant temperature over a 15-minute period, followed by stirring at room temperature for 30 minutes, then at 100° C. for 5 hours. The reaction mixture was poured over ice water and extracted with chloroform. The extract was dried with Na₂SO₄ and purified by silica gel column chromatography to yield 9.8 g (67.1%) of the title compound as a yellow crystal.

¹H-NMR(CDCl₃): 7.21 (d,2H), 7.48 (d,1H), 7.71 (d,2H), 8.07 (dd,1H), 8.33 (s,2H), 8.73 (d,1H)

Reference Example 27
Production of 5-(4-(4-amino-2,6-dichlorophenylthio)benzoyl)-2-chloropyridine 4.0 g (9.10 mmol) of 2-chloro-5-(4-(2,6-dichloro-4-nitrophenylthio)benzoyl)pyridine was mixed with 40 ml of ethyl acetate; 10.3 g (45.5 mmol) of SnCl₂.2H₂O was added, followed by stirring at 45 to 45° C. for 2 hours. The reaction mixture was transferred to a beaker and neutralized with concentrated aqueous ammonia, after which the ethyl acetate layer was separated by decantation. The ethyl acetate layer was washed with water, dried with Na₂SO₄, and concentrated to dryness to yield 3.54 g (94.9%) of a brown crystal.

¹H-NMR(CDCl₃): 4.12 (br-s,2H), 6.80 (s,2H), 7.10 (d,2H), 7.67(d,2H), 7.46(d,1H), 8.04 (dd,1H), 8.73 (d,1H)

Reference Example 28
Production of 1-benzylidene-2-{4-[4-(6-chloronicotinoyl)phenylthio]-3,5-dichlorophenyl}hydrazine 3.0 g (7.32 mmol) of 5-[4-(4-amino-2,6-dichlorophenylthio)benzoyl]-2-chloropyridine and 30 ml of acetic acid were mixed under heating to yield a solution; 3 ml of c-HCl was added. After the mixture was cooled to 8 to 10° C., 0.56 g of NaNO$_2$ in 1.5 ml of water (8.05 mmol, 1.1 eq.) was added drop by drop over a 15-minute period, while the temperature was kept constant. After stirring at constant temperature for 1 hour, 0.78 g (7.32 mmol, 1.0 eq) of benzaldehyde was added, after which 4.13 g of SnCl$_2$.2H$_2$O in 5 ml of c-HCl (18.3 mmol, 2.5 eq) was added drop by drop over a 30-minute period, while the temperature was kept at 8 to 10° C., followed by stirring at constant temperature for 2 hours. To the reaction mixture, ethyl acetate and water were added, followed by liquid layer separation, after which the water layer was extracted with ethyl acetate. The organic layers were combined and washed with water, then with a 1 N aqueous solution of NaOH. After water washing, this was dried with Na$_2$SO$_4$, concentrated to dryness, and crystallized with hexane to yield 4.1 g of a crude brown crystal.

$^1$H-NMR(CDCl$_3$); 7.12–7.85 (m,14H), 8.04 (dd,1H), 8.75 (d,1H)

Reference Example 29

Production of 1-benzylidene-2-{4-[4-(6-chloronicotinoyl) phenylthio]-3,5-dichlorophenyl}-4-(2,2-dimethoxyethyl) semicarbazide 4.1 g (7.32 mmol) of crude 2-benzylidene-1-{4-[4-(6-chloronicotinoyl)phenylthio]-3,5-dichlorophenyl}hydrazine was dissolved in 100 ml of acetonitrile; 1.44 g (11.0 mmol) of 2,2-dimethoxyethyl isocyanate and 56 mg of DBU were added. After stirring at room temperature for 1 hour and at 40° C. for 1 hour, the reaction mixture was poured over ice water and extracted with ethyl acetate. The extract was dried with Na$_2$SO$_4$, and concentrated to dryness to yield 5.1 g of a crude red-brown syrup.

$^1$H-NMR(CDCl$_3$); 3.48 (s,6H), 3.55 (m,2H), 4.53 (t,1H), 6.9 (t,1H), 7.22–7.60 (m,11H), 7.72 (d,2H), 8.05 (dd,1H), 8.76 (d,1H)

Reference Example 30

Production of 3,5-dichloro-4-(4-formylbenzyl)nitrobenzene 11.4 g of titanium tetrachloride was dissolved in 100 ml of dichloromethane; 5.2 g of dichloromethylmethyl ether dissolved in 5 ml of dichloromethane was added drop by drop at −5° C. To this reaction mixture, 8.5 g of 4-benzyl-3,5-dichloronitrobenzene in 15 ml of dichloromethane was added drop by drop under the same conditions. After completion of the dropwise addition, the reaction mixture was stirred at 25 to 30° C. for 1 day and added to 100 ml of ice water. The organic layer was separated and washed with water, after which it was concentrated to dryness with magnesium sulfate; the residue was purified by silica gel column chromatography (silica gel-toluene). Yield: 4.5 g Melting point: 116–117° C. (yellow powder)

$^1$H-NMR(CDCl$_3$); 4.49 (s,2H), 7.58 (q,4H), 8.23(s,2H), 9.95 (s,1H)

Reference Example 31

Production of 3,5-dichloro-4-[4-(5-oxazolyl)benzyl] nitrobenzene 3.1 g of 3,5-dichloro-4-(4-formylbenzyl)nitrobenzene was suspended in 50 ml of methanol; while this suspension was stirred at 20 to 25° C., 2.0 g of tosyl methyl isocyanide and 1.4 g of potassium carbonate were added. The reaction mixture was stirred and reacted for 2 hours, after which it was concentrated; 50 ml of water was added to the residue, followed by 2 extractions with 50 ml of ethyl acetate. The organic layer was washed with water and dried with magnesium sulfate, after which it was concentrated. The residue was purified by silica gel column chromatography (chloroform) to give 2.1 g of the title compound as a yellow prismatic crystals.

Melting point: 114–115° C.

$^1$H-NMR(CDCl$_3$); 4.43 (s,2H), 7.31 (s,1H), 7.40 (q,4H), 7.89 (s,1H), 8.23 (s,2H)

Reference Example 32

Production of 3,5-dichloro-4-[4-(5-oxazolyl)benzyl]aniline 2.1 g of 3,5-dichloro-4-[4-(5-oxazolyl)benzyl] nitrobenzene was dissolved in 50 ml of ethyl acetate; 6.8 g of stannous chloride-2H$_2$O was added, followed by a reaction for 30 minutes. After completion of the reaction, 5 ml of water and concentrated aqueous ammonia were added to neutralize the reaction mixture. The organic layer was separated by decantation; the water layer and precipitate were twice extracted with 50 ml of ethyl acetate. The organic layer was washed with water, after which it was dried with magnesium sulfate and concentrated. The residue was crystallized by the addition of a small amount of diethyl ether to give 1.6 g of title compound as pale yellow prismatic crystals. Yield: 1.6 g Melting point: 151–152° C.

$^1$H-NMR(CDCl$_3$); 3.75 (br-s,2H), 4.21 (s,2H), 6.67 (s,2H), 7.28 (s,1H), 7.39 (q,4H), 7.87 (s,1H)

Reference Example 33

Production of 1-benzylidene-2-[3,5-dichloro-4-(5-oxazolyl) benzyl]phenylhydrazine Using 1.6 g of 3,5-dichloro-4-[4-(5-oxazolyl)benzyl] aniline, 1.6 g of the title compound was produced as a light yellow prismatic crystal by the method described in Reference Example 13.

Melting point: 179–180° C.

$^1$H-NMR(CDCl$_3$); 4.25 (s,2H), 7.09 (s,2H), 7.24–7.86 (m,13H)

EXAMPLE 1

Production of 2-{4-[4-(6-chloronicotinoyl)benzyl]-3,5-dichlorophenyl}-4,5-dihydro-1,2,4-triazin-3(2H)-one (Compound No. 1)

32.1 g (51.3 mmol) of 1-benzylidene-2-{4-[4-(6-chloronicotinoyl)benzyl]-3,5-dichlorophenyl}-4-(2,2-dimethoxyethyl)semicarbazide was dissolved in 330 ml of acetonitrile; 10.4 g of concentrated hydrochloric acid was added at room temperature, followed by stirring for 1 hour. The reaction mixture was concentrated; ethyl acetate and water were added, followed by stirring for 30 minutes. After liquid layer separation, the water layer was extracted with ethyl acetate. The organic layers were combined, dried with Na$_2$SO$_4$, and concentrated to dryness. This concentrate was dissolved in acetonitrile under heating and recrystallized; the crystal obtained was washed by sequential additions of small amounts of hot ethyl acetate and chloroform to give 12.0 g of a white crystal.

Melting point: 188–191° C.

$^1$H-NMR (CDCl$_3$); 4.15(t,2H), 4.40(s,2H), 5.79(br-s,1H), 7.08–7.16(m,1H), 7.35(d,2H), 7.46(d,1H), 7.63(s,2H), 7.70 (d,2H), 8.06(dd,1H), 8.76(d,1H)

EXAMPLE 2

Production of 2-{4-[4-((6-chloro-3-pyridyl)hydroxymethyl) benzyl]-3,5-dichlorophenyl}-4,5-dihydro-1,2,4-triazin-3 (2H)-one (Compound No. 2)

8.0 g (0.0169 mol) of 2-{4-[4-(6-chloronicotinoyl) benzyl]-3,5-dichlorophenyl}-4,5-dihydro-1,2,4-triazin-3 (2H)-one was dissolved in 300 ml of methanol. After this solution was cooled to 3 to 5° C., 1.9 g (0.0507 mol) of sodium borohydride was added over a 15-minute period, followed by stirring at constant temperature for 2.5 hours. Under ice cooling, the reaction mixture was neutralized with a 2 N aqueous solution of HCl. After the reaction mixture was concentrated, the methanol was distilled off, and the residue was diluted with ethyl acetate and washed with water. After drying with $Na_2SO_4$, the organic layer was concentrated to dryness. The dry solid was suspended in acetonitrile under heating, after which it was allowed to cool and collected by filtration to yield 4.2 g of a white crystal, which was purified by silica gel column chromatography (chloroform/ethanol=20:1) to yield 2.8 g of a white crystal.

The filtrate was concentrated and purified by silica gel column chromatography (chloroform/ethanol=20:1) to give 3.2 g of a white crystals. (overall recovery rate 74.6%). Melting point: 216–217° C.

$^1$H-NMR (Acetone-$d_6$); 4.17(q,2H), 4.28(s,2H), 5.14(d, 1H), 5.88(d,1H), 6.7(br-s,1H), 7.17(d,2H), 7.32–7.38(m, 4H), 7.72(s,2H), 7.79(dd,1H), 8.40(d,1H)

EXAMPLE 3
Production of 2-{4-[4-(6-chloronicotinoyl)benzyl]-3,5-dichlorophenyl}-4-methyl-4,5-dihydro-1,2,4-triazin-3(2H)-one (Compound No. 3)

300 mg (0.633 mmol) of 2-{3,5-dichloro-4-[4-(6-chloro-3-nicotinoyl)benzyl]-phenyl)-4,5-dihydro-1,2,4-triazin-3 (2H)-one was dissolved in 9 ml of DMF. After this solution was cooled to 0 to 3° C., 30 mg (60% in oil) of sodium hydride was added at constant temperature, followed by stirring for 15 minutes. While the temperature was kept at 0 to 3° C., 108 mg (0.76 mmol) of methyl iodide was added, followed by stirring at constant temperature for 1 hour. The reaction mixture was poured over water and extracted with ethyl acetate. The extract was dried with $Na_2SO_4$ and concentrated, after which it was purified by silica gel column chromatography (chloroform/ethanol=20:1) to yield 200.2 mg (64.8%) of a brown prismatic crystal.

Melting point: 89–90° C.

$^1$H-NMR (CDCl$_3$); 3.02(s,3H), 4.07(d,2H), 4.39(s,2H), 7.06(t,1H), 7.34(d,2H), 7.46(d,1H), 7.60(s,2H), 7.70(d,2H), 8.06(dd,1H), 8.76(d,1H)

EXAMPLE 4
Production of 4-acetyl-2-{4-[4-(6-chloronicotinoyl)benzyl]-3,5-dichlorophenyl}-4,5-dihydro-1,2,4-triazin-3(2H)-one (Compound No. 4)

100 mg (0.211 mmol) of 2-{3,5-dichloro-4-[4-(6-chloro-3-nicotinoyl)benzyl]phenyl)-4,5-dihydro-1,2,4-triazin-3 (2H)-one and 3 ml of acetic anhydride were mixed and stirred at 140° C. for 1 hour. After concentration, the reaction mixture was diluted with ethyl acetate and washed with water. After drying with $Na_2SO_4$, the organic layer was concentrated and purified by silica gel column chromatography (once with hexane:acetone=1:1, once with chloroform/ethanol=20:1) to yield 90 mg (82.7%) of a yellow crystal.

Melting point: 165–166° C.

$^1$H-NMR (CDCl$_3$); 2.61(s,3H), 4.42(s,2H), 4.49(s,2H), 7.34–7.38(m,3H), 7.47(d,1H), 7.62(s,2H), 7.71(d,2H), 8.07 (dd,1H), 8.77(d,1H)

EXAMPLE 5
Production of 2-{4-[4-(6-chloronicotinoyl)benzyl]-3,5-dichlorophenyl}-4,5-dihydro-1,2,4-triazin-3(2H)-one (Compound No. 1)

2.49 g (5.03 mmol) of 1-benzylidene-2-{4-[4-(6-chloronicotinoyl)benzyl]-3,5-dichlorophenyl}hydrazine was dissolved in 100 ml of ethyl acetate; 1.03 g (7.85 mmol) of 2,2-dimethoxyethyl isocyanate and 30 mg of DBU were added. After stirring at room temperature for 1 hour, 50 mg of DBU was added, followed by stirring for 1 hour. After confirmation of starting material disappearance, 0.53 g (5.23 mmol) of 36% hydrochloric acid was added, followed by stirring for 30 minutes. 0.55 g (5.43 mmol) of 36% hydrochloric acid was then added, followed by stirring for 1.5 hours (a small amount of dark brown resinous substance was formed). After 50 ml of water was added, 50 ml of ethyl acetate was added for liquid layer separation. After water washing, the organic layer was concentrated to yield 3.06 g of a residue. This residue was washed with acetonitrile; 1.32 g of a light yellow-brown crystal was collected by filtration. The filtrate was concentrated and purified by silica gel column chromatography (chloroform/methanol=10/1) to yield 0.69 g of a pale yellow caramel. This substance was combined with the previous crystal, followed by recrystallization to give 1.46 g of crystals having a melting point of 188 to 191° C. (yield: 61.3%).

$^1$H-NMR (CDCl$_3$); 4.12–4.17(m,2H), 4.39(s,2H), 5.44 (br-s,1H), 7.08–7.16(m,1H), 7.34(d,2H), 7.48(d,1H), 7.64(s, 2H), 7.70(d,2H), 8.05(dd,1H), 8.75(d,1H)

EXAMPLE 6
Production of 2-{3,5-dichloro-4-[4-(6-methylthionicotinoyl)benzyl]phenyl}-4,5-dihydro-1,2,4-triazin-3(2H)-one (Compound No. 5)

2.28 g (4.5 mmol) of 1-benzylidene-2-{3,5-dichloro-4-{4-[(6-methylthio)nicotinoyl]benzyl}phenyl}hydrazine was dissolved in 100 ml of ethyl acetate; 0.94 g (7.2 mmol) of 2,2-dimethoxyethyl isocyanate and 30 mg of DBU were added. After stirring at room temperature for 1 hour, 50 mg of DBU was added, followed by stirring for 1.5 hours. After disappearance of the starting materials was confirmed, 0.5 g (4.9 mmol) of 36% hydrochloric acid was added, followed by stirring for 30 minutes; 0.5 g (4.9 mmol) of 36% hydrochloric acid was added, followed by stirring for 2 hours (a small amount of dark brown resinous substance was formed). After addition of 100 ml of water and stirring, liquid layers were separated. The organic layer was concentrated and purified by silica gel column chromatography (chloroform/methanol=10/1) to yield 1.56 g of a pale yellow caramel, which was then recrystallized from ethyl acetate to yield 0.77 g of a light yellow-brown crystal having a melting point of 165 to 167° C. (yield: 35.2%).

$^1$H-NMR (CDCl$_3$); 2.61(s,3H), 4.08–4.16(m,2H), 4.39(s, 2H), 5.50(br-s,1H), 7.08–7.15(m,1H), 7.26(d,1H), 7.32(d, 2H), 7.63(s,2H), 7.69(d,2H), 7.91(dd,1H), 8.80(d,1H)

EXAMPLE 7
Production of 2-{3,5-dichloro-4-[4-(1-hydroxy-1-(2-methylthio-5-pyridyl)ethyl)benzyl]phenyl}-4,5-dihydro-1, 2,4-triazin-3(2H)-one (Compound No. 6)

In a nitrogen stream, 6.2 ml (6.2 mmol) of methylmagnesium bromide (1 mol/l THF solution) was stirred at 5 to 7° C.; 0.6 g (1.24 mmol) of 2-{3,5-dichloro-4-{4-[(6-methylthio)nicotinoyl]benzyl}phenyl}-4,5-dihydro-1,2,4-triazin-3(2H)-one dissolved in 10 ml of tetrahydrofuran (THF) dehydrated with lithium aluminum hydride (LAH) was added drop by drop (30 minutes). After stirring at constant temperature for 1.5 hours, 15 ml of a 10% $NH_4Cl$ solution was added drop by drop (about 13° C.). After stirring for 30 minutes, the reaction mixture was extracted with 20 ml of ethyl acetate; the water layer was further extracted with 15 ml of ethyl acetate. The organic layers were combined and washed with saturated saline, followed by dehydration and concentration. The residue was purified by silica gel column chromatography (chloroform/ methanol=10/1) to yield 0.6 g of a pale yellow caramel (96.8%), which was then recrystallized from ethyl acetate to yield 0.29 g of a pale yellow crystal having a melting point of 208 to 209° C. (46.7%).

The filtrate was concentrated to give 0.18 g of pale yellow crystals (29.0%). Yield 0.47 g (75.8%)

$^1$H-NMR (CDCl$_3$); 1.91(s,3H), 2.19(br-s,1H), 2.54(s,3H), 4.08–4.13(m,2H), 4.27(s,2H), 5.51(br-s,1H), 7.04–7.32(m, 6H), 7.50(dd,1H), 7.58(s,2H), 8.47(d,1H)

EXAMPLE 8

Production of 2-{3,5-dichloro-4-[4-(1-hydroxy-1-(2-chloro-5-pyridyl)ethyl)benzyl]phenyl}-4,5-dihydro-1,2,4-triazin-3(2H)-one (Compound No. 7)

The title compound was produced as a colorless crystal at a yield of 65.3% in a similar manner as Example 7.

Melting point: 205–206° C.

$^1$H-NMR (CDCl$_3$); 1.91(s,3H), 1.98(br-s,1H), 4.06–4.11 (m,2H), 4.27(s,2H), 5.73(br-s,1H), 7.03–7.11(m,1H), 7.15–7.33(m,5H), 7.57(s,2H), 7.63(dd,1H), 8.42(d,1H)

EXAMPLE 9

Production of 2-{3,5-dichloro-4-[4-(1-cyclohexyl-1-hydroxyethyl)benzyl]phenyl}-4,5-dihydro-1,2,4-triazin-3(2H)-one (Compound No. 8)

The title compound was produced as colorless crystals at a recovery rate of 38.0% in a similar manner as Example 7.

Melting point: 107–108° C.

$^1$H-NMR (CDCl$_3$); 0.88–1.83(m,11H), 1.48(s,3H), 2.20 (br-s,1H), 4.10–4.14(m,2H), 4.28(s,2H), 5.48(br-s,1H), 7.05–7.33(m,5H), 7.58(s,2H)

EXAMPLE 10

Production of 2-{3,5-dichloro-4-[4-(1-hydroxy-1-phenylethyl)benzyl]phenyl}-4,5-dihydro-1,2,4-triazin-3(2H)-one (Compound No. 9)

The title compound was produced as a colorless crystal at a yield of 65.8% in a similar manner as Example 7.

Melting point: 161–163° C.

$^1$H-NMR (CDCl$_3$); 1.41(s,3H), 2.20(br-s,1H), 4.06–4.11 (m,2H), 4.27(s,2H),5.69(br-s,1H), 7.00–7.08(m,1H), 7.19–7.44(m,9H), 7.58(s,2H)

EXAMPLE 11

Production of 2-{4-[4-(6-chloronicotinoyl)benzyl]-3-chloro-5-methyl}-4,5-dihydro-1,2,4-triazin-3(2H)-one (Compound No. 10)

2.2 g (3.6 mmol) of 1-benzylidene-2-{4-[4-(6-chloronicotinoyl)benzyl]-3-chloro-5-methylphenyl}-4-(2,2-dimethoxyethyl)semicarbazide was dissolved in 20 ml of ethyl acetate; 0.3 ml (3.6 mmol) of concentrated hydrochloric acid was added at room temperature. After stirring at constant temperature for 1 hour, the crystal precipitated was collected by filtration and washed with a small amount of diethyl ether to give 1.5 g of the title compound. Yield: 91.9%, melting point: 207–208° C. (colorless prismatic crystal)

$^1$H-NMR (CDCl$_3$); 2.28 (s,3H), 4.12 (s,2H), 4.28 (s,2H), 6.33 (s,1H), 7.09 (d,1H), 7.31 (d,1H), 7.46 (d,1H), 7.47 (q,4H), 7.51 (d,1H), 8.06 (dd,1H), 8.76 (d,1H)

EXAMPLE 12

Production of 2-{4-[4-(6-chloronicotinoyl)benzyl]-3-bromo-5-chloro}-4,5-dihydro-1,2,4-triazin-3(2H)-one (Compound No. 11)

The title compound was produced as colorless prismatic crystals at a yield of 86.8% in a similar manner as Example 11.

Melting point: 210–211° C.

$^1$H-NMR (CDCl$_3$); 4.13 (s,2H), 4.44 (s,2H), 6.42 (s,1H), 7.13 (s,1H), 7.46 (d,1H), 7.53 (q,4H), 7.67 (d,1H), 7.80 (d,1H), 8.06 (dd,1H), 8.78 (d,1H)

EXAMPLE 13

Production of 2-{4-[4-(4-chlorobenzoyl)-3-methylbenzyl]-3,5-dichlorophenyl}-4,5-dihydro-1,2,4-triazin-3(2H)-one (Compound No. 12)

The title compound was produced as a colorless needle crystal at a yield of 63.0% in a similar manner as Example 11.

Melting point: 163–164° C.

$^1$H-NMR (CDCl$_3$); 2.30 (s,3H), 4.11 (s,2H), 4.32 (s,2H), 6.40 (br-s,1H), 7.05–7.23 (m,4H), 7.41 (d,2H), 7.61 (s,2H), 7.73 (d,2H)

EXAMPLE 14

Production of 2-{3,5-dichloro-4-[4-(4-methylbenzoyl)benzyl]phenyl}-4,5-dihydro-1,2,4-triazin-3(2H)-one (Compound No. 13)

The title compound was produced as a light yellow crystal at a yield of 47.3% in a similar manner as Example 11.

Melting point: 165–167° C.

$^1$H-NMR (CDCl$_3$); 2.43 (s,3H), 4.14 (t,2H), 4.38 (s,2H), 7.11–7.13 (m,1H), 7.25–7.71 (m,11H)

EXAMPLE 15

Production of 2-{4-[4-(4-chloro-α-hydroxybenzyl)benzyl]-3,5-dichlorophenyl}-4,5-dihydro-1,2,4-triazin-3(2H)-one (Compound No. 14)

170 mg (0.36 mmol) of 2-{4-[4-(4-chlorobenzoyl)benzyl]-3,5-dichlorophenyl}-4,5-dihydro-1,2,4-triazin-3(2H)-one was suspended in 10 ml of methanol; 55 mg (1.45 mmol) of sodium borohydride was added under ice cooling conditions. After this suspension was stirred for 2 hours, 3 ml of 5% hydrochloric acid was added drop by drop, followed by the addition of 20 ml of water. After extraction with 25 ml of ethyl acetate, the water layer was further extracted with 20 ml of ethyl acetate. After washing with saturated saline, the organic layer was dehydrated and concentrated. The resulting colorless syrup was purified by silica gel column chromatography (chloroform/methanol= 10/1) to give 0.12 g of a white caramel, which was then recrystallized from ethyl acetate/hexane; the crystal obtained was stirred in 5 ml of diisopropyl ether at room temperature for 3 hours, after which it was filtered and dried under reduced pressure at 100° C. for 2 hours to give 110 mg of white crystals having a melting point of 173 to 174° C. (64.4%).

$^1$H-NMR (CDCl$_3$); 2.19 (br-s,1H), 4.08–4.13 (m,2H), 4.28 (s,2H), 5.41 (br-s,1H), 5.76 (s,1H), 7.04–7.12 (m,1H), 7.20 (s,4H), 7.29 (s,4H), 7.58 (s,2H)

EXAMPLE 17

Production of 2-{4-[4-(6-chloronicotinoyl)benzyl]-3,5-dichlorophenyl}-1,2,4-triazine-3,5(2H,4H)-dione (Compound No. 16)

0.31 g (0.654 mmol) of 2-{4-[4-(6-chloronicotinoyl)benzyl]-3,5-dichlorophenyl}-4,5-dihydro-1,2,4-triazin-3 (2H)-one and 0.7 g (3.25 mmol) of pyridinium chlorochromate (PCC) was dissolved in 30 ml of THF, followed by stirring at room temperature for 18 hours. The reaction mixture was filtered; the filtrate was concentrated and dissolved in chloroform/methanol (20/1); the insoluble substances were filtered off. The filtrate was concentrated and purified by silica gel column chromatography (chloroform/ethanol=15/1); 0.21 g of the light brown syrup obtained was crystallized from acetonitrile to give 54 mg of white crystals having a melting point of 179 to 181° C. (5.9%).

$^1$H-NMR (CDCl$_3$); 4.44 (s,2H), 7.34 (d,2H), 7.45 (d,1H), 7.60 (s,1H), 7.68 (s,2H), 7.72 (d,2H), 8.06 (dd,1H), 8.75 (d,1H), 9.12 (br-s,1H)

EXAMPLE 18
Production of 2-{4-[4-((6-chloro-3-pyridyl)hydroxymethyl) benzyl]-3,5-dichlorophenyl}-1,2,4-triazine-3,5(2H,4H)-dione (Compound No. 17)

120 mg (0.25 mmol) of 2-{4-[4-(6-chloronicotinoyl) benzyl]-3,5-dichlorophenyl}-1,2,4-triazine-3,5(2H,4H)-dione was suspended in 7 ml of methanol; 40 mg (1.06 mmol) of sodium borohydride was added under ice cooling conditions. After this suspension was stirred for 2 hours, 3 ml of 5% hydrochloric acid was added drop by drop, followed by the addition of 5 ml of water. After extraction with 20 ml of ethyl acetate, the water layer was further extracted with 10 ml of ethyl acetate. After washing with saturated saline, the organic layer was dehydrated and concentrated. The resulting pale yellow syrup was purified by silica gel column chromatography (chloroform/methanol=10/1) to give a white caramel, which was then dried under reduced pressure at 100° C. for 2 hours to give 80 mg of the title compound (yield: 66.4%).

$^1$H-NMR (CDCl$_3$); 2.46(br-s,1H), 4.33(s,2H), 5.81(s,1H), 7.22–7.30(m,5H), 7.57–7.70(m,4H),8.37(d,1H), 9.03(br-s, 1H)

EXAMPLE 19
Production of 2-{3,5-dichloro-4-[4-(6-chloronicotinoyl) benzyl]phenyl}-4-methyl-1,2,4-triazine-3,5(2H,4H)-dione (Compound No. 18)

190 mg (0.39 mmol) of 2-{3,5-dichloro-4-[4-(6-chloro-3-nicotinoyl)benzyl]phenyl}-4-methyl-4,5-dihydro-1,2,4-triazin-3(2H)-one was mixed with 6 ml of dichloromethane; 0.16 g of sodium acetate and 252 mg (1.17 mmol, 3 eq.) of PCC were added, followed by overnight stirring at room temperature. The reaction mixture was filtered; the filtrate was diluted with 50 ml of chloroform and washed with water, after which it was dried with Na$_2$SO$_4$, concentrated, and purified by silica gel column chromatography (chloroform/ethanol=20/1) to give 160 mg of (yield: 81.7%) of whitish yellow prismatic crystals.

Melting point: 70–71° C.

$^1$H-NMR (CDCl$_3$); 3.43(s,3H), 4.45(s,2H), 7.35(d,2H), 7.47(d,1H), 7.61(s,1H), 7.66(s,2H), 7.72(d,2H), 8.07(dd, 1H), 8.76(d,1H)

EXAMPLE 20
Production of 2-{4-[4-(6-chloronicotinoyl)benzyl]-3-chloro-5-methylphenyl}-1,2,4-triazine-3,5(2H,4H)-dione (Compound No. 19)

680 mg (1.5 mmol) of 2-{4-[4-(6-chloronicotinoyl) benzyl]-3-chloro-5-methylphenyl}-4,5-dihydro-1,2,4-triazin-3(2H)-one was dissolved in 30 ml of dichloromethane; 1.3 g (6 mmol) of PCC and 800 mg of sodium acetate were added at room temperature. After this solution was stirred at room temperature overnight, the insoluble substances were filtered off; the filtrate was concentrated. The residue was dissolved by the addition of 30 ml of ethyl acetate; silica gel was added; this solution was again filtered, followed by filtrate concentration. To the residue, 10 ml of acetonitrile was added (crystal precipitated); after stirring at 50° C. for 10 minutes, the crystal precipitated was collected by filtration to give 620 mg of compound No. 19. Yield: 88.5%, melting point: 209–210° C. (colorless and prismatic)

$^1$H-NMR (DMSO-d$_6$); 2.13(s,3H), 4.32(s,2H), 7.40(d, 1H), 7.52(q,4H), 7.57(d,1H), 7.67(s,1H), 7.69(d,1H), 8.15 (dd,1H), 8.71(d,1H), 12.42(s,1H)

EXAMPLE 21
Production of 2-{4-[4-(6-chloronicotinoyl)benzyl]-3-bromo-5-chlorophenyl}-1,2,4-triazine-3,5(2H,4H)-dione (Compound No. 20)

The title compound was produced as a colorless prismatic crystal at a yield of 83.9% in a similar manner as Example 20.

Melting point: 186–187° C.

$^1$H-NMR (DMSO-d$_6$); 4.46(s,2H), 7.56(q,4H), 7.69(d, 1H), 7.71(s,1H), 7.78(d,1H), 7.90(d,1H), 8.15(dd,1H), 8.71 (d,1H), 12.59(s,1H)

EXAMPLE 22
Production of 2-{3,5-dichloro-4-{4-[1-(6-chloro-3-pyridyl) vinyl]benzyl}phenyl}-4,5-dihydro-1,2,4-triazin-3(2H)-one (Compound No. 21)

0.7 g (1.43 mmol) of 2-{3,5-dichloro-4-{4-[1-hydroxy-1-(6-chloro-3-pyridyl)ethyl]benzyl}phenyl}-4,5-dihydro-1,2, 4-triazin-3(2H)-one was suspended in 15 ml of dichloromethane; 0.6 g (4.23 mmol) of boron trifluoride diethyl ether complex was added. After this suspension was stirred at room temperature overnight, 5 ml of dichloromethane and 5 ml of water were added to the reaction mixture, followed by stirring for 30 minutes. The organic layer was separated, washed with water, and dehydrated, after which it was concentrated; the residue was purified by silica gel column chromatography (chloroform/methanol=20/1). The purified product was then recrystallized from acetonitrile to give 0.43 g of the title compound as white crystals having a melting point of 175.5 to 176.5° C. (yield 63.8%).

$^1$H-NMR(CDCl$_3$); 4.10–4.15 (m,2H), 4.31 (s,2H), 5.43 (d,1H), 5.54 (d,1H), 5.72 (br-s,1H), 7.06–7.16 (m,1H), 7.18 (s,4H), 7.25 (d,1H), 7.55 (dd,1H), 7.60 (s,2H), 8.38 (dd,1H)

EXAMPLE 23
Production of 2-{3,5-dichloro-4-{4-[1-(6-methylthio-3-pyridyl)vinyl]benzyl}phenyl}-4,5-dihydro-1,2,4-triazin-3 (2H)-one (Compound No. 22)

From 2-{3,5-dichloro-4-{4-[1-hydroxy-1-(6-methylthio-3-pyridyl)ethyl)benzyl]phenyl}-4,5-dihydro-1,2,4-triazin-3 (2H)-one, the title compound was obtained as white crystals having a melting point of 156 to 157° C. in a similar manner as Example 22 (yield 48.6%)

$^1$H-NMR(CDCl$_3$); 2.58 (s,3H), 4.09–4.14 (m,2H), 4.31 (s,2H), 5.40 (d,1H), 5.45 (d,1H), 5.80 (br-s,1H), 7.06–7.16 (m,2H), 7.19 (s,4H), 7.41 (dd,1H), 7.60 (s,2H), 8.44 (dd,1H)

EXAMPLE 24
Production of 2-{3,5-dichloro-4-[4-(6-chloronicotinoyl) phenylthio]-phenyl}-4,5-dihydro-1,2,4-triazin-3(2H)-one (Compound No. 23)

5.1 g (7.23 mmol) of crude 1-benzylidene-2-{4-[4-(6-chloronicotinoyl)phenylthio]-3,5-dichlorophenyl}-4-(2,2-dimethoxyethyl)semicarbazide as obtained in Reference Example 29 was dissolved in 50 ml of ethyl acetate; 11.5 g of c-HCl was added, followed by stirring at room temperature for 1 hour. Water was added to the reaction mixture, followed by stirring for 30 minutes for liquid layer separation. The water layer was extracted with ethyl acetate; the organic layers were combined, dried with Na$_2$SO$_4$, and concentrated to dryness. The residue was purified by silica gel column chromatography (ethanol:chloroform=1:20); the yellow crystal obtained was suspended in ethyl acetate under heating, and allowed to cool. The crystal precipitated was collected by filtration to give 1.5 g of the title compound as a whitish yellow crystals (yield: 40.0%).

$^1$H-NMR(acetone-d$_6$); 4.15 (t,2H), 5.61(br-s,1H), 7.03–7.19 (m,3H), 7.44 (d,1H), 7.67 (d,2H), 7.85 (s,2H), 7.99 (dd,1H), 8.73 (d,1H)

EXAMPLE 25

Production of 2-{3,5-dichloro-4-{4-[(6-chloro-3-pyridyl) hydroxymethyl)phenylthio}phenyl}-4,5-dihydro-1,2,4-triazin-3(2H)-one (Compound No. 24)

300 mg (0.61 mmol) of 2-{3,5-dichloro-4-[4-(6-chloronicotinoyl)phenylthio]-phenyl}-4,5-dihydro-1,2,4-triazin-3(2H)-one was suspended in a mixture of 10 ml of methanol and 10 ml of chloroform; this suspension was cooled to 3 to 5° C. 76 mg (2.0 mmol) of sodium borohydride was added over a 15-minute period; the reaction mixture was stirred at constant temperature for 2.5 hours. After neutralization with 2 N-HCl aq. under ice cooling conditions, the reaction mixture was concentrated to distill off the methanol, after which the residue was diluted with ethyl acetate and washed with water. The organic layer was dried with $Na_2SO_4$, after which it was concentrated to dryness. The dry solid was suspended in ethyl acetate under heating, after which it was allowed to cool and collected by filtration to give 0.15 mg of the title compound as white crystals (yield: 51.7%).

$^1$H-NMR(Acetone-$d_6$); 4.19 (t,2H), 5.21 (br-s,1H), 5.89 (s,1H), 6.7 (br,1H), 7.09 (d,2H), 7.35–7.38 (m,4H), 7.72 (s,2H), 7.77 (dd,1H), 8.42 (d,1H)

EXAMPLE 26

Production of 2-{3,5-dichloro-4-{4-[(6-chloro-3-pyridyl) ethoxymethyl]benzyl}phenyl}-4,5-dihydro-1,2,4-triazin-3(2H)-one (Compound No. 25)

150 mg (0.32 mmol) of 2-{3,5-dichloro-4-{4-[(6-chloro-3-pyridyl)hydroxymethyl]benzyl}phenyl}-4,5-dihydro-1,2,4-triazin-3(2H)-one was dissolved in 3 ml of chloroform; 110 mg (0.95 mmol) of triethylsilane was added; the solution was cooled to 60° C. To this solution, a mixture of 135 mg (0.95 mmol) of $(C_2H_5)_2OBF_3$ and 1 ml of chloroform was added drop by drop, followed by stirring at constant temperature for 0.5 hours, then at 55 to 60° C. for 8 hours. The reaction mixture was poured over water and extracted with chloroform: the extract was dried with $Na_2SO_4$ and concentrated to dryness. The dry solid was purified by silica gel column chromatography (chloroform:ethanol=20:1) to give 70 mg (yield: 41.9%) of the title compound as white crystals.

$^1$H-NMR(acetone-$d_6$); 1.23 (t,3H), 3.47 (q,2H), 4.15 (t,2H), 4.26 (s,2H), 5.30(s,1H), 5.50 (br-s,1H), 7.03–7.30 (m,6H), 7.45–7.66 (m,3H), 8.31 (d,1H)

EXAMPLE 27

Production of 2-{3,5-dichloro-4-[4-(5-oxazolyl)benzyl] phenyl}-4,5-dihydro-1,2,4-triazin-3(2H)-one (Compound No. 26)

Using 1.5 g of 1-benzylidene-2-[3,5-dichloro-4-(5-oxazolyl)benzyl]phenylhydrazine, 0.8 g of the title compound was produced as colorless prismatic crystals in a similar manner as Example 5.

Melting point: 219–220° C.
$^1$H-NMR(acetone-$d_6$); 3.98 (br-s,2H), 4.25 (s,2H), 7.15 (s,1H), 7.25 (br-s,2H), 7.40–7.90 (m,6H), 8.34 (S,1H)

EXAMPLE 28

Production of 2-{3,5-dichloro-4-[4-(5-oxazolyl)benzyl] phenyl}-1,2,4-triazine-3,5(2H,4H)-dione (Compound No. 27)

Using 0.4 g of 2-[3,5-dichloro-4-[4-(5-oxazolyl)benzyl] phenyl}-4,5-dihydro-1,2,4-triazin-3(2H)-one, 0.08 g of the title compound was produced as colorless prismatic crystals in a similar manner as Example 17.

Melting point: 236–237° C.
$^1$H-NMR(DMSO-$d_6$); 4.33 (s,2H), 7.46 (q,4H), 7.61 (s,1H), 7.70 (s,1H), 7.73 (s,2H), 8.40 (s,1H), 12.48 (s,1H)

EXAMPLE 29

Production of 2-{4-[4-(5,6-dichloronicotinoyl)benzyl]-3,5-dichlorophenyl}-4,5-dihydro-1,2,4-triazin-3(2H)-one (Compound No. 28)

(1) 2,3-Dichloro-5-[4-(2,6-dichloro-4-nitrobenzyl)benzoyl] pyridine

The title compound was prepared as pale yellow crystals at yield of 28.5%, in a similar manner as in Reference Example 1, by the reaction of 5,6-dichloronicotinoylchloride and 4-benzyl-3,5-dichloronitrobenzene.

Melting point: 129–131° C.
$^1$H-NMR(CDCl$_3$); 4.51 (s,2H), 7.34 (d,2H), 7.73 (d,2H), 8.17 (d,1H), 8.26 (s,2H), 8.63 (d,1H)

(2) 5-[4-(4-Amino-2,6-dichlorobenzyl)benzoyl]-2,3-dichloropyridine

The title compound was prepared as pale yellow crystals at yield of 75.9%, in a similar manner as in Reference Example 7, by the reaction of 2,3-dichloro-5-[4-(2,6-dichloro-4-nitrobenzyl)benzoyl]pyrizine and SnCl$_2$.

Melting point: 140–145° C.
$^1$H-NMR(CDCl$_3$); 3.80 (br-s,2H), 4.29 (s,2H), 6.69 (s,2H), 7.33 (d,2H), 7.70 (d,2H), 8.17 (d,1H), 8.64 (d,1H)

(3) 1-Benzylidene-2-{4-[4-(5,6-dichloronicotinoyl)benzyl]-3,5-dichlorophenyl}hydrazine The title compound was prepared as yellow crystals at yield of 98.2%, in a similar manner as in Reference Example 13, by the reaction of 5-[4-(4-amino-2,6-dichlorobenzyl) benzoyl]-2,3-dichloropyridine, NaNO$_2$, SnCl$_2$ and benzaldehyde.

Melting point: 173–175° C.
$^1$H-NMR(CDCl$_3$); 4.33 (s,2H), 7.13 (s,2H), 7.32–7.72 (m,11H), 8.17 (d,1H), 8.64 (d,1H)

(4) 2-{4-(4-(5,6-Dichloronicotinoyl)benzyl]-3,5-dichlorophenyl}-4,5-dihydro-1,2,4-triazin-3(2H)-one (Compound No. 28)

The title compound was prepared as colorless crystals at yield of 34.6%, in a similar manner as in Example 1, by the reaction of 1-benzylidene-2-{4-(4-(5,6-dichloronicotinoyl) benzyl]-3,5-dichlorophenyl}hydrazine and 2,2-dimethoxyethylisocyanate.

Melting point: 192–194° C.
$^1$H-NMR(CDCl$_3$); 4.14 (t,2H), 4.40 (s,2H), 6.04 (br-s, 1H), 7.12–7.14 (m,1H), 7.36 (d,2H), 7.63 (s,2H), 7.71 (d,2H), 8.17 (d,1H), 8.64(d,1H)

EXAMPLE 30

Production of 2-{4-[4-(6-methylnicotinoyl)benzyl]-3,5-dichlorophenyl}-4,5-dihydro-1,2,4-triazin-3(2H)-one (Compound No. 29)

(1) 2-Methyl-5-[4-(2,6-dichloro-4-nitrobenzyl)benzoyl] pyridine

The title compound was prepared as pale yellow crystals at yield of 14.8%, in a similar manner as in Reference Eample 1, by the reaction of 6-methylnicotinoylchloride and 4-benzyl-3,5-dichloronitrobenzene.

Melting point: 121–123° C.
$^1$H-NMR(CDCl$_3$); 2.65 (s,3H), 4.50 (s,2H), 7.29 (d,1H), 7.30 (d,2H), 7.73 (d,2H), 8.01 (dd,1H), 8.25 (s,2H), 8.86 (d,1H)

(2) 5-[4-(4-Amino-2,6-dichlorobenzyl)benzoyl]-2-methylpyridine

The title compound was prepared as colorless crystals at yield of 75.0%, in a similar manner as in Reference Example 7, by the reaction of 2-methyl-5-[4-(2,6-dichloro-4-nitrobenzyl)benzoyl]pyrizine and SnCl$_2$.

Melting point: 153–155° C.

¹H-NMR(CDCl₃); 2.65 (s,3H), 3.80 (br-s,2H), 4.28 (s,2H), 6.68 (s,2H), 7.27 (d,1H), 7.30 (d,2H), 7.71 (d,2H), 8.00 (dd,1H), 8.87 (d,1H)

(3) 1-Benzylidene-2-{4-[4-(6-methylnicotinoyl)benzyl]-3,5-dichlorophenyl}hydrazine The title compound was prepared as pale yellow crystals at yield of 92.0%, in a similar manner as in Reference Example 13, by the reaction of 5-[4-(4-amino-2,6-dichlorobenzyl)benzoyl]-2-methylpyridine, NaNO₂, SnCl₂ and benzaldehyde.

Melting point: 199–201° C.

¹H-NMR(CDCl₃); 2.65 (s,3H), 4.32 (s,2H), 7.12 (s,2H), 7.26–7.81 (m,12H), 8.00 (dd,1H), 8.88 (d,1H)

(4) 2-{4-[4-(6-Methylnicotinoyl)benzyl]-3,5-dichlorophenyl}-4,5-dihydro-1,2,4-triazin-3(2H)-one (Compound No. 29)

The title compound was prepared as colorless crystals at yield of 27.4%, in a similar manner as in Example 1, by the reaction of 1-Benzylidene-2-{4-[4-(6-methylnicotinoyl)benzyl]-3,5-dichlorophenyl}hydrazine and 2,2-dimethoxyethylisocyanate.

Melting point: 121–123° C. (percially), 145° C. (finally)

¹H-NMR(CDCl₃); 2.65 (s,3H), 4.13 (t,2H), 4.39 (s,2H), 6.18 (br-s,1H), 7.11–7.13 (m,1H), 7.28 (d,1H), 7.33 (d,2H), 7.62 (s,2H), 7.71 (d,2H), 7.99 (dd,1H), 8.88 (d,1H)

EXAMPLE 31

Production of 2-{4-[4-(2-chloroisonicotinoyl)benzyl]-3,5-dichlorophenyl}-4,5-dihydro-1,2,4-triazin-3(2H)-one (Compound No. 30)

(1) 2-Chloro-4-[4-(2,6-dichloro-4-nitrobenzyl)benzoyl]pyridine

The title compound was prepared as a yellow oil at yield of 37.8%(crude), in a similar manner as in Reference Example 1, by the reaction of 2-chloronicotinoylchloride and 4-benzyl-3,5-dichloronitrobenzene.

(2) 4-[4-(4-Amino-2,6-dichlorobenzyl)benzoyl]-2-chloropyridine

The title compound was prepared as yellow oil at yield of 91.7%, in a similar manner as in Reference Example 7, by the reaction of 2-chloro-4-[4-(2,6-dichloro-4-nitrobenzyl)benzoyl]pyridine and SnCl₂.

¹H-NMR(CDCl₃); 3.79 (br-s,2H), 4.28 (s,2H), 6.68 (s,2H), 7.32 (d,1H), 7.47 (dd,1H), 7.58 (d,1H), 7.71 (d,2H), 8.55 (d,1H)

(3) 1-Benzylidene-2-{4-[4-(2-chloroisonicotinoyl)benzyl]-3,5-dichlorophenyl}hydrazine The title compound was prepared as yellow oil at yield of 92.0%, in a similar manner as in Reference Example 13, by the reaction of 4-[4-(4-Amino-2,6-dichlorobenzyl)benzoyl]-2-chloropyridine, NaNO₂, SnCl₂ and benzaldehyde.

¹H-NMR(CDCl₃); 4.33 (s,2H), 7.13 (s,2H), 7.32–7.73 (m,13H), 8.54 (d,1H)

(4) 2-{4-[4-(2-Chloroisonicotinoyl)benzyl]-3,5-dichlorophenyl}-4,5-dihydro-1,2,4-triazin-3(2H)-one (Compound No. 30)

The title compound was prepared as colorless crystals at yield of 14.4%, in a similar manner as in Example 1, by the reaction of 1-benzylidene-2-{4-[4-(2-chloroisonicotinoyl)benzyl]-3,5-dichlorophenyl}hydrazine and 2,2-dimethoxyethylisocyanate.

Melting point: 167–169° C.

¹H-NMR(CDCl₃); 4.14 (t,2H), 4.40 (s,2H), 6.23 (br-s, 1H), 7.12–7.14 (m,1H), 7.35 (d,2H), 7.48 (dd,1H), 7.59 (d,1H), 7.63 (s,2H), 7.71 (d,2H), 8.56 (d,1H)

Compound Nos. 34 to 36 and compound Nos. 40 and 41 as shown below were produced in a similar manner as in Example 1.

Compound Nos. 37, 38, 39 and 42 as shown below were produced in a similar manner as in Example 17.

Compound Nos. 31, 32 and 33 as shown below were produced in a similar manner as in Example 2.

Compound No. 31

2-{3-Bromo-5-chloro-4-[4-((6-chloro-3-pyridyl)hydroxymethyl)benzyl]phenyl}-4,5-dihydro-1,2,4-triazin-3(2H)-one Melting point: 219–220° C.

¹H-NMR(d-8 THF): 4.05 (t,2H), 4.33 (s,2H), 5.22 (d,1H), 5.75 (d,1H), 6.86(s,1H) 7.15 (d,2H), 7.18–7.19 (m,1H), 7.28 (d,3H), 7.71 (dd,1H), 7.80 (d,1H), 7.93 (d,1H), 8.40 (d,1H)

Compound No. 32

2-{3-Chloro-4-[4-((6-chloro-3-pyridyl)hydroxymethyl)benzyl-5-methyl]phenyl}-4,5-dihydro-1,2,4-triazin-3(2H)-one Melting point: 187–188° C.

¹H-NMR(CDCl₃): 2.24 (s,3H), 2.96 (br,1H), 4.05 (s,2H), 4.15 (s,2H), 5.74 (s,1H), 5.99 (s,1H), 7.04 (s,1H), 7.17 (q,4H), 7.18 (d,1H), 7.23 (d,1H), 7.44 (d,1H), 7.61 (dd,1H), 8.33 (d,1H)

Compound No. 33

2-{3,5-dichloro-4-[4-(4-methyl-1'-hydroxybenzyl)benzyl]phenyl}-4,5-dihydro-1,2,4-triazin-3(2H)-one Melting point: 163–165° C.

¹H-NMR(CDCl₃): 2.20 (br-s,1H), 2.32 (s,3H), 4.10 (t,2H), 4.27 (s,2H), 5.68 (br-s,1H), 5.77 (s,1H), 7.08–7.09 (m,1H), 7.12–7.27 (m,8H), 7.57 (s,2H)

Compound No. 34

2-{4-[4-(4-Acetylbenzyl)benzyl]-3,5-dichlorophenyl}-4,5-dihydro-1,2,4-triazin-3(2H)-one Melting point: 169–170° C.

¹H-NMR(CDCl3): 2.56 (s,3H), 3.97 (s,2H), 4.08–4.13 (m,2H), 4.26 (s,2H), 5.70 (br-s,1H), 6.98 (m,5H), 7.25 (d,2H), 7.57 (s,2H), 7.86 (d,2H)

Compound No. 35

2-{4-[4-(4-Acetyl-3-methylbenzyl)benzyl]-3,5-dichlorophenyl}-4,5-dihydro-1,2,4-triazin-3(2H)-one Melting point: 191–193° C.

¹H-NMR(CDCl₃): 2.49 (s,3H), 2.54 (s,3H), 3.91 (s,2H), 4.07–4.12 (m,2H), 4.26 (s,2H), 5.86 (br-s,1H), 6.94–7.20 (m,7H), 7.51–7.67 (m,3H)

Compound No. 36

2-{4-[4-(4-Chloro-2-hydroxybenzoyl)benzyl]-3,5-dichlorophenyl}-4,5-dihydro-1,2,4-triazin-3(2H)-one Melting point: 196–197° C.

¹H-NMR(CDCl₃): 4.12–4.17 (m,2H), 4.39 (s,2H), 5.55 (br-s,1H), 6.83 (dd,1H), 7.06–7.16 (m,2H), 7.28–7.62 (m,5H), 7.63 (s,2H), 12.16 (s,1H)

Compound No. 37

2-{3-Bromo-5-chloro-4-[4-((6-chloro-3-pyridyl)hydroxymethyl)benzyl]phenyl}-1,2,4-triazine-3,5(2H,4H)-dione colorless amorphous ¹H-NMR(CDCl₃): 2.86 (s,1H), 4.36 (s,2H), 5.80 (s,1H), 7.21 (q,4H), 7.26 (d,1H), 7.57 (s,1H), 7.64 (dd,1H), 7.65 (d,1H), 7.79 (d,1H), 8.36 (d,1H), 9.68 (s,1H)

Compound No. 38

2-{3-Chloro-4-[4-((6-chloro-3-pyrizyl)hydroxymethyl)benzyl-5-methyl]phenyl}-1,2,4-triazine-3,5(2H,4H)-dione Pale Yellow Amorphous ¹H-NMR(CDCl₃): 2.28 (s,3H), 2.94 (br,1H), 4.19 (s,2H), 5.79 (s,1H), 7.15 (q,4H), 7.23 (d,1H), 7.29 (d,1H), 7.49 (d,1H), 7.55 (s,1H), 7.64 (dd,1H), 8.34 (d,1H), 9.75 (br-s, 1H)

Compound No. 39
2-{3,5-Dichloro-4-[4-(4-methyl-1'-hydroxybenzyl)benzyl]phenyl}-1,2,4-triazine-3,5(2H,4H)-dione
Melting point: 158–160° C.
$^1$H-NMR(CDCl$_3$): 2.20 (br-s,1H), 2.32 (s,3H), 4.31 (s,2H), 5.78 (s,1H), 7.12–7.29 (m,8H), 7.58 (s,1H), 7.61 (s,2H), 8.94 (br-s,1H)

Compound No. 40
2-{4-[4-(6-Chloronicotinoyl)-1'-cyanobenzyl]-3,5-dichlorophenyl}-4,5-dihydro-1,2,4-triazin-3(2H)-one Pale Yellow Caramel
$^1$H-NMR(CDCl$_3$): 4.16 (s,2H), 6.03 (s,1H), 6.25 (s,1H), 7.18 (m,1H), 7.48 (d,1H), 7.66 (q,4H), 7.76 (s,2H), 8.08 (dd,1H), 8.76 (d,1H)

Compound No. 41
2-[3,5-dichloro-4-(4-nicotinoylbenzyl)]phenyl-4,5-dihydro-1,2,4-triazin-3(2H)-one Amorphous
$^1$H-NMR(CDCl$_3$): 4.15 (t,2H), 4.40 (s,2H), 5.46 (br-s, 1H), 7.12 (s,1H), 7.26 (d,1H), 7.62 (d,2H), 7.63 (s,2H), 7.73 (d,2H), 8.08 (m,1H), 8.79 (m,1H), 8.98 (d,1H)

Compound No. 42
2-{4-[4-(4-Chloro-1'-hydroxybenzyl)benzyl]-3,5-dichlorophenyl}-1,2,4-triazine-3,5(2H,4H)-dione
Melting point: 168–170° C.
$^1$H-NMR(CDCl$_3$): 2.26 (br-s,1H), 4.32 (s,2H), 5.76 (s,1H), 7.21 (s,4H), 7.29 (s,4H), 7.57 (s,1H), 7.61 (s,2H), 8.94 (s,1H)

Compound Nos. 43, 45, 48, 49, 51, 52, 54, 56, 58, 59, 61, 63, 65, 67, 69, 71, 73, 75, 77, 79, 81, 83, 85 and 87 as shown below can be produced in a similar manner as Example 2.

Compound Nos. 44, 46, 47, 50, 53, 55, 57, 60, 62, 64, 66, 68, 70, 72, 74, 76, 78, 80, 82, 84 and 86 as shown below can be produced in a similar manner as Example 1.

Compound No. 43
2-{3,5-dichloro-4-[4-((3-pyridyl)hydroxymethyl)benzyl]phenyl}-4,5-dihydro-1,2,4-triazin-3(2H)-one Compound No. 44
2-{3,5-dichloro-4-[4-(3,4,5-trichloro-2-pyridylcarbonyl)benzyl]phenyl}-4,5-dihydro-1,2,4-triazin-3(2H)-one Compound No. 45
2-{3,5-dichloro-4-[4-((3,4,5-trichloro-2-pyridyl)hydroxymethyl)benzyl]phenyl}-4,5-dihydro-1,2,4-triazin-3(2H)-one Compound No. 46
2-{4-[4-(2-Benzoylisonicotinoyl)benzyl]-3,5-dichlorophenyl}-4,5-dihydro-1,2,4-triazin-3(2H)-one Compound No. 47
2-{4-[4-(2,6-Dichloroisonicotinoyl)benzyl]-3,5-dichlorophenyl}-4,5-dihydro-1,2,4-triazin-3(2H)-one Compound No. 48
2-{4-[4-((2,6-Dichloro-3-pyridyl)hydroxymethyl)benzyl]-3,5-dichlorophenyl}-4,5-dihydro-1,2,4-triazin-3(2H)-one Compound No. 49
2-{4-[4-((2-Chloro-3-pyridyl)hydroxymethyl)benzyl]-3,5-dichlorophenyl}-4,5-dihydro-1,2,4-triazin-3(2H)-one Compound No. 50
2-{3,5-Dichloro-4-[4-(6-trifluoromethylnicotinoyl)benzyl]phenyl}-4,5-dihydro-1,2,4-triazin-3(2H)-one Compound No. 51
2-{3,5-Dichloro-4-[4-((6-trifluoromethyl-3-pyridyl)hydroxymethyl)benzyl]phenyl}-4,5-dihydro-1,2,4-triazin-3(2H)-one Compound No. 52
2-{3,5-Dichloro-4-[4-((6-methyl-3-pyridyl)hydroxymethyl)benzyl]phenyl}-4,5-dihydro-1,2,4-triazin-3(2H)-one Compound No. 53
2-{4-[4-(5-Bromonicotinoyl)benzyl]-3,5-dichlorophenyl}-4,5-dihydro-1,2,4-triazin-3(2H)-one Compound No. 54
2-{4-[4-((5-Bromo-3-pyridyl)hydroxymethyl)benzyl]-3,5-dichlorophenyl}-4,5-dihydro-1,2,4-triazin-3(2H)-one Compound No. 55
2-{3,5-dichloro-4-[4-(6-(2',2',2'-trifluoroethyl)nicotinoyl)benzyl]phenyl}-4,5-dihydro-1,2,4-triazin-3(2H)-one Compound No. 56
2-{3,5-dichloro-4-[4-((6-(2,2,2-trifluoroethyl)-3-pyridyl)hydroxy methyl)benzyl]phenyl}-4,5-dihydro-1,2,4-triazin-3(2H)-one Compound No. 57
2-{4-[4-(5-Chloronicotinoyl)benzyl]-3,5-dichlorophenyl}-4,5-dihydro-1,2,4-triazin-3(2H)-one Compound No. 58
2-[4-[4-((5-chloro-3-pyridyl)hydroxymethyl)benzyl]-3,5-dichlorophenyl}-4,5-dihydro-1,2,4-triazin-3(2H)-one Compound No. 59
2-{3,5-dichloro-4-[4-((5,6-Dichloro-3-pyridyl)hydroxymethyl)benzyl]phenyl}-4,5-dihydro-1,2,4-triazin-3(2H)-one Compound No. 60
2-{3,5-dichloro-4-[4-(6-(1-pyrazolyl)nicotinoyl)benzyl]phenyl}-4,5-dihydro-1,2,4-triazin-3(2H)-one Compound No. 61
2-{3,5-dichloro-4-[4-((6-(1-pyrazolyl)-3-pyridyl)hydroxymethyl)benzyl]phenyl}-4,5-dihydro-1,2,4-triazin-3(2H)-one Compound No. 62
2-{3,5-dichloro-4-[4-(6-(1-imidazolyl)nicotinoyl)benzyl]phenyl}-4,5-dihydro-1,2,4-triazin-3(2H)-one Compound No. 63
2-{3,5-dichloro-4-[4-((6-(1-imidazolyl)-3-pyridyl)hydroxymethyl)benzyl]phenyl}-4,5-dihydro-1,2,4-triazin-3(2H)-one Compound No. 64
2-{3,5-dichloro-4-[4-(6-(1-triazolyl)nicotinoyl)benzyl]phenyl}-4,5-dihydro-1,2,4-triazin-3(2H)-one Compound No. 65
2-{3,5-dichloro-4-[4-((6-(1-triazolyl)-3-pyridyl)hydroxymethyl)benzyl]phenyl}-4,5-dihydro-1,2,4-triazin-3(2H)-one Compound No. 66
2-[3,5-Dichloro-4-(4-isonicotinoylbenzyl)phenyl]-4,5-dihydro-1,2,4-triazin-3(2H)-one Compound No. 67
2-{3,5-Dichloro-4-[4-((3-pyridyl)hydroxymethyl)benzyl]phenyl}-4,5-dihydro-1,2,4-triazin-3(2H)-one Compound No. 68
2-{3,5-Dichloro-4-[4-(2-thienylcarbonyl)benzyl]phenyl}-4,5-dihydro-1,2,4-triazin-3(2H)-one Compound No. 69
2-{3,5-Dichloro-4-[4-((2-thienyl)hydroxymethyl)benzyl]phenyl}-4,5-dihydro-1,2,4-triazin-3(2H)-one Compound No. 70
2-{3,5-Dichloro-4-[4-(2-pyrrolylcarbonyl)benzyl]phenyl}-4,5-dihydro-1,2,4-triazin-3(2H)-one Compound No. 71
2-{3,5-Dichloro-4-[4-((2-pyrrolyl)hydroxymethyl)benzyl]phenyl}-4,5-dihydro-1,2,4-triazin-3(2H)-one Compound No. 72
2-{3,5-Dichloro-4-[4-(5-imidazolylcarbonyl)benzyl]phenyl}-4,5-dihydro-1,2,4-triazin-3(2H)-one Compound No. 73
2-{3,5-Dichloro-4-[4-((5-imidazolyl)hydroxymethyl)benzyl]phenyl}-4,5-dihydro-1,2,4-triazin-3(2H)-one Compound No. 74
2-{3,5-Dichloro-4-[4-((3-pyrazolyl)carbonyl)benzyl]phenyl}-4,5-dihydro-1,2,4-triazin-3(2H)-one Compound No. 75
2-{3,5-Dichloro-4-[4-((3-pyrazolyl)hydroxymethyl)benzyl]phenyl}-4,5-dihydro-1,2,4-triazin-3(2H)-one Compound No. 76
2-{3,5-Dichloro-4-[4-((2-indolyl)carbonyl)benzyl]phenyl}-4,5-dihydro-1,2,4-triazin-3(2H)-one Compound No. 77
2-{3,5-Dichloro-4-[4-((2-indolyl)hydroxymethyl)benzyl]phenyl}-4,5-dihydro-1,2,4-triazin-3(2H)-one Compound No. 78
2-{3,5-Dichloro-4-[4-((3-indolyl)carbonyl)benzyl]phenyl}-4,5-dihydro-1,2,4-triazin-3(2H)-one Compound No. 79
2-{3,5-Dichloro-4-[4-((3-indolyl)hydroxymethyl)benzyl]phenyl}-4,5-dihydro-1,2,4-triazin-3(2H)-one Compound No. 80
2-{3,5-Dichloro-4-[4-((1-isoquinolinyl)carbonyl)benzyl]phenyl}-4,5-dihydro-1,2,4-triazin-3(2H)-one Compound No. 81
2-{3,5-Dichloro-4-[4-((1-isoquinolinyl)hydroxymethyl)benzyl]phenyl}-4,5-dihydro-1,2,4-triazin-3(2H)-one Compound No. 82
2-{3,5-Dichloro-4-[4-((2-quinolinyl)carbonyl)benzyl]phenyl}-4,5-dihydro-1,2,4-triazin-3(2H)-one Compound No. 83
2-{3,5-Dichloro-4-(4-((2-quinolinyl)hydroxymethyl)benzyl]phenyl}-4,5-dihydro-1,2,4-triazin-3(2H)-one Compound No. 84
2-{3,5-Dichloro-4-[4-((3-quinolinyl)carbonyl)benzyl]phenyl}-4,5-dihydro-1,2,4-triazin-3(2H)-one Compound No. 85
2-{3,5-Dichloro-4-[4-((3-quinolinyl)hydroxymethyl)benzyl]phenyl}-4,5-dihydro-1,2,4-triazin-3(2H)-one Compound No. 86
2-{3,5-Dichloro-4-[4-((2-quinoxalinyl)carbonyl)benzyl]phenyl}-4,5-dihydro-1,2,4-triazin-3(2H)-one Compound No. 87
2-{3,5-Dichloro-4-[4-((2-quinoxalinyl)hydroxymethyl)benzyl]phenyl}-4,5-dihydro-1,2,4-triazin-3(2H)-one

BIOLOGICAL TESTS

Test Example 1

The potency of the compound of the present invention against coccidia was tested in chicks. Using 9-day-old male White Leghorn chicks in groups of 3, the birds in all the test groups other than an uninfected and untreated control group were orally inoculated with $5 \times 10^4$ sporulating oocysts of a laboratory strain of Eimeria tenella per bird. As the test drug, the compound of the invention, dried and pulverized, was added to the standard ration (SDL No. 1, Nippon Formula Feed) at the level of 31.3 ppm and the medicated diet was given ad libitum for 9 days from 24 hours before infection to day 8 after infection. During the period, the chiks were weighed and bloody droppings were counted. In addition, the number of oocysts was determined for evaluation of anticoccidial efficacy.

The results are shown in Table 1.

TABLE 1

| Compound No. | Relative body weight gain (%) | Number of bloody droppings[2] | OPG (log)[3] |
|---|---|---|---|
| Non-infected/treatment group | 100 | 0 | ND[4] |
| Infected/untreated control group | 7 | 9 | 5.1 |
| 1 | 102 | 0 | ND |
| 2 | 100 | 0 | ND |
| 3 | 101 | 0 | ND |
| 4 | 102 | 0 | ND |
| 5 | 98 | 0 | ND |
| 6 | 99 | 0 | ND |
| 7 | 100 | 0 | ND |
| 8 | 97 | 0 | ND |
| 9 | 98 | 0 | ND |
| 10 | 103 | 0 | ND |
| 11 | 100 | 0 | ND |
| 14 | 100 | 0 | ND |
| 15 | 103 | 0 | ND |
| 16 | 102 | 0 | ND |
| 17 | 101 | 0 | ND |
| 18 | 100 | 0 | ND |
| 19 | 104 | 0 | ND |
| 20 | 98 | 0 | ND |

It is apparent from Table 1, as compared with the infected control group, the groups treated with the compound of the present invention showed increased body weight gains, indicating the excellent anticoccidial activity of the compound.

1) Relative body weight gain = $\dfrac{\text{Mean body weight gain in each test group}}{\text{Mean body weight gain in uninfected control group}} \times 100$ 2) Number of bloody droppings: The quantity of bloody stool discharged from the chick's intestinal canal was shown in the number of blood stains/bird on the litter on the peak day.

3) OPG: The number of oocysts excreted in each gram of stool (on day 7 after infection)

4) ND: not detected

Formulation Example 1

2-{4-[4-(6-chloronicotinoyl)benzyl]-3,5-dichlorophenyl}-4,5-dihydro-1,2,4-triazin-3(2H)-one (compound No. 1), 25 g, is weighed and pulverized to 100% under screen (355 μm) and mixed evenly with 975 g of rice bran and oil cake (1:1).

What is claimed is:
1. A compound represented by the formula:

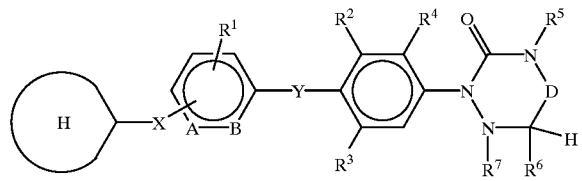

wherein ring H represents an aromatic heterocyclic group selected from the group of pyrrolyl, pyrazolyl, imidazolyl, triazolyl, tetrazolyl, furyl, thienyl, thienyl in which the sulfur atom is oxidized, oxazolyl, isoxazolyl, oxadiazolyl, thiazolyl, isothiazolyl, thiadiazolyl, pyridyl, pyridyl in which the nitrogen atom is oxidized, pyridazinyl, pyridazinyl in which one or both of the nitrogen atoms are oxidized, pyrimidinyl, pyrimidinyl in which one or both of the nitrogen atoms are oxidized, pyrazinyl, indolyl, quinolyl, isoquinolyl, pyrido[2,3-d]pyrimidinyl, naphthyridinyl, quinoxalinyl, thieno[2,3-d]pyridyl, pyrazinoquinolyl, chromenyl, imidazo[1,2-a]pyridyl, imidazo[2,1-b]thiazolyl, imidazo[1,2-a]pyrimidinyl, imidazo[1,2-b]pyridazinyl, imidazo[1,2-a]imidazolyl, imidazo[2,1-b](1,3,4)thiadiazolyl, pyrazolo[1,5-a]pyrimidinyl, pyrazolo[5,1-b]thiazolyl or pyrazolo[1,5-a]pyridyl, or said ring H represents an alicyclic hydrocarbon group selected from the group of a $C_{3-14}$ cycloalkyl group or a $C_{3-14}$ cycloalkenyl group; and further wherein said aromatic heterocyclic group or alicyclic hydrocarbon group may be optionally substituted with one to four substituents selected from the group of hydroxy, amino, cyano, sulfamoyl, sulfamoyloxy, sulfo, mercapto, nitro, oxo, thioxo, halogen, or hydrocarbon group selected from the group consisting of (i) a $C_{1-6}$ alkyl group, (ii) a $C_{3-14}$ cycloalkyl group, (iii) a $C_{2-6}$ alkenyl group, (iv) a $C_{3-14}$ cycloalkenyl group, (v) a $C_{2-6}$ alkynyl group, (vi) a $C_{6-14}$ aryl group and (vii) a $C_{7-19}$ aralkyl group, and wherein said hydrocarbon group may be optionally substituted with one to five substituents selected from halogen and hydroxy, a hydrocarbon-oxy group, a hydrocarbon-thio group, a benzoyl group and a 5-membered or 6-membered heterocyclic group, said halogen includes fluorine, chlorine, bromine, or iodine; and X and Y independently represent a single bond, —O—, a group of the formula: —S(O)$_m$— wherein m is 0, 1 or 2, a group of the formula: —NR$^8$— wherein R$^8$ represents a hydrogen atom, an alkyl group where said alkyl group comprises a straight-chain or branched alkyl group of 1 to 6 carbon atoms, or an acyl group selected from the group of $C_{1-7}$ alkanoyl group, $C_{6-14}$ arylcarbonyl group, $C_{1-6}$ alkoxy-carbonyl group, $C_{6-14}$ aryloxy-carbonyl, $C_{7-19}$ aralakyloxycarbonyl, $C_{7-19}$ aralkyloxycarbonyl, pyrrolylcarbonyl, pyrazolylcarbonyl, imidazolylcarbonyl, triazolylcarbonyl, furylcarbonyl, thienylcarbonyl, oxazolylcarbonyl, isoxazolylcarbonyl, oxadiazolylcarbonyl, thiazolylcarbonyl, isothiazolylcarbonyl, thiadiazolylcarbonyl, pyrrolidinylcarbonyl, pyridylcarbonyl, pyridylcarbonyl in which one or both nitrogen atoms are oxidized, pyridazinylcarbonyl, pyridazinylcarbonyl in which one or both nitrogen atoms are oxidized, pyrimidinylcarbonyl, pyrimidinylcarbonyl in which one or both of the nitrogen atoms are oxidized, pyrazinylcarbonyl, piperidinylcarbonyl, piperazinylcarbonyl, indolylcarbonyl, pyranylcarbonyl, thiopyranylcarbonyl, quinolylcarbonyl, isoquinolylcarbonyl, pyrido[2,3-d]pyrimidinylcarbonyl, naphthyridinylcarbonyl, pyrazinoquinolylcarbonyl, chromenylcarbonyl, 2-pyrrolylacetyl, 3-imidazolylacetyl, or 5-isoxazolylacetyl, —CO— or a methylene group;

—A—B— represents —N=CH—, —CH=N—, —N=N— or —CH=CH—;

R$^1$ represents a hydrogen atom, a halogen atom, a $C_{1-6}$ alkyl group which may be bonded through a hetero atom selected from the group of a nitrogen atom, an oxygen atom or a sulfur atom or a $C_{1-20}$ acyl group;

R$^2$ and R$^3$ independently represent a hydrogen atom, a halogen atom or a $C_{1-6}$ alkyl group;

R$^4$ represents a hydrogen atom or a halogen atom;

R$^5$ represents a hydrogen atom, a $C_{1-6}$ alkyl group or a $C_{1-20}$ acyl group;

R$^6$ and R$^7$ independently represent a hydrogen atom or R$^6$ and R$^7$ may form a chemical bond together with each other comprising a group of the formula:

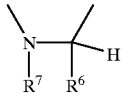

or a group of the formula:

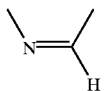

and D represents —CH$_2$— or —CO—; or a salt thereof.

2. The compound as claimed in claim 1 or a salt thereof wherein ring H is a 5- or 6-membered aromatic heterocyclic group, a condensed ring group of a 5- or 6-membered aromatic heterocyclic ring further with a benzene ring or a 5- or 6-membered aromatic heterocyclic ring, a $C_{3-14}$ cycloalkyl group or a $C_{3-14}$ cycloalkenyl group.

3. The compound as claimed in claim 1 or a salt thereof wherein R$^8$ is a hydrogen atom, a $C_{1-6}$ alkyl group or an $C_{1-20}$ acyl group.

4. The compound as claimed in claim 1 or a salt thereof wherein said methylene may be optionally substituted with a substituent selected from the group of (1) a $C_{1-6}$ alkyl group which may optionally be substituted with (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxy-imino group or (ix) hydroxyimino, (2) halogen, (3) a $C_{1-6}$ alkoxy group, (4) a $C_{1-6}$ alkylidene group, (5) hydroxy, (6) cyano, (7) a carbamoyloxy group which may optionally be substituted with a $C_{1-6}$ alkyl group or a $C_{6-14}$ aryl group, (8) a $C_{1-20}$ acyloxy group, (9) a $C_{1-6}$ alkylsulfonyloxy group and (10) a $C_{6-14}$ arylsulfonyloxy group.

5. The compound as claimed in claim 1 or a salt thereof wherein said alkyl group of said R$^1$ may be optionally substituted with a substituent selected from the group of (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group and (ix) hydroxyimino, and which may be bonded through a nitrogen atom, an oxygen atom or a sulfur atom or (4) a $C_{1-20}$ acyl group.

6. The compound as claimed in claim 1 or a salt thereof wherein said alkyl group of said R$^2$ and said R$^3$ may optionally be substituted with a substituent selected from the group of methyl, ethyl, n-propyl or isoproyl; preferably a $C_{1-3}$ alkyl group, and wherein said alkyl group may be optionally substituted with one to three substituents selected from the group of a hydroxy, an alkylthio wherein said alkylthio may be selected from the group consisting of methylthio, ethylthio, n-propylthio or isopropylthio, a halogen wherein said halogen may be selected from the group of fluorine, chlorine, bromine, or iodine, an alkoxy wherein said alkoxy may be a $C_{1-6}$ alkoxy selected from the group of methoxy, ethoxy, n-propoxy, tert-butoxy, or n-hexyloxy, a nitro, an alkoxycarbonyl wherein said alkoxycarbonyl may be a $C_{1-6}$ alkoxycarbonyl selected from the group of methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl, an alkylamino wherein said alkylamino may be a mono-$C_{1-6}$ or di-$C_{1-6}$ alkylamino selected from the group of methylamino, ethylamino, n-propylamino, n-butylamino, tert-butylamino, n-pentylamino, n-hexylamino, dimethylamino, diethylamino, methylethylamino, di-(n-propyl)amino, or di-(n-butyl)amino, an alkoxyimino wherein said alkoxyimino may be a $C_{1-6}$ alkoxyimino selected from the group of methoxyimino, ethoxyimino, n-propoxyimino, tert-butoxyimino or n-hexyloximino, and an hydroxyimino.

7. The compound as claimed in claim 1 or a salt thereof wherein said alkyl group of said $R^5$ may optionally be substituted with a substituent selected from the group of methyl, ethyl, n-propyl or isoproyl; a $C_{1-3}$ alkyl group, and wherein said alkyl group may be optionally substituted with one to three substituents selected from the group of a hydroxy, an alkylthio wherein said alkylthio may be selected from the group consisting of methylthio, ethylthio, n-propylthio or isopropylthio, a halogen wherein said halogen may be selected from the group of fluorine, chlorine, bromine, or iodine, an alkoxy wherein said alkoxy may be a $C_{1-6}$ alkoxy selected from the group of methoxy, ethoxy, n-propoxy, tert-butoxy, or n-hexyloxy, a nitro, an alkoxycarbonyl wherein said alkoxycarbonyl may be a $C_{1-6}$ alkoxycarbonyl selected from the group of methoxycarbonyl, ethoxycarbonyl, n-propoxycarbonyl, isopropoxycarbonyl, n-butoxycarbonyl, isobutoxycarbonyl, sec-butoxycarbonyl or tert-butoxycarbonyl, an alkylamino wherein said alkylamino may be a mono-$C_{1-6}$ or di-$C_{1-6}$ alkylamino selected from the group of methylamino, ethylamino, n-propylamino, n-butylamino, tert-butylamino, n-pentylamino, n-hexylamino, dimethylamino, diethylamino, methylethylamino, di-(n-propyl)amino, or di-(n-butyl)amino, an alkoxyimino wherein said alkoxyimino may be a $C_{1-6}$ alkoxyimino selected from the group of methoxyimino, ethoxyimino, n-propoxyimino, tert-butoxyimino or n-hexyloximino, and an hydroxyimino.

8. The compound as claimed in claim 1 or a salt thereof wherein the ring H is a pyridyl group, an oxazolyl group, a thienyl group, a pyrrolyl group, an imidazolyl group, a pyrazolyl group, an indolyl group, an isoquinolyl group, a quinolyl group, a quinoxalinyl group or a $C_{3-14}$ cycloalkyl group, each of which may optionally be substituted with halogen, a $C_{1-6}$ alkylthio group, a $C_{1-6}$ alkyl group which may optionally be substituted with halogen, a benzoyl group, an α-hydroxybenzyl group, a pyrazolyl group, an imidazolyl group, or a triazolyl group; X is (1) —CO—, (2) a methylene group which may optionally be substituted with a substituent selected from the group consisting of (i) hydroxy, (ii) a $C_{1-6}$ alkyl group, (iii) a $C_{1-6}$ alkylidene group and (iv) a $C_{1-6}$ alkoxy group or (3) a single bond; Y is a methylene group or —S—; —A—B— is —CH=CH—; $R^1$ is a hydrogen atom; $R^2$ and $R^3$ are independently a halogen atom or a $C_{1-6}$ alkyl group; $R^4$ is a hydrogen atom; $R^5$ is a hydrogen atom, a $C_{1-6}$ alkyl group or a $C_{1-7}$ alkanoyl group; $R^6$ and $R^7$ form a chemical bond together with each other.

9. The compound as claimed in claim 1 which is 2-{4-[4-(6-chloronicotinoyl)-benzyl]-3,5-dichlorophenyl}-4,5-dihydro-1,2,4-triazin-3(2H)-one or a salt thereof.

10. The compound as claimed in claim 1 which is 2-{4-[4-((6-chloro-3-pyridyl)hydroxymethyl)benzyl]-3,5-dichlorophenyl}-4,5-dihydro-1,2,4-triazin-3(2H)-one or a salt thereof.

11. The compound as claimed in claim 1 which is 2-{4-[4-(6-chloronicotinoyl)benzyl]-3,5-dichlorophenyl}-1,2,4-triazine-3,5(2H,4H)-dione or 2-{4-[4-((6-chloro-3-pyridyl)hydroxymethyl)benzyl]-3,5-dichlorophenyl}-1,2,4-triazine-3,5(2H,4H)-dione, or a salt thereof.

12. A compound represented by the formula:

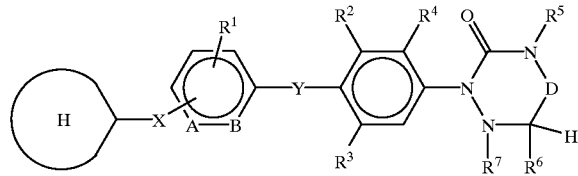

wherein ring H is a phenyl group which may optionally be substituted with halogen and/or hydroxy;

X is a methylene group which may optionally be substituted with a substituent selected from the group consisting of a $C_{1-6}$ alkyl group and hydroxy;

Y is a single bond, —O—, a group of the formula: —S(O)$_m$— wherein m is 0, 1 or 2, a group of the formula: —NR$^8$— wherein R$^8$ is a hydrogen atom, an alkyl group where said alkyl group comprises a straight-chain or branched alkyl group of 1 to 6 carbon atoms, or an acyl group selected from the group of $C_{1-7}$ alkanoyl group, $C_{6-14}$ aryl-carbonyl group, $C_{1-6}$ alkoxy-carbonyl group, $C_{6-14}$ aryloxy-carbonyl, $C_{7-19}$ aralakyloxycarbonyl, $C_{7-19}$aralkyloxycarbonyl, pyrrolylcarbonyl, pyrazolylcarbonyl, imidazolylcarbonyl, triazolylcarbonyl, furylcarbonyl, thienylcarbonyl, oxazolylcarbonyl, isoxazolylcarbonyl, oxadiazolylcarbonyl, thiazolylcarbonyl, isothiazolylcarbonyl, thiadiazolylcarbonyl, pyrrolidinylcarbonyl, pyridylcarbonyl, pyridylcarbonyl in which one or both nitrogen atoms are oxidized, pyridazinylcarbonyl, pyridazinylcarbonyl in which one or both nitrogen atoms are oxidized, pyrimidinylcarbonyl, pyrimidinylcarbonyl in which one or both of the nitrogen atoms are oxidized, pyrazinylcarbonyl, piperidinylcarbonyl, piperazinylcarbonyl, indolylcarbonyl, pyranylcarbonyl, thiopyranylcarbonyl, quinolylcarbonyl, isoquinolylcarbonyl, pyrido[2,3-d]pyrimidinylcarbonyl, naphthyridinylcarbonyl, pyrazinoquinolylcarbonyl, chromenylcarbonyl, 2-pyrrolylacetyl, 3-imidazolylacetyl, or 5-isoxazolylacetyl, —CO— or a methylene group wherein said methylene group may be optionally substituted with a substituent selected from the group of (1) a $C_{1-6}$ alkyl group which may optionally be substituted with (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group or (ix) hydroxyimino, (2) halogen, (3) a $C_{1-6}$ alkoxy group, (4) a $C_{1-6}$ alkylidene group, (5) hydroxy, (6) cyano, (7) a carbamoyloxy group which may optionally be substituted with a $C_{1-6}$ alkyl group or a $C_{6-14}$ aryl group, (8) a $C_{1-20}$ acyloxy group, (9) a $C_{1-6}$ alkylsulfonyloxy group and (10) a $C_{6-14}$ arylsulfonyloxy group;

—A—B— is —N=CH—, —CH=N—, —N=N— or —CH=CH—;

$R^1$ is a hydrogen atom, a halogen atom, a $C_{1-6}$ alkyl group which may be bonded through a hetero atom wherein said hetero atom is selected from the group of nitrogen, oxygen or sulfur, or a $C_{1-20}$ acyl group;

$R^2$ and $R^3$ are independently a hydrogen atom, a halogen atom or a $C_{1-6}$ alkyl group;

$R^4$ is a hydrogen atom or a halogen atom;

$R^5$ is a hydrogen atom, a $C_{1-6}$ alkyl group or a $C_{1-20}$ acyl group;

$R^6$ and $R^7$ are independently a hydrogen atom or $R^6$ and $R^7$ may form a chemical bond together with each other comprising a group of the formula:

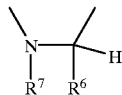

or a group of the formula:

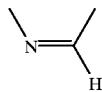

and D is —CH$_2$—; or a salt thereof.

13. A compound represented by the formula:

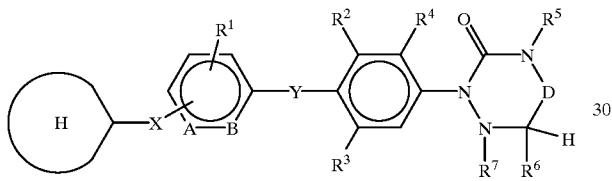

wherein ring H is a phenyl group which may optionally be substituted with halogen and/or hydroxy;

X and Y are independently a single bond, —O—, a group of the formula: —S(O)$_m$— wherein m is 0, 1 or 2, a group of the formula: —NR$^8$— wherein R$^8$ is a hydrogen atom, an alkyl group where said alkyl group comprises a straight-chain or branched alkyl group of 1 to 6 carbon atoms, or an acyl group selected from the group of $C_{1-7}$ alkanoyl group, $C_{6-14}$ aryl-carbonyl group, $C_{1-6}$ alkoxy-carbonyl group, $C_{6-14}$ aryloxycarbonyl, $C_{7-19}$ aralakyloxycarbonyl, $C_{7-19}$aralkyloxycarbonyl, pyrrolylcarbonyl, pyrazolylcarbonyl, imidazolylcarbonyl, triazolylcarbonyl, furylcarbonyl, thienylcarbonyl, oxazolylcarbonyl, isoxazolylcarbonyl, oxadiazolylcarbonyl, thiazolylcarbonyl, isothiazolylcarbonyl, thiadiazolylcarbonyl, pyrrolidinylcarbonyl, pyridylcarbonyl, pyridylcarbonyl in which one or both nitrogen atoms are oxidized, pyridazinylcarbonyl, pyridazinylcarbonyl in which one or both nitrogen atoms are oxidized, pyrimidinylcarbonyl, pyrimidinylcarbonyl in which one or both of the nitrogen atoms are oxidized, pyrazinylcarbonyl, piperidinylcarbonyl, piperazinylcarbonyl, indolylcarbonyl, pyranylcarbonyl, thiopyranylcarbonyl, quinolylcarbonyl, isoquinolylcarbonyl, pyrido[2,3-d]pyrimidinylcarbonyl, naphthyridinylcarbonyl, pyrazinoquinolylcarbonyl, chromenylcarbonyl, 2-pyrrolylacetyl, 3-imidazolylacetyl, or 5-isoxazolylacetyl, —CO— or a methylene group wherein said methylene group may be optionally substituted with a substituent selected from the group of (1) a $C_{1-6}$ alkyl group which may optionally be substituted with (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group or (ix) hydroxyimino, (2) halogen, (3) a $C_{1-6}$ alkoxy group, (4) a $C_{1-6}$ alkylidene group, (5) hydroxy, (6) cyano, (7) a carbamoyloxy group which may optionally be substituted with a $C_{1-6}$ alkyl group or a $C_{6-14}$ aryl group, (8) a $C_{1-20}$ acyloxy group, (9) a $C_{1-6}$ alkylsulfonyloxy group and (10) a $C_{6-14}$ arylsulfonyloxy group;

—A—B— is —N=CH—, —CH=N—, —N=N— or —CH=CH—;

$R^1$ is a $C_{1-6}$ alkyl group;

$R^2$ and $R^3$ are independently a hydrogen atom, a halogen atom or a $C_{1-6}$ alkyl group;

$R^4$ is a hydrogen atom or a halogen atom;

$R^5$ is a hydrogen atom, a $C_{1-6}$ alkyl group or a $C_{1-20}$ acyl group;

$R^6$ and $R^7$ are independently a hydrogen atom or $R^6$ and $R^7$ may form a chemical bond together with each other comprising a group of the formula:

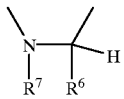

or a group of the formula:

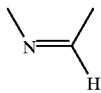

and D is —CH$_2$—; or a salt thereof.

14. A compound represented by the formula:

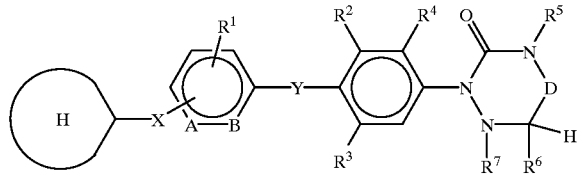

wherein ring H is a phenyl group which is substituted with one to three substituents selected from the group consisting of a $C_{1-6}$ alkyl group and a $C_{1-6}$ alkyl-carbonyl group;

X and Y are independently a single bond, —O—, a group of the formula: —S(O)$_m$— wherein m is 0, 1 or 2, a group of the formula: —NR$^8$— wherein R$^8$ is a hydrogen atom, an alkyl group where said alkyl group comprises a straight-chain or branched alkyl group of 1 to 6 carbon atoms, or an acyl group selected from the group of $C_{1-7}$ alkanoyl group, $C_{6-14}$ aryl-carbonyl group, $C_{1-6}$ alkoxy-carbonyl group, $C_{6-14}$ aryloxycarbonyl, $C_{7-19}$ aralakyloxycarbonyl, $C_{7-19}$aralkyloxycarbonyl, pyrrolylcarbonyl, pyrazolylcarbonyl, imidazolylcarbonyl, triazolylcarbonyl, furylcarbonyl, thienylcarbonyl, oxazolylcarbonyl, isoxazolylcarbonyl, oxadiazolylcarbonyl, thiazolylcarbonyl, isothiazolylcarbonyl, thiadiazolylcarbonyl, pyrrolidinylcarbonyl, pyridylcarbonyl, pyridylcarbonyl in which one or both nitrogen atoms are oxidized, pyridazinylcarbonyl, pyridazinylcarbonyl in which one or both nitrogen atoms are oxidized, pyrimidinylcarbonyl, pyrimidinylcarbonyl in which one or both of the nitrogen atoms are oxidized, pyrazinylcarbonyl, piperidinylcarbonyl, piperazinylcarbonyl, indolylcarbonyl, pyranylcarbonyl, thiopyranylcarbonyl, quinolylcarbonyl, isoquinolylcarbonyl, pyrido[2,3-d]pyrimidinylcarbonyl, naphthyridinylcarbonyl, pyrazinoquinolylcarbonyl, chromenylcarbonyl, 2-pyrrolylacetyl, 3-imidazolylacetyl, or 5-isoxazolylacetyl, —CO— or a methylene group wherein said methylene group may be optionally substituted with a substituent selected from the group of (1) a $C_{1-6}$ alkyl group which may optionally be substituted with (i) hydroxy, (ii) a $C_{1-4}$ alkylthio group, (iii) halogen, (iv) a $C_{1-6}$ alkoxy group, (v) nitro, (vi) a $C_{1-6}$ alkoxy-carbonyl group, (vii) a mono- or di-$C_{1-6}$ alkylamino group, (viii) a $C_{1-6}$ alkoxyimino group or (ix) hydroxyimino, (2) halogen, (3) a $C_{1-6}$ alkoxy group, (4) a $C_{1-6}$ alkylidene group, (5) hydroxy, (6) cyano, (7) a carbamoyloxy group which may optionally be substituted with a $C_{1-6}$ alkyl group or a $C_{6-14}$ aryl group, (8) a $C_{1-20}$ acyloxy group, (9) a $C_{1-6}$ alkylsulfonyloxy group and (10) a $C_{6-14}$ arylsulfonyloxy group;

—A—B— is —N=CH—, —CH=N—, —N=N— or —CH=CH—;

$R^1$ is a hydrogen atom, a halogen atom, a $C_{1-6}$ alkyl group which may be bonded through a hetero atom wherein said hetero atom is selected from the group of nitrogen, oxygen, or sulfur, or a $C_{1-20}$ acyl group;

$R^2$ and $R^3$ are independently a hydrogen atom, a halogen atom or a $C_{1-6}$ alkyl group;

$R^4$ is a hydrogen atom or a halogen atom;

$R^5$ is a hydrogen atom, a $C_{1-6}$ alkyl group or a $C_{1-20}$ acyl group;

$R^6$ and $R^7$ are independently a hydrogen atom or $R^6$ and $R^7$ may form a chemical bond together with each other comprising a group of the formula:

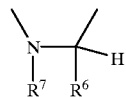

or a group of the formula:

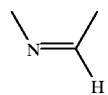

and D is —CH$_2$—; or a salt thereof.

15. A composition which comprises a pharmaceutical compound as claimed in claim 1 or a salt thereof and a physiologically acceptable carrier.

16. A method for preventing or treating sporozoasis in a vertebrate or an insect which comprises administering an effective amount of the compound as claimed in claim 1 or a salt thereof, to the vertebrate or insect.

* * * * *